United States Patent [19]

Frank

[11] Patent Number: 5,292,719
[45] Date of Patent: Mar. 8, 1994

[54] TETRALIN FORMATE ESTER AROMA CHEMICALS

[75] Inventor: Walter C. Frank, Holland, Pa.

[73] Assignee: Union Camp Corporation, Princeton, N.J.

[21] Appl. No.: 80,078

[22] Filed: Jun. 18, 1993

[51] Int. Cl.$^5$ .............................................. A61K 7/46
[52] U.S. Cl. ..................................... 512/19; 560/139
[58] Field of Search ........................... 560/139; 512/19

[56] References Cited

U.S. PATENT DOCUMENTS

| | | | |
|---|---|---|---|
| 2,800,511 | 7/1959 | Carpenter | 260/599 |
| 2,897,237 | 7/1959 | Carpenter | 260/592 |
| 3,244,751 | 4/1966 | Theimer et al. | 260/592 |
| 3,246,044 | 4/1966 | Wood et al. | 260/668 |
| 3,278,622 | 10/1966 | Stofberg et al. | 260/668 |
| 3,379,785 | 4/1968 | Kahn | 260/668 |
| 3,400,159 | 9/1968 | Theimer et al. | 260/592 |
| 3,442,640 | 5/1969 | Wood et al. | 71/124 |
| 3,509,215 | 4/1970 | Wood et al. | 260/592 |
| 3,856,875 | 12/1974 | Wood et al. | 260/668 |
| 4,162,256 | 7/1979 | Sprecker et al. | 260/345 |
| 4,284,818 | 8/1991 | Sato et al. | 568/323 |
| 4,352,748 | 10/1982 | Traas et al. | 252/522 |
| 4,406,828 | 9/1983 | Gozenbach et al. | 252/522 |
| 4,466,908 | 8/1984 | Sprecker et al. | 252/522 |
| 4,551,573 | 11/1985 | Cobb | 585/459 |
| 4,605,778 | 8/1986 | Willis et al. | 568/433 |
| 4,767,882 | 8/1988 | Suzukamo et al. | 560/100 |
| 4,877,910 | 10/1989 | Frank | 585/411 |
| 4,877,911 | 10/1989 | Frank | 585/411 |
| 4,877,912 | 10/1989 | Frank | 585/411 |
| 4,877,913 | 10/1989 | Frank | 585/411 |
| 4,877,914 | 10/1989 | Frank | 585/411 |
| 4,877,915 | 10/1989 | Frank | 585/411 |
| 4,877,916 | 10/1989 | Frank | 585/411 |
| 4,880,775 | 11/1989 | Christenson et al. | 512/12 |
| 4,908,349 | 3/1990 | Gozenbach | 512/26 |
| 5,087,770 | 2/1992 | Frank | 568/327 |
| 5,087,785 | 2/1992 | Frank | 585/459 |
| 5,095,152 | 3/1992 | Frank | 568/440 |
| 5,162,588 | 11/1992 | Fehr et al. | 568/328 |
| 5,185,318 | 2/1993 | Fehr et al. | 512/16 |
| 5,206,217 | 4/1993 | Frank | 512/18 |

FOREIGN PATENT DOCUMENTS

| | | |
|---|---|---|
| 0301375 | 2/1989 | European Pat. Off. . |
| 0393742 | 10/1990 | European Pat. Off. . |
| 0405427A2 | 1/1991 | European Pat. Off. . |
| 50-40761 | 4/1975 | Japan . |
| 57-40420 | of 1982 | Japan . |

OTHER PUBLICATIONS

Bedoukian, Paul Z., Perfumery and Flavoring Synthetics, 3rd Revised Ed., pp. 334–336 (Allured Publishing Corp., Illinois 1986).

Bedoukian, Paul Z., Perfumery and Flavoring Synthetics, 2nd Revised Ed., pp. 248–292 (Elsevier Publishing Co. 1967).

Beets, Structure–Activity Relationships in Human Chemoreception, pp. 161–381 (Applied Science Publishers Ltd., London).

Carey et al., Advanced Organic Chemistry, Part B: Reactions and Synthesis, pp. 383–386 (Plenum Press, NY 1977).

Effenberger, Electrophillic Reagents, *Angewandte Chemie* (Int. Ed. in English), vol. 19, No. 3, pp. 151–230 (1980).

Fehr et al., New Aromatic Musk Odorants: Design and Synthesis, *Helvetica Chimica Acta*, vol. 72, pp. 1537–1553 (1989).

Godfrey et al., Preparation of Methoxyphenols by Baeyer–Villiger Oxidation of Methoxybenzaldehydes, *J.C.S. Perkin I*, pp. 1353–1354 (1974).

Hannan et al., Synthesis of Bromonaphthoquinones from 1,5-Dimethoxynaphthalene, *J. Org. Chem.*, vol. 44, No. 13, pp. 2153–2158 (1979).

Harrison et al., Compendium of Organic Synthetic Methods, pp. 84–85 (Wiley-Interscience, NY 1971).

(List continued on next page.)

*Primary Examiner*—James H. Reamer
*Attorney, Agent, or Firm*—Woodcock Washburn Kurtz Mackiewicz & Norris

[57] ABSTRACT

The present invention relates to novel formate ester tetralin compounds having fragrant musk-like aroma.

42 Claims, No Drawings

OTHER PUBLICATIONS

Hauser et al., Regiospecific Oxidation of Methyl Groups in Dimethylanisoles, *Synthesis*, pp. 723–724 (1987).

Huang et al., A Convenient Synthesis of Aryl Formatest, *J. Chem. Research* (Synop), pp. 292–293 (1991).

Imamotot et al., Cerium(IV) Trifluoromethanesulfonate as a Strong Oxidizing Agent, *Chemistry Letters*, pp. 1445–1446 (1990).

Kreh et al., Selective Oxidations With Ceric Methanesulfonate and Ceric Trifluoromethanesulfonate, *Tetrahedron Ltrs*, vol. 28, No. 10, pp. 1067–1068 (1987).

Laing et al., Synthetic Steroids. Part IX. A New Route to 19-Nor-steroids, *J. Chem. soc.* (C), pp. 2915–2918 (1968).

March, J., Advanced Organic Chemistry: Reactions, Mechanisms and Structure, 4th Ed., pp. 1098–1099, 1184–1185 (John Wiley & Sons, NY 1992).

Nikaido et al., Acid-Catalyzed Oxidation of Benzaldehydes to Phenols by Hydrogen Peroxide, *J. Org. Chem.*, vol. 49, pp. 4740–4741 (1984).

Olah et al., Formylating Agents, *Chemical Reviews*, vol. 87, No. 4, pp. 671–686 (1987).

Ohloff et al., Chemical Classification and Structure—Odour Relationships, Perfumes: Art, Science and Technology, pp. 287–330 (Amsterdam 1991).

Rahm et al., Acetone Cyanohydrin, A Convenient Formylation Reagent For Arenes, *Synthetic Communications*, vol. 12, No. 6, pp. 485–487 (1982).

Rieche et al., Aromatic Aldehydes. Mesitaldehyde, *Organic Syntheses*, Collective vol. 5, pp. 49–50 (1973).

Syper, The Baeyer–Villiger Oxidation of Aromatic Aldehydes and Ketones with Hydrogen Peroxide Catalyzed by Selenium Compounds, *Synthesis*, pp. 167–172 (1989).

Syper, Partial Oxidation of Aliphatic Side Chains With Oerium (IV), *Tetrahedron Letters*, No. 37, pp. 4493–4498 (1966).

Syper, Silver (II) As An Oxidant For Organic Compounds, *Tetrahedron Letters*, No. 42, pp. 4193–4198 (1967).

Theimer, Fragrance Chemistry: The Science of the Sense of Smell, pp. 509–534 (Academic Press 1982).

French Patent No. 1,392,804 (as reported in *Chemical Abstracts*, 29-Essential Oils and Cosmetics, vol. 63, p. 6781 (1965)).

Chastrette, Importance of Hydrogen Bonding in the Recognition of Musky Odours, ECRO VIII: Abstracts, pp. 176–177.

Perrier, *Chem. Ber.*, vol. 33, pp. 815 et seq. (1900).

Perrier, *Bull Soc. Chim. France*, pp. 859 et seq. (1904).

TETRALIN FORMATE ESTER AROMA CHEMICALS

BACKGROUND OF THE INVENTION

The present invention relates to novel formate ester tetralin compounds having fragrant musk-like aroma.

Musk fragrances are in great demand for use in various products such as in perfumes, colognes, cosmetics, soaps and others. However, natural musk, which is obtained from the Asian musk deer, is extremely scarce and is quite expensive. Accordingly, fragrance chemists have spent considerable time searching for synthetic products which duplicate or closely simulate this natural musk scent.

As a result of these research efforts, a number of different synthetic musks have been discovered. Among such synthetic compounds is a derivative of 1,1,3,4,4,6-hexamethyl-1,2,3,4-tetrahydronaphthalene (HMT). HMT, for example, is converted to 7-acetyl-1,1,3,4,4,6-hexamethyl-1,2,3,4-tetrahydronaphthalene, to yield a well known musk perfume of the tetralin series. Because of its clean musk fragrance and its ability to retain that fragrance over long periods of time, this compound is of great commercial value as a synthetic musk perfume substitute for the expensive, natural musk perfumes of the macrocyclic ketone series.

New and or better musk aroma compounds are needed to meet the demands of the fragrance industries. The present invention is directed to this, as well as other, important ends.

SUMMARY OF THE INVENTION

The present invention provides novel compounds of the formula [I]:

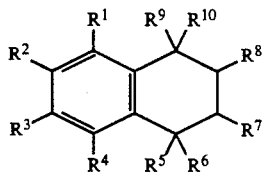

wherein
$R^1$ is —H, —CH$_3$, —CH$_2$CH$_3$, —OCH$_3$ or —OH,
$R^2$ and $R^3$ are, independently, —H, —CH$_3$, —CH$_2$CH$_3$, —OCH$_3$, —OH or —OC(O)H,
$R^4$ is —H,
$R^5$ is —H, —CH$_3$ or —CH$_2$CH$_3$,
or $R^4$ and $R^5$, taken together, are —(CH$_2$)$_2$—,
$R^6$ is —CH$_3$ or —CH$_2$CH$_3$,
$R^7$ is —H, —CH$_3$ or —CH$_2$CH$_3$,
or $R^6$ and $R^7$, taken together, are —(CH$_2$)$_3$—,
$R^8$ and $R^9$ are, independently, —H, —CH$_3$ or —CH$_2$CH$_3$, and
$R^{10}$ is —CH$_3$,
provided that (i) one of $R^2$ and $R^3$ is —OC(O)H, and one of $R^2$ and $R^3$ is other than —OC(O)H, (ii) when $R^1$ is —H, then $R^2$ and $R^3$ are other than —OCH$_3$ or —OH, (iii) no more than one of $R^5$ and $R^9$ is —H, (iv) no more than one of $R^5$, $R^6$, $R^7$, $R^8$ and $R^9$ is —CH$_2$CH$_3$, (v) when $R^1$ is —OCH$_3$, then $R^2$ and $R^3$ are other than —H or —OH, (vi) when $R^1$ is —OH, then $R^2$ and $R^3$ are other than —OH or —OCH$_3$, (vii) when $R^1$ is —CH$_3$ or —CH$_2$CH$_3$, then at least one of $R^7$ and $R^8$ are H, (viii) when $R^4$ and $R^5$, taken together, are —(CH$_2$)$_2$—, then $R^1$ is —H, —OCH$_3$ or —OH, $R^7$ is —H, and $R^8$ is —H, and (ix) when $R^6$ and $R^7$, taken together, are —(CH$_2$)$_3$—, then $R^1$ is —H, —OCH$_3$ or —OH, and $R^8$ is —H.

The foregoing compounds possess an active musk aroma having utility in the fragrance industry. The compounds of the invention may be used alone, or in combination with carriers, additional perfumery materials, and/or other ingredients, to provide various products, such as perfumes, colognes, soaps, and cosmetics.

DETAILED DESCRIPTION OF THE INVENTION

As noted above, the present invention is directed to novel musk compounds of the formula [I]:

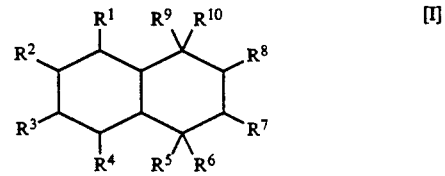

In the above formula [I], the R substituents may be selected as follows: $R^1$ may be selected from the group consisting of —H, —CH$_3$, —CH$_2$CH$_3$, —OCH$_3$ and —OH; $R^2$ may be selected from the group consisting of —H, —CH$_3$, —CH$_2$CH$_3$, —OCH$_3$, —OH and —OC(O)H; $R^3$ may be selected from the group consisting of —H, —CH$_3$, —CH$_2$CH$_3$, —OCH$_3$, —OH and —OC(O)H; $R^4$ may be —H, $R^5$ may be selected from the group consisting of —H, —CH$_3$, and —CH$_2$CH$_3$; or $R^4$ and $R^5$, taken together, may be —(CH$_2$)$_2$—; $R^6$ may be selected from the group consisting of —CH$_3$ and —CH$_2$CH$_3$; $R^7$ may be selected from the group consisting of —H, —CH$_3$ and —CH$_2$CH$_3$; or $R^6$ and $R^7$, taken together, may be —(CH$_2$)$_3$—; $R^8$ may be selected from the group consisting of —H, —CH$_3$ and —CH$_2$CH$_3$; $R^9$ may be selected from the group consisting of —H, —CH$_3$ and —CH$_2$CH$_3$; and $R^{10}$ may be —CH$_3$.

As the above indicates, the compound of formula [I] may be a bicyclic compound, where $R^4$ and $R^5$ are other than —(CH$_2$)$_2$—, and $R^6$ and $R^7$ are other than —(CH$_2$)$_3$—. The compound of formula [I] may alternatively be a tricyclic compound by virtue of $R^4$ and $R^5$ being taken together as —(CH$_2$)$_2$—, such as a compound of the formula [II]:

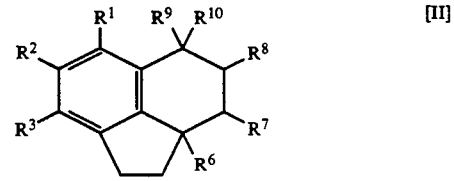

Similarly, the compound of formula [I] may alternatively be a tricyclic compound by virtue of $R^6$ and $R^7$ being taken together as —(CH$_2$)$_3$—, such as a compound of the formula [III]:

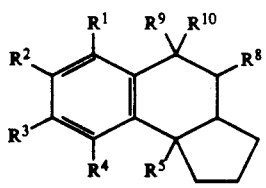

The foregoing selection of R substituents should, however, be made with the following qualifications in mind: that one of $R^2$ and $R^3$ is —OC(O)H, and the other of $R^2$ and $R^3$ is other than —OC(O)H; that when $R^1$ is —H, then $R^2$ and $R^3$ are both other than —OCH$_3$ or —OH; that no more than one of $R^5$ or $R^9$ is —H; that no more than one of $R^5$, $R^6$, $R^7$, $R^8$ or $R^9$ is —CH$_2$CH$_3$; that when $R^1$ is —OCH$_3$, then $R^2$ and $R^3$ are both other than —H or —OH; that when $R^1$ is —OH, then $R^2$ and $R^3$ are both other than —OH or —OCH$_3$; that when $R^1$ is —CH$_3$ or —CH$_2$CH$_3$, then one or both of $R^7$ and $R^8$ are H; that when $R^4$ and $R^5$, taken together, are —(CH$_2$)$_2$— (that is, a tricyclic compound, where the third ring structure is at the $R^4$ and $R^5$ position), then $R^1$ is —H, —OCH$_3$ or —OH, $R^7$ is —H, and $R^8$ is —H; and that when $R^6$ and $R^7$, taken together, are —(CH$_2$)$_3$— (that is, a tricyclic compound, where the third ring structure is at the $R^6$ and $R^7$ position), then $R^1$ is —H, —OCH$_3$ or —OH, and $R^8$ is —H.

For reasons of their fragrance characteristics, synthesis advantages, formulation benefits, and/or other values, the following are preferable classes of compounds within the scope of Formula [I]:

Compounds of Formula [I] wherein $R^1$ is —H, —CH$_3$, —OH or —OCH$_3$;

Compounds of Formula [I] wherein $R^2$ is —OC(O)H;

Compounds of formula [I] wherein $R^3$ is —CH$_3$ or —CH$_2$CH$_3$;

Compounds of formula [I] wherein $R^1$ is —OH or —OCH$_3$, $R^2$ is —OC(O)H, $R^3$ is —CH$_3$ or —CH$_2$CH$_3$, $R^4$ is —H, $R^5$ is —CH$_3$, $R^6$ is —CH$_3$, $R^7$ is —H or CH$_3$, $R^8$ is —H or —CH$_3$, $R^9$ is —CH$_3$, and $R^{10}$ is —CH$_3$;

Compounds of formula [I] wherein $R^1$ is —H or —CH$_3$, $R^2$ is —OC(O)H, $R^3$ is —CH$_3$ or —CH$_2$CH$_3$, $R^4$ is —H, $R^5$ is —CH$_3$, $R^6$ is —CH$_3$, $R^7$ is —H or —CH$_3$, $R^8$ is —H or —CH$_3$, $R^9$ is —CH$_3$, and $R^{10}$ is —CH$_2$;

Compounds of formula [I] wherein $R^1$ is —H, —OH or —OCH$_3$, $R^2$ is —OC(O)H, $R^3$ is —CH$_3$, $R^4$ and $R^5$, taken together, are —(CH$_2$)$_2$—, $R^6$ is —CH$_3$, $R^7$ is —H, $R^8$ is —H, $R^9$ is —CH$_3$, and $R^{10}$ is —CH$_3$; and Compounds of formula [I] wherein $R^1$ is —H, —OH or —OCH$_3$, $R^2$ is —OC(O)H, $R^3$ is —CH$_3$, $R^4$ is —H, $R^5$ is —CH$_3$, $R^6$ and $R^7$, taken together, are —(CH$_2$)$_3$—, $R^8$ is —H, $R^9$ is —CH$_3$, and $R^{10}$ is —CH$_3$.

One of the foregoing classes of compounds, the most preferred class is that wherein $R^1$ is —H or —CH$_3$, $R^2$ is —OC(O)H, $R^3$ is —CH$_3$ or —CH$_2$CH$_3$, $R^4$ is H, $R^5$, $R^6$, $R^9$ and $R^{10}$ are —CH$_3$, and $R^7$ and $R^8$ are —H or —CH$_3$.

Specific compounds of Formula [I] which are most preferred, for reasons of fragrance characteristics, synthesis advantages, formulation benefits, and/or other values are as follows:

The compound of Formula [I] wherein $R^1$ is —OCH$_3$, $R^2$ is —OC(O)H, $R^3$ is —CH$_3$, $R^4$ is —H, $R^5$ is CH$_3$, $R^6$ is CH$_3$, $R^7$ is —H, $R^8$ is —H, $R^9$ is CH$_3$, and $R^{10}$ is —CH$_3$;

The compound of Formula [I] wherein $R^1$ is —OCH$_3$, $R^2$ is —OC(O)H, $R^3$ is —CH$_2$CH$_3$, $R^4$ is —H, $R^5$ is CH$_3$, $R^6$ is CH$_3$, $R^7$ is —H, $R^8$ are —H, $R^9$ is CH$_3$, and $R^{10}$ is —CH$_3$;

The compound of Formula [I] wherein $R^1$ is —OH, $R^2$ is —OC(O)H, $R^3$ is —CH$_3$, $R^4$ is —H, $R^5$ is —CH$_3$, $R^6$ is CH$_3$, $R^7$ is —H, $R^8$ is —H, $R^9$ —CH$_3$, and $R^{10}$ is —CH$_3$;

The compound of Formula [I] wherein $R^1$ is —OH, $R^2$ is —OC(O)H, $R^3$ is —CH$_2$CH$_3$, $R^4$ is —H, $R^5$ is —CH$_3$, $R^6$ is —CH$_3$, $R^7$ is —H, $R^8$ is —H, $R^9$ is —CH$_3$, and $R^{10}$ is —CH$_3$;

The compound of Formula [I] wherein $R^1$ is —OCH$_3$, $R^2$ is —OC(O)H, $R^3$ is —CH$_3$, $R^4$ is —H, $R^5$ is —CH$_3$, $R^6$ is CH$_3$, $R^7$ is —CH$_3$, $R^8$ is —H, $R^9$ is —CH$_3$, and $R^{10}$ is —CH$_3$;

The compound of Formula [I] wherein $R^1$ is —OCH$_3$, $R^2$ is —OC(O)H, $R^3$ is —CH$_2$CH$_3$, $R^4$ is —H, $R^5$ is CH$_3$, $R^6$ is CH$_3$, $R^7$ is —CH$_3$, $R^8$ is —H, $R^9$ is —CH$_3$, and $R^{10}$ is —CH$_3$;

The compound of Formula [I] wherein $R^1$ is —OH, $R^2$ is —OC(O)H, $R^3$ is —CH$_3$, $R^4$ is —H, $R^5$ is —CH$_3$, $R^6$ is —CH$_3$, $R^7$ is —CH$_3$, $R^8$ are —H, $R^9$ is —CH$_3$, and $R^{10}$ are —CH$_3$;

The compound of Formula [I] wherein $R^1$ is —OH, $R^2$ is —OC(O)H, $R^3$ is —CH$_2$CH$_3$, $R^4$ is —H, $R^5$ is CH$_3$, $R^6$ is CH$_3$, and $R^7$ is —CH$_3$, $R^8$ is —H, $R^9$ is —CH$_3$, and $R^{10}$ is —CH$_3$;

The compound of Formula [I] wherein $R^1$ is —H, $R^2$ is —OC(O)H, $R^3$ is —CH$_3$, $R^4$ is —H, $R^5$ is —CH$_3$, $R^6$ is —CH$_3$, $R^7$ is —CH$_3$, $R^8$ is —H, $R^9$ is —CH$_3$, and $R^{10}$ is —CH$_3$;

The compound of Formula [I] wherein $R^1$ is —H, $R^2$ is —OC(O)H, $R^3$ is —CH$_3$, $R^4$ is —H, $R^5$ is —CH$_3$, $R^6$ is —CH$_3$, $R^7$ is —H, and $R^8$ is —H, $R^9$ is —CH$_3$, and $R^{10}$ is —CH$_3$;

The compound of Formula [I] wherein $R^1$ is —H, $R^2$ is —OC(O)H, $R^3$ is —CH$_3$, $R^4$ is —H, $R^5$ is —CH$_3$, $R^6$ is —CH$_3$, $R^7$ is —H, $R^8$ is —CH$_3$, $R^9$ is —CH$_3$, and $R^{10}$ is —CH$_3$;

The compound of Formula [I] wherein $R^1$ is —CH$_3$, $R^2$ is —OC(O)H, $R^3$ is —CH$_3$, $R^4$ is —H, $R^5$ is —CH$_3$, $R^6$ is —CH$_3$, $R^7$ is —CH$_3$, $R^8$ is —H, $R^9$ is —CH$_3$, and $R^{10}$ is —CH$_3$;

The compound of Formula [I] wherein $R^1$ is —CH$_3$, $R^2$ is —OC(O)H, $R^3$ is —CH$_3$, $R^4$ is —H, $R^5$ is —CH$_3$, $R^6$ is —CH$_3$, $R^7$ is —H, and $R^8$ is —H, $R^9$ is —CH$_3$, and $R^{10}$ is —CH$_3$;

The compound of Formula [I] wherein $R^1$ is —CH$_3$, $R^2$ is —OC(O)H, $R^3$ is —CH$_3$, $R^4$ is —H, $R^5$ is —CH$_3$, $R^6$ is —CH$_3$, $R^7$ is —H, and $R^8$ is —CH$_3$, $R^9$ is —CH$_3$, and $R^{10}$ is —CH$_3$;

The compound of Formula [I] wherein $R^1$ is —H, $R^2$ is —OC(O)H, $R^3$ is —CH$_3$, $R^4$ is —H, $R^5$ is —CH$_3$, $R^6$ is —CH$_3$, $R^7$ is —CH$_3$, $R^8$ is —CH$_3$, $R^9$ is —CH$_3$, and $R^{10}$ is —CH$_3$;

The compound of Formula [I] wherein $R^1$ is —H, $R^2$ is —OC(O)H, $R^3$ is —CH$_2$CH$_3$, $R^4$ is —H, $R^5$ is —CH$_3$, $R^6$ is —CH$_3$, $R^7$ is —H, and $R^8$ is —H, $R^9$ is —CH$_3$, and $R^{10}$ is —CH$_3$;

The compound of Formula [I] wherein $R^1$ is —H, $R^2$ is —OC(O)H, $R^3$ is —CH$_3$, $R^4$ and $R^5$, taken together, are —(CH$_2$)$_2$—, $R^6$ is —CH$_3$, $R^7$ is —H, $R^8$ is —H, $R^9$ is —CH$_3$, and $R^{10}$ is —CH$_3$;

The compound of Formula [I] wherein $R^1$ is —OH, $R^2$ is —OC(O)H, $R^3$ is —CH$_3$, $R^4$ and $R^5$, taken together, are —(CH$_2$)$_2$—, $R^6$ is —CH$_3$, $R^7$ is —H, $R^8$ is —H, $R^9$ is —CH$_3$, and $R^{10}$ is —CH$_3$;

The compound of Formula [I] wherein $R^1$ is —OCH$_3$, $R^2$ is —OC(O)H, $R^3$ is —CH$_3$, $R^4$ and $R^5$, taken together, are —(CH$_2$)$_2$—, $R^6$ is —CH$_3$, $R^7$ is —H, $R^8$ is —H, $R^9$ is —CH$_3$, and $R^{10}$ is —CH$_3$;

The compound of Formula [I] wherein $R^1$ is —H, $R^2$ is —OC(O)H, $R^3$ is —CH$_3$, $R^4$ is —H, $R^5$ is —CH$_3$, $R^6$ and $R^7$, taken together, are —(CH$_2$)$_3$—, $R^8$ is —H, $R^9$ is —CH$_3$, and $R^{10}$ is —CH$_3$;

The compound of Formula [I] wherein $R^1$ is —OH, $R^2$ is —OC(O)H, $R^3$ is —CH$_3$, $R^4$ is —H, $R^5$ is —CH$_3$, $R^6$ and $R^7$, taken together, are —(CH$_2$)$_3$—, $R^8$ is —H, $R^9$ is —CH$_3$, and $R^{10}$ is —CH$_3$; and The compound of Formula [I] wherein $R^1$ is —OCH$_3$, $R^2$ is —OC(O)H, $R^3$ is —CH$_3$, $R^4$ is —H, $R^5$ is —CH$_3$, $R^6$ and $R^7$, taken together, are —(CH$_2$)$_3$—, $R^8$ is —H, $R^9$ is —CH$_3$, and $R^{10}$ is —CH$_3$.

Of the foregoing compounds, the most preferred compounds are as follows:

The compound of Formula [I] wherein $R^1$ is —OCH$_3$, $R^2$ is —OC(O)H, $R^3$ is —CH$_3$, $R^4$ is —H, $R^5$, $R^6$, $R^9$ and $R^{10}$ are —CH$_3$, and $R^7$ and $R^8$ are —H;

The compound of Formula [I] wherein $R^1$ is —OH, $R^2$ is —OC(O)H, $R^3$ is —CH$_3$, $R^4$ is —H, $R^5$ is —CH$_3$, $R^6$ is —CH$_3$, $R^7$ is —H, $R^8$ is —H, $R^9$ is —CH$_3$, and $R^{10}$ is —CH$_3$;

The compound of Formula [I] wherein $R^1$ is —OCH$_3$, $R^2$ is —OC(O)H, $R^3$ is —CH$_3$, $R^4$ is —H, $R^5$ is —CH$_3$, $R^6$ is —CH$_3$, $R^7$ is —CH$_3$, and $R^8$ are —H, $R^9$ is —CH$_3$, and $R^{10}$ is —CH$_3$;

The compound of Formula [I] wherein $R^1$ is —H, $R^2$ is —OC(O)H, $R^3$ is —CH$_3$, $R^4$ is —H, $R^5$ is —CH$_3$, $R^6$ is —CH$_3$, $R^7$ is —CH$_3$, $R^8$ is —H, $R^9$ is —CH$_3$, and $R^{10}$ is —CH$_3$;

The compound of Formula [I] wherein $R^1$ is —H, $R^2$ is —OC(O)H, $R^3$ is —CH$_3$, $R^4$ is —H, $R^5$ is —CH$_3$, $R^6$ is —CH$_3$, $R^7$ is —CH$_3$, $R^8$ is —CH$_3$, $R^9$ is —CH$_3$, and $R^{10}$ is —CH$_3$; and The compound of Formula [I] wherein $R^1$ is —H, $R^2$ is —OC(O)H, $R^3$ is —CH$_2$CH$_3$, $R^4$ is —H, $R^5$ is —CH$_3$, $R^6$ is —CH$_3$, $R^7$ is —H, and $R^8$ is —H, $R^9$ is —CH$_3$, and $R^{10}$ is —CH$_3$;

The novel formate ester tetralin compounds of the present invention may be prepared in various fashions. In the preferable protocol, alkyl tetralins are first prepared. Then the alkyl tetralins are formylated (that is, the radical —C(O)H is added to the benzene ring of the tetralin structure, to form an alkyl tetralin aldehyde), or oxidized (that is, a —CH$_3$ substituent on the benzene ring of the tetralin structure is oxidized to —C(O)H, to form an alkyl tetralin aldehyde). Finally, the alkyl tetralin aldehyde is oxidized (that is, the radical —C(O)H on the benzene ring of the tetralin structure is oxidized to —OC(O)H, to form an alkyl tetralin ester), yielding the formate ester tetralin compounds of Formula [I]. Examples 1-24 below illustrate specific methodology which may be utilized for the preparation of compounds of the present invention.

In general, alkyl tetralin compounds or alkyl tetralin aldehyde compounds may be prepared by numerous synthetic routes which will be readily apparent to those skilled in the art, once armed with the present disclosure. Examples of suitable methodology include Frank, U.S. Pat. Nos. 4,877,911, 4,877,914, 4,877,910, 4,877,916, 4,877,915, 4,877,913, 4,877,912, and 5,087,785, Carpenter, U.S. Pat. No. 2,897,237, Carpenter, U.S. Pat. No. 2,800,511, Fehr et al., U.S. Pat. No. 5,162,588, Willis et al., U.S. Pat. No. 4,605,778, Trass et al., U.S. Pat. No. 4,352,748, Cobb et al., U.S. Pat. No. 4,551,573, Wood, U.S. Pat. No. 3,246,044, Wood et al., U.S. Pat. No. 3,856,875, Sato et al., U.S. Pat. No. 4,284,818, Kahn, U.S. Pat. No. 3,379,785, Suzukamo et al., U.S. Pat. No. 4,767,882, Gonzenbach, U.S. Pat. No. 4,908,349, European Patent Application Publication No. 0 393 742, European Patent Application Publication No. 0 301 375, Japanese Patent No. SHO 57-40420, Fehr et al., *Helv. Chim. Acta*, Vol. 72, pp. 1537–1553 (1989), and Bedoukian, Paul Z., *Perfumery and Flavoring Synthetics*. 3rd ed., pp. 334–336, Allured Publishing Corporation, Wheaton, Ill. (1986), the disclosures of each of which are hereby incorporated herein by reference, in their entirety.

In accordance with Frank, U.S. Pat. No. 4,877,910, for example, various polyalkyl tetrahydronapthalene compounds may be prepared by carrying out a cyclialkylation reaction between an olefinic compound and a substituted benzene compound in the presence of a hydride abstracting reagent, an alkyl halide or hydrogen halide, a Lewis acid, and, optionally, a phase transfer agent. Suitable olefinic compounds include 2,3-dimethyl-1-butene and 2,3-dimethyl-2-butene. Suitable substituted benzene compounds include isopropyl toluene (para-cymene), 1-ethyl-4-isopropylbenzene, 1-n-propyl-4-isopropyl-benzene, and 1-tertiary-butyl-4-isopropyl-benzene. A suitable hydride abstracting reagent is 2,4,4-trimethyl-2-pentene (diisobutylene-2). Suitable alkyl halides include tertiary-butyl chloride, tertiary-amyl chloride, 2-methyl-2-chloropentane, 3-methyl-3-chloropentane and 1,8-dichloro-para-menthane. Suitable Lewis acids include aluminum chloride, aluminum bromide, aluminum iodide, monofluorodichloroaluminum, monobromodichloroaluminum and monoiododichloroaluminum. Suitable phase transfer agents include methyltrioctylammonium chloride (referred to herein as "MTOAc"), and a mixture of methyltrioctyl-ammonium chloride and methyltridecylammonium chloride (the mixture being marketed under the tradename Adogen-464 ™, by Sherex Co., located in Dublin, Ohio).

In general, the molar proportions of the reagents employed in the foregoing process can be varied over a relatively wide range. However, where phase transfer agents are employed in the process, it is important, for the best results, to maintain a ratio of less than one mole of phase transfer agent per mole of Lewis acid. Preferably, the molar ratio is about 0.8 to 1.0, more preferably 0.5 to 1.0, phase transfer agent to Lewis acid. In addition, it is also preferable to use a mixture of olefinic compound, hydride abstracting reagent, alkyl halide and hydrogen halide, wherein these components are present in a molar range of about 1.0 to about 5.0 moles of olefin per mole of combine halides plus reagent. More preferably, the olefin, and the combined halides plus reagent are present in nearly equimolar amounts, that is, about 1.0 mole of olefin per mole of combined halides plus reagent. Preferably, the substituted benzene compound is present in a range of about 0.5 to about 10 moles per mole of olefin, more preferably in a range of about 0.5 to about 5.0 per mole of olefin. In a most preferred embodiment, each of the benzene compound, olefin, and the combination of alkyl halide, hydrogen halide plus hydride abstracting reagent, are present nearly in equimolar amounts, that is, about 1.0 mole of benzene compound, to about 1.0 mole of olefin, to about 1.0 mole of combined halides plus hydride abstracting reagent. The amount of Lewis acid utilized is preferably in the range of about 2% to about 10% by weight of the Lewis acid based on the combined weight of the substituted benzene, olefin, alkyl halide, hydrogen halide plus hydride abstracting reagent.

The foregoing reaction is generally carried out using a solvent, although, if desired, substituted benzene, one of the starting materials, may be employed in large excess in lieu of an additional solvent. Suitable solvents include methylene chloride, chloroform, carbon tetrachloride, ethylene chloride, ethylidene chloride, 1,1,1-trichloroethane, 1,1,2-trichloroethane, 1,1,2,2-tetrachloroethane, 1,2-dichloroethylene, trichloro-ethylene, tetrachloroethylene, 1,2,3-trichloropropane, amyl chloride, ethylene bromide, monochlorobenzene, orthodichlorobenzene, bromobenzene, fluorobenzene, n-hexane, n-heptane, n-octane, benzene, toluene, ethylbenzene and xylene. Preferred for reasons of yield, safety and/or process engineering are the unhalogenated aliphatic and unhalogenated alicyclic hydrocarbons.

The alkylation reaction described above can be carried out in any suitable vessel which provides efficient contacting between the Lewis acid and the other reactants. For simplicity, a stirred batch reactor can be employed. Moreover, the reaction vessel used should be resistant to the possibly corrosive nature of the catalyst. Glass-lined vessels would be suitable for this purpose. Additional vessel materials will be apparent to those skilled in the art.

The reagents of the present process may be added in any order, although where the process is carried out with a phase transfer agent, the preferred mode is to add the solvent, the Lewis acid and the phase transfer agent first, allow sufficient time for the Lewis acid to become substantially dissolved in the solvent, and then add the remaining reagents. Generally, 15 to 30 minutes are needed for the Lewis acid to become substantially dissolved in the solvent.

Ideally, the reaction is carried out at temperatures ranging from about −30° C. to about 50° C., preferably at temperatures ranging from about −10° C. to about 40° C., and most preferably at temperatures ranging from about 0° C. to about 30° C.

The pressure at which the reaction is carried out is not critical. If the reaction is carried out in a sealed vessel, autogenous pressure is acceptable, although higher or lower pressures, if desired, may be employed. The reaction can also be carried out at atmospheric pressure in an open reaction vessel, in which case the vessel is preferably equipped with a moisture trap to prevent significant exposure of Lewis acid to moisture. The reaction can take place in an oxygen atmosphere, or an inert atmosphere as in the presence of a gas such as nitrogen, argon and the like, the type of atmosphere also not being critical.

Reaction time is generally rather short and is often dictated by the kind of equipment employed. Sufficient time must be provided, however, for thorough contacting of the substituted benzene compound, the olefinic compound, the Lewis acid and the phase transfer agent. Generally the reaction proceeds to completion in about 1 to about 7 hours.

Product can be recovered by first quenching the reaction mixture in cold water or on crushed ice, preferably on ice, and then processing the mixture in the usual manner for Friedel-Crafts reactions to extract the desired alkyl-substituted tetrahydronaphthalene compounds. Suitable extraction protocol is described, for example, in *Friedel-Crafts Reactions*. Typically, following quenching and the resultant phase separation, the organic layer is washed an additional time with water to aid in removal of the Lewis acid. One or more additional washings can be carried out with dilute alkali solution to further aid Lewis acid removal. Pure product can then be recovered by subjecting the washed reaction mixture to reduced pressure fractional distillation.

Exemplary tetrahydronaphthalene compounds which may be prepared by the foregoing process include 1,1,3,4,4,6-hexamethyl-1,2,3,4-tetrahydronaphthalene (HMT), 6-ethyl-1,1,3,4,4-pentamethyl-1,2,3,4-tetrahydronaphthalene, 6-tertiary-butyl-1,1,3,4,4-pentamethyl-1,2,3,4-tetrahydronaphthalene, and 6-n-propyl-1,1,3,4,4-pentamethyl-1,2,3,4-tetrahydronaphthalene.

The disclosures of Frank, U.S. Pat. No. 4,877,910, are hereby incorporated herein by reference in their entirety.

Alkyl tetralin compounds may then be formylated or oxidized to form alkyl tetralin aldehydes using conventional formylation or oxidation technology, as will be readily apparent to one skilled in the art once armed with the present disclosure.

Specifically, to prepare alkyl tetralin aldehydes from alkyl tetralins using formylation techniques, the alkyl tetralins are preferably reacted with $\alpha,\alpha$-dichloromethyl methyl ether, in a solvent such as an organic solvent (preferably a halogenated organic solvent such as, for example, anhydrous methylene chloride), in the presence of a Lewis acid (preferably titanium tetrachloride). Other suitable halogenated solvents and Lewis acids are described above, and will be readily apparent to those skilled in the art, once armed with the present disclosures. In general, formylation methods are well known in the art, and are described in many of the patents and publications discussed above for the preparation of alkyl tetralin compounds, as well as, for example, in *Organic Syntheses*, Collective Vol. 5, pp. 49–50, by A. Rieche, H. Gross, and E. Hoft, edited by H. E. Baumgarten, John Wiley and Sons (New York, N.Y. 1973), Rahm, *Synthetic Communications*, Vol. 12, No. 6, pp. 485–487 (1982), Effenberger, *Angewandte Chemie International Edition (English)*, Vol. 19, No. 3, pp. 151–230 (1980), Olah et al., *Chemical Reviews*, Vol. 87, No. 4, pp. 671–686 (1987), and Hauser et al., *Synthesis*, pp. 723–724 (August 1987), the disclosures of each of which are incorporated herein by reference, in their entirety.

Alternatively, to prepare alkyl tetralin aldehydes from alkyl tetralins using oxidation techniques, the alkyl tetralins are preferably reacted with ceric ammonium nitrate ($Ce(NO_3)_4 \cdot NH_4NO_3$), a strong oxidant for organic compounds, in the presence of acetic acid. In general, these and other suitable oxidation methods are well known in the art, and are described, for example, in Syper, *Tetrahedron Letters*, No. 37, pp. 4493–4498 (1966), Laing et al., *J. Chem. Soc.* (C), pp. 2915–2918 (1968), Imamoto et al., *Chemistry Letters*, pp. 1445–1446 (1990), Kreh et al., *Tetrahedron Letters*, Vol. 28, No. 10, pp. 1067–1068 (1987), Hauser et al., *Communications*, pp. 72–73 (August 1987), and Syper, *Tetrahedron Letters*, No. 42, pp. 4193–4198 (1967).

To prepare the formate ester tetralin compounds of Formula [I], the alkyl tetralin aldehydes may then be further oxidized (that is, the —C(O)H substituent on the benzene ring of the tetralin structure is oxidized to a —OC(O)H substituent, to form an alkyl tetralin formate ester), using conventional oxidation technology, producing alkyl tetralin formate ester compounds having a very fine, musk-like fragrance, a characteristic which renders them highly valuable for use in the perfumery industry. Specifically, to produce the formate ester compounds of the invention, a Baeyer-Villager-type reaction is preferably employed. In accordance with that process, the formylated compounds may be reacted with a peracid, preferably meta-chloro-perbenzoic acid, in a solvent such as an organic solvent, preferably a halogenated organic solvent such as, for example, anhydrous methylene chloride. Other suitable peracids include pertrifluoracetic acid and peracetic acid. Other suitable halogenated solvents are as discussed above. Such oxidation methods are discussed, for example, in Carey, Francis A., and Richard J. Sundberg, *Advanced Organic Chemistry*, Part B, pp. 383-386 (Plenum Press, New York 1977), Harrison, Ian T. and Harrison, Shuyen, *Compendium of Organic Synthetic Methods*. p. 84, John Wiley & Sons, New York, N.Y. (1971), March, Jerry, *Advanced Organic Chemistry*, 4th ed., John Wiley & Sons, New York, N.Y. (1992), Hannan et al., *J. Org. Chem.*, Vol. 44, No. 13, pp. 2153-2158 (1979), Hauser et al., *Communications*, pp. 72-73 (August 1987), Syper, *Synthesis*, pp. 167-172 (1989), Godfrey et al., *J.C.S. Perkin I*, pp. 1353-1354 (1974), Nakaido et al., *J. Org. Chem.*, Vol. 49, pp. 4740-4741 (1984), and Huang et al., *J. Chem. Research (Synop)*, pp. 292-293 (1991), the disclosures of each of which are hereby incorporated herein by reference, in their entirety.

Further purification of the formate ester tetralin compounds of Formula [I] may be carried out, if desired, using, for example, standard fractional distillation techniques, as well as other conventional extraction, distillation, crystallization and chromatography techniques, and the like.

Exemplary novel formate ester tetralin compounds within the scope of Formula [I] are shown in Table I below.

TABLE I

| Compound | $R^1$ | $R^2$ | $R^3$ | $R^4$ | $R^5$ | $R^6$ | $R^7$ | $R^8$ | $R^9$ | $R^{10}$ |
|---|---|---|---|---|---|---|---|---|---|---|
| 1 | —H | —H | —OC(O)H | —H | —H | —CH$_3$ | —H | —H | —CH$_3$ | —CH$_3$ |
| 2 | —H | —H | —OC(O)H | —H | —H | —CH$_3$ | —H | —H | —CH$_2$CH$_3$ | —CH$_3$ |
| 3 | —H | —H | —OC(O)H | —H | —H | —CH$_3$ | —H | —CH$_3$ | —CH$_3$ | —CH$_3$ |
| 4 | —H | —H | —OC(O)H | —H | —H | —CH$_3$ | —H | —CH$_3$ | —CH$_2$CH$_3$ | —CH$_3$ |
| 5 | —H | —H | —OC(O)H | —H | —H | —CH$_3$ | —H | —CH$_2$CH$_3$ | —CH$_3$ | —CH$_3$ |
| 6 | —H | —H | —OC(O)H | —H | —H | —CH$_3$ | —CH$_3$ | —H | —CH$_3$ | —CH$_3$ |
| 7 | —H | —H | —OC(O)H | —H | —H | —CH$_3$ | —CH$_3$ | —H | —CH$_2$CH$_3$ | —CH$_3$ |
| 8 | —H | —H | —OC(O)H | —H | —H | —CH$_3$ | —CH$_3$ | —CH$_3$ | —CH$_3$ | —CH$_3$ |
| 9 | —H | —H | —OC(O)H | —H | —H | —CH$_3$ | —CH$_3$ | —CH$_3$ | —CH$_2$CH$_3$ | —CH$_3$ |
| 10 | —H | —H | —OC(O)H | —H | —H | —CH$_3$ | —CH$_3$ | —CH$_2$CH$_3$ | —CH$_3$ | —CH$_3$ |
| 11 | —H | —H | —OC(O)H | —H | —H | —CH$_3$ | —CH$_2$CH$_3$ | —H | —CH$_3$ | —CH$_3$ |
| 12 | —H | —H | —OC(O)H | —H | —H | —CH$_3$ | —CH$_2$CH$_3$ | —CH$_3$ | —CH$_3$ | —CH$_3$ |
| 13 | —H | —H | —OC(O)H | —H | —H | —CH$_2$CH$_3$ | —H | —H | —CH$_3$ | —CH$_3$ |
| 14 | —H | —H | —OC(O)H | —H | —H | —CH$_2$CH$_3$ | —H | —CH$_3$ | —CH$_3$ | —CH$_3$ |
| 15 | —H | —H | —OC(O)H | —H | —H | —CH$_2$CH$_3$ | —CH$_3$ | —H | —CH$_3$ | —CH$_3$ |
| 16 | —H | —H | —OC(O)H | —H | —H | —CH$_2$CH$_3$ | —CH$_3$ | —CH$_3$ | —CH$_3$ | —CH$_3$ |
| 17 | —H | —H | —OC(O)H | —H | —CH$_3$ | —CH$_3$ | —H | —H | —CH$_3$ | —CH$_3$ |
| 18 | —H | —H | —OC(O)H | —H | —CH$_3$ | —CH$_3$ | —H | —H | —CH$_2$CH$_3$ | —CH$_3$ |
| 19 | —H | —H | —OC(O)H | —H | —CH$_3$ | —CH$_3$ | —H | —CH$_3$ | —CH$_3$ | —CH$_3$ |
| 20 | —H | —H | —OC(O)H | —H | —CH$_3$ | —CH$_3$ | —H | —CH$_3$ | —CH$_2$CH$_3$ | —CH$_3$ |
| 21 | —H | —H | —OC(O)H | —H | —CH$_3$ | —CH$_3$ | —H | —CH$_2$CH$_3$ | —CH$_3$ | —CH$_3$ |
| 22 | —H | —H | —OC(O)H | —H | —CH$_3$ | —CH$_3$ | —CH$_3$ | —H | —CH$_3$ | —CH$_3$ |
| 23 | —H | —H | —OC(O)H | —H | —CH$_3$ | —CH$_3$ | —CH$_3$ | —H | —CH$_2$CH$_3$ | —CH$_3$ |
| 24 | —H | —H | —OC(O)H | —H | —CH$_3$ | —CH$_3$ | —CH$_3$ | —CH$_3$ | —CH$_3$ | —CH$_3$ |
| 25 | —H | —H | —OC(O)H | —H | —CH$_3$ | —CH$_3$ | —CH$_3$ | —CH$_3$ | —CH$_2$CH$_3$ | —CH$_3$ |
| 26 | —H | —H | —OC(O)H | —H | —CH$_3$ | —CH$_3$ | —CH$_3$ | —CH$_2$CH$_3$ | —CH$_3$ | —CH$_3$ |
| 27 | —H | —H | —OC(O)H | —H | —CH$_3$ | —CH$_3$ | —CH$_2$CH$_3$ | —H | —CH$_3$ | —CH$_3$ |
| 28 | —H | —H | —OC(O)H | —H | —CH$_3$ | —CH$_3$ | —CH$_2$CH$_3$ | —CH$_3$ | —CH$_3$ | —CH$_3$ |
| 29 | —H | —H | —OC(O)H | —H | —CH$_3$ | —CH$_2$CH$_3$ | —H | —H | —CH$_3$ | —CH$_3$ |
| 30 | —H | —H | —OC(O)H | —H | —CH$_3$ | —CH$_2$CH$_3$ | —H | —CH$_3$ | —CH$_3$ | —CH$_3$ |
| 31 | —H | —H | —OC(O)H | —H | —CH$_3$ | —CH$_2$CH$_3$ | —CH$_3$ | —H | —CH$_3$ | —CH$_3$ |
| 32 | —H | —H | —OC(O)H | —H | —CH$_3$ | —CH$_2$CH$_3$ | —CH$_3$ | —CH$_3$ | —CH$_3$ | —CH$_3$ |
| 33 | —H | —H | —OC(O)H | —H | —CH$_3$ | —CH$_2$CH$_3$ | —H | —H | —CH$_3$ | —CH$_3$ |
| 34 | —H | —H | —OC(O)H | —H | —CH$_3$ | —CH$_2$CH$_3$ | —H | —CH$_3$ | —CH$_3$ | —CH$_3$ |
| 35 | —H | —H | —OC(O)H | —H | —CH$_3$ | —CH$_2$CH$_3$ | —CH$_3$ | —H | —CH$_3$ | —CH$_3$ |
| 36 | —H | —H | —OC(O)H | —H | —CH$_3$ | —CH$_2$CH$_3$ | —CH$_3$ | —CH$_3$ | —CH$_3$ | —CH$_3$ |
| 37 | —H | —H | —OC(O)H | —H | —CH$_3$ | —CH$_3$ | —H | —H | —H | —CH$_3$ |
| 38 | —H | —H | —OC(O)H | —H | —CH$_3$ | —CH$_2$CH$_3$ | —H | —H | —H | —CH$_3$ |
| 39 | —H | —H | —OC(O)H | —H | —CH$_3$ | —CH$_3$ | —H | —CH$_3$ | —H | —CH$_3$ |
| 40 | —H | —H | —OC(O)H | —H | —CH$_3$ | —CH$_2$CH$_3$ | —H | —CH$_3$ | —H | —CH$_3$ |
| 41 | —H | —H | —OC(O)H | —H | —CH$_3$ | —CH$_3$ | —H | —CH$_2$CH$_3$ | —H | —CH$_3$ |
| 42 | —H | —H | —OC(O)H | —H | —CH$_3$ | —CH$_3$ | —CH$_3$ | —H | —H | —CH$_3$ |
| 43 | —H | —H | —OC(O)H | —H | —CH$_3$ | —CH$_2$CH$_3$ | —CH$_3$ | —H | —H | —CH$_3$ |
| 44 | —H | —H | —OC(O)H | —H | —CH$_3$ | —CH$_3$ | —CH$_3$ | —CH$_3$ | —H | —CH$_3$ |
| 45 | —H | —H | —OC(O)H | —H | —CH$_3$ | —CH$_2$CH$_3$ | —CH$_3$ | —CH$_3$ | —H | —CH$_3$ |
| 46 | —H | —H | —OC(O)H | —H | —CH$_3$ | —CH$_3$ | —CH$_3$ | —CH$_2$CH$_3$ | —H | —CH$_3$ |
| 47 | —H | —H | —OC(O)H | —H | —CH$_3$ | —CH$_3$ | —CH$_2$CH$_3$ | —H | —H | —CH$_3$ |
| 48 | —H | —H | —OC(O)H | —H | —CH$_3$ | —CH$_3$ | —CH$_2$CH$_3$ | —CH$_3$ | —H | —CH$_3$ |
| 49 | —CH$_3$ | —H | —CO(O)H | —H | —H | —CH$_3$ | —H | —H | —CH$_3$ | —CH$_3$ |
| 50 | —CH$_3$ | —H | —CO(O)H | —H | —H | —CH$_3$ | —H | —H | —CH$_2$CH$_3$ | —CH$_3$ |
| 51 | —CH$_3$ | —H | —CO(O)H | —H | —H | —CH$_2$CH$_3$ | —H | —H | —CH$_3$ | —CH$_3$ |
| 52 | —CH$_3$ | —H | —CO(O)H | —H | —CH$_3$ | —CH$_3$ | —H | —H | —CH$_3$ | —CH$_3$ |
| 53 | —CH$_3$ | —H | —CO(O)H | —H | —CH$_3$ | —CH$_3$ | —H | —H | —CH$_2$CH$_3$ | —CH$_3$ |
| 54 | —CH$_3$ | —H | —CO(O)H | —H | —CH$_3$ | —CH$_2$CH$_3$ | —H | —H | —CH$_3$ | —CH$_3$ |
| 55 | —CH$_3$ | —H | —CO(O)H | —H | —CH$_3$ | —CH$_2$CH$_3$ | —H | —H | —CH$_3$ | —CH$_3$ |
| 56 | —CH$_3$ | —H | —CO(O)H | —H | —CH$_3$ | —CH$_3$ | —H | —H | —H | —CH$_3$ |
| 57 | —CH$_3$ | —H | —CO(O)H | —H | —CH$_3$ | —CH$_2$CH$_3$ | —H | —H | —H | —CH$_3$ |

TABLE I-continued

| # | | | | | | | | | |
|---|---|---|---|---|---|---|---|---|---|
| 58 | —CH$_2$CH$_3$ | —H | —OC(O)H | —H | —H | —CH$_3$ | —H | —H | —CH$_3$ | —CH$_3$ |
| 59 | —CH$_2$CH$_3$ | —H | —OC(O)H | —H | —H | —CH$_3$ | —H | —H | —CH$_2$CH$_3$ | —CH$_3$ |
| 60 | —CH$_2$CH$_3$ | —H | —OC(O)H | —H | —H | —CH$_2$CH$_3$ | —H | —H | —CH$_3$ | —CH$_3$ |
| 61 | —CH$_2$CH$_3$ | —H | —OC(O)H | —H | —CH$_3$ | —CH$_3$ | —H | —H | —CH$_3$ | —CH$_3$ |
| 62 | —CH$_2$CH$_3$ | —H | —OC(O)H | —H | —CH$_3$ | —CH$_3$ | —H | —H | —CH$_2$CH$_3$ | —CH$_3$ |
| 63 | —CH$_2$CH$_3$ | —H | —OC(O)H | —H | —CH$_3$ | —CH$_2$CH$_3$ | —H | —H | —CH$_3$ | —CH$_3$ |
| 64 | —CH$_2$CH$_3$ | —H | —OC(O)H | —H | —CH$_3$ | —CH$_2$CH$_3$ | —H | —H | —CH$_3$ | —CH$_3$ |
| 65 | —CH$_2$CH$_3$ | —H | —OC(O)H | —H | —CH$_3$ | —CH$_3$ | —H | —H | —H | —CH$_3$ |
| 66 | —CH$_2$CH$_3$ | —H | —OC(O)H | —H | —CH$_3$ | —CH$_2$CH$_3$ | —H | —H | —H | —CH$_3$ |
| 67 | —H | —CH$_3$ | —OC(O)H | —H | —H | —CH$_3$ | —H | —H | —CH$_3$ | —CH$_3$ |
| 68 | —H | —CH$_3$ | —OC(O)H | —H | —H | —CH$_3$ | —H | —H | —CH$_2$CH$_3$ | —CH$_3$ |
| 69 | —H | —CH$_3$ | —OC(O)H | —H | —H | —CH$_3$ | —H | —CH$_3$ | —CH$_3$ | —CH$_3$ |
| 70 | —H | —CH$_3$ | —OC(O)H | —H | —H | —CH$_3$ | —H | —CH$_3$ | —CH$_2$CH$_3$ | —CH$_3$ |
| 71 | —H | —CH$_3$ | —OC(O)H | —H | —H | —CH$_3$ | —H | —CH$_2$CH$_3$ | —CH$_3$ | —CH$_3$ |
| 72 | —H | —CH$_3$ | —OC(O)H | —H | —H | —CH$_3$ | —CH$_3$ | —H | —CH$_3$ | —CH$_3$ |
| 73 | —H | —CH$_3$ | —OC(O)H | —H | —H | —CH$_3$ | —CH$_3$ | —H | —CH$_2$CH$_3$ | —CH$_3$ |
| 74 | —H | —CH$_3$ | —OC(O)H | —H | —H | —CH$_3$ | —CH$_3$ | —CH$_3$ | —CH$_3$ | —CH$_3$ |
| 75 | —H | —CH$_3$ | —OC(O)H | —H | —H | —CH$_3$ | —CH$_3$ | —CH$_3$ | —CH$_2$CH$_3$ | —CH$_3$ |
| 76 | —H | —CH$_3$ | —OC(O)H | —H | —H | —CH$_3$ | —CH$_3$ | —CH$_2$CH$_3$ | —CH$_3$ | —CH$_3$ |
| 77 | —H | —CH$_3$ | —OC(O)H | —H | —H | —CH$_3$ | —CH$_2$CH$_3$ | —H | —CH$_3$ | —CH$_3$ |
| 78 | —H | —CH$_3$ | —OC(O)H | —H | —H | —CH$_3$ | —CH$_2$CH$_3$ | —CH$_3$ | —CH$_3$ | —CH$_3$ |
| 79 | —H | —CH$_3$ | —OC(O)H | —H | —H | —CH$_2$CH$_3$ | —H | —H | —CH$_3$ | —CH$_3$ |
| 80 | —H | —CH$_3$ | —OC(O)H | —H | —H | —CH$_2$CH$_3$ | —H | —CH$_3$ | —CH$_3$ | —CH$_3$ |
| 81 | —H | —CH$_3$ | —OC(O)H | —H | —H | —CH$_2$CH$_3$ | —CH$_3$ | —H | —CH$_3$ | —CH$_3$ |
| 82 | —H | —CH$_3$ | —OC(O)H | —H | —H | —CH$_2$CH$_3$ | —CH$_3$ | —CH$_3$ | —CH$_3$ | —CH$_3$ |
| 83 | —H | —CH$_3$ | —OC(O)H) | —H | —CH$_3$ | —CH$_3$ | —H | —H | —CH$_3$ | —CH$_3$ |
| 84 | —H | —CH$_3$ | —OC(O)H) | —H | —CH$_3$ | —CH$_3$ | —H | —H | —CH$_2$CH$_3$ | —CH$_3$ |
| 85 | —H | —CH$_3$ | —OC(O)H) | —H | —CH$_3$ | —CH$_3$ | —H | —CH$_3$ | —CH$_3$ | —CH$_3$ |
| 86 | —H | —CH$_3$ | —OC(O)H) | —H | —CH$_3$ | —CH$_3$ | —H | —CH$_3$ | —CH$_2$CH$_3$ | —CH$_3$ |
| 87 | —H | —CH$_3$ | —OC(O)H) | —H | —CH$_3$ | —CH$_3$ | —H | —CH$_2$CH$_3$ | —CH$_3$ | —CH$_3$ |
| 88 | —H | —CH$_3$ | —OC(O)H) | —H | —CH$_3$ | —CH$_3$ | —CH$_3$ | —H | —CH$_3$ | —CH$_3$ |
| 89 | —H | —CH$_3$ | —OC(O)H) | —H | —CH$_3$ | —CH$_3$ | —CH$_3$ | —H | —CH$_2$CH$_3$ | —CH$_3$ |
| 90 | —H | —CH$_3$ | —OC(O)H) | —H | —CH$_3$ | —CH$_3$ | —CH$_3$ | —CH$_3$ | —CH$_3$ | —CH$_3$ |
| 91 | —H | —CH$_3$ | —OC(O)H) | —H | —CH$_3$ | —CH$_3$ | —CH$_3$ | —CH$_3$ | —CH$_2$CH$_3$ | —CH$_3$ |
| 92 | —H | —CH$_3$ | —OC(O)H) | —H | —CH$_3$ | —CH$_3$ | —CH$_3$ | —CH$_2$CH$_3$ | —CH$_3$ | —CH$_3$ |
| 93 | —H | —CH$_3$ | —OC(O)H) | —H | —CH$_3$ | —CH$_3$ | —CH$_2$CH$_3$ | —H | —CH$_3$ | —CH$_3$ |
| 94 | —H | —CH$_3$ | —OC(O)H) | —H | —CH$_3$ | —CH$_3$ | —CH$_2$CH$_3$ | —CH$_3$ | —CH$_3$ | —CH$_3$ |
| 95 | —H | —CH$_3$ | —OC(O)H) | —H | —CH$_3$ | —CH$_2$CH$_3$ | —H | —H | —CH$_3$ | —CH$_3$ |
| 96 | —H | —CH$_3$ | —OC(O)H) | —H | —CH$_3$ | —CH$_2$CH$_3$ | —H | —CH$_3$ | —CH$_3$ | —CH$_3$ |
| 97 | —H | —CH$_3$ | —OC(O)H) | —H | —CH$_3$ | —CH$_2$CH$_3$ | —H | —CH$_3$ | —CH$_3$ | —CH$_3$ |
| 98 | —H | —CH$_3$ | —OC(O)H) | —H | —CH$_3$ | —CH$_2$CH$_3$ | —CH$_3$ | —CH$_3$ | —CH$_3$ | —CH$_3$ |
| 99 | —H | —CH$_3$ | —OC(O)H) | —H | —CH$_3$ | —CH$_2$CH$_3$ | —H | —H | —CH$_3$ | —CH$_3$ |
| 100 | —H | —CH$_3$ | —OC(O)H) | —H | —CH$_3$ | —CH$_2$CH$_3$ | —H | —CH$_3$ | —CH$_3$ | —CH$_3$ |
| 101 | —H | —CH$_3$ | —OC(O)H) | —H | —CH$_3$ | —CH$_2$CH$_3$ | —H | —CH$_3$ | —CH$_3$ | —CH$_3$ |
| 102 | —H | —CH$_3$ | —OC(O)H) | —H | —CH$_3$ | —CH$_2$CH$_3$ | —CH$_3$ | —CH$_3$ | —CH$_3$ | —CH$_3$ |
| 103 | —H | —CH$_3$ | —OC(O)H) | —H | —CH$_3$ | —CH$_3$ | —H | —H | —H | —CH$_3$ |
| 104 | —H | —CH$_3$ | —OC(O)H) | —H | —CH$_3$ | —CH$_2$CH$_3$ | —H | —H | —H | —CH$_3$ |
| 105 | —H | —CH$_3$ | —OC(O)H) | —H | —CH$_3$ | —CH$_3$ | —H | —CH$_3$ | —H | —CH$_3$ |
| 106 | —H | —CH$_3$ | —OC(O)H) | —H | —CH$_3$ | —CH$_2$CH$_3$ | —H | —CH$_3$ | —H | —CH$_3$ |
| 107 | —H | —CH$_3$ | —OC(O)H) | —H | —CH$_3$ | —CH$_3$ | —H | —CH$_2$CH$_3$ | —H | —CH$_3$ |
| 108 | —H | —CH$_3$ | —OC(O)H) | —H | —CH$_3$ | —CH$_3$ | —CH$_3$ | —H | —H | —CH$_3$ |
| 109 | —H | —CH$_3$ | —OC(O)H) | —H | —CH$_3$ | —CH$_2$CH$_3$ | —CH$_3$ | —H | —H | —CH$_3$ |
| 110 | —H | —CH$_3$ | —OC(O)H) | —H | —CH$_3$ | —CH$_3$ | —CH$_3$ | —CH$_3$ | —H | —CH$_3$ |
| 111 | —H | —CH$_3$ | —OC(O)H) | —H | —CH$_3$ | —CH$_2$CH$_3$ | —CH$_3$ | —CH$_3$ | —H | —CH$_3$ |
| 112 | —H | —CH$_3$ | —OC(O)H) | —H | —CH$_3$ | —CH$_3$ | —CH$_3$ | —CH$_2$CH$_3$ | —H | —CH$_3$ |
| 113 | —H | —CH$_3$ | —OC(O)H) | —H | —CH$_3$ | —CH$_3$ | —CH$_2$CH$_3$ | —H | —H | —CH$_3$ |
| 114 | —H | —CH$_3$ | —OC(O)H) | —H | —CH$_3$ | —CH$_3$ | —CH$_2$CH$_3$ | —CH$_3$ | —H | —CH$_3$ |
| 115 | —CH$_3$ | —CH$_3$ | —OC(O)H) | —H | —H | —CH$_3$ | —H | —H | —CH$_3$ | —CH$_3$ |
| 116 | —CH$_3$ | —CH$_3$ | —OC(O)H) | —H | —H | —CH$_3$ | —H | —H | —CH$_2$CH$_3$ | —CH$_3$ |
| 117 | —CH$_3$ | —CH$_3$ | —OC(O)H) | —H | —H | —CH$_3$ | —H | —CH$_3$ | —CH$_3$ | —CH$_3$ |
| 118 | —CH$_3$ | —CH$_3$ | —OC(O)H) | —H | —H | —CH$_2$CH$_3$ | —H | —H | —CH$_3$ | —CH$_3$ |
| 119 | —CH$_3$ | —CH$_3$ | —OC(O)H) | —H | —CH$_3$ | —CH$_3$ | —H | —H | —CH$_3$ | —CH$_3$ |
| 120 | —CH$_3$ | —CH$_3$ | —OC(O)H) | —H | —CH$_3$ | —CH$_3$ | —H | —H | —CH$_2$CH$_3$ | —CH$_3$ |
| 121 | —CH$_3$ | —CH$_3$ | —OC(O)H) | —H | —CH$_3$ | —CH$_2$CH$_3$ | —H | —H | —CH$_3$ | —CH$_3$ |
| 122 | —CH$_3$ | —CH$_3$ | —OC(O)H) | —H | —CH$_3$ | —CH$_2$CH$_3$ | —H | —H | —CH$_3$ | —CH$_3$ |
| 123 | —CH$_3$ | —CH$_3$ | —OC(O)H) | —H | —CH$_3$ | —CH$_3$ | —H | —H | —H | —CH$_3$ |
| 124 | —CH$_3$ | —CH$_3$ | —OC(O)H) | —H | —CH$_3$ | —CH$_2$CH$_3$ | —H | —H | —H | —CH$_3$ |
| 125 | —CH$_2$CH$_3$ | —CH$_3$ | —OC(O)H) | —H | —H | —CH$_3$ | —H | —H | —CH$_3$ | —CH$_3$ |
| 126 | —CH$_2$CH$_3$ | —CH$_3$ | —OC(O)H) | —H | —H | —CH$_3$ | —H | —H | —CH$_2$CH$_3$ | —CH$_3$ |
| 127 | —CH$_2$CH$_3$ | —CH$_3$ | —OC(O)H) | —H | —H | —CH$_2$CH$_3$ | —H | —H | —CH$_3$ | —CH$_3$ |
| 128 | —CH$_2$CH$_3$ | —CH$_3$ | —OC(O)H) | —H | —CH$_3$ | —CH$_3$ | —H | —H | —CH$_3$ | —CH$_3$ |
| 129 | —CH$_2$CH$_3$ | —CH$_3$ | —OC(O)H) | —H | —CH$_3$ | —CH$_3$ | —H | —H | —CH$_2$CH$_3$ | —CH$_3$ |
| 130 | —CH$_2$CH$_3$ | —CH$_3$ | —OC(O)H) | —H | —CH$_3$ | —CH$_2$CH$_3$ | —H | —H | —CH$_3$ | —CH$_3$ |
| 131 | —CH$_2$CH$_3$ | —CH$_3$ | —OC(O)H) | —H | —CH$_3$ | —CH$_2$CH$_3$ | —H | —H | —CH$_3$ | —CH$_3$ |
| 132 | —CH$_2$CH$_3$ | —CH$_3$ | —OC(O)H) | —H | —CH$_3$ | —CH$_3$ | —H | —H | —H | —CH$_3$ |
| 133 | —CH$_2$CH$_3$ | —CH$_3$ | —OC(O)H) | —H | —CH$_3$ | —CH$_2$CH$_3$ | —H | —H | —H | —CH$_3$ |
| 134 | —H | —CH$_2$CH$_3$ | —OC(O)H) | —H | —H | —CH$_3$ | —H | —H | —CH$_3$ | —CH$_3$ |
| 135 | —H | —CH$_2$CH$_3$ | —OC(O)H) | —H | —H | —CH$_3$ | —H | —H | —CH$_2$CH$_3$ | —CH$_3$ |
| 136 | —H | —CH$_2$CH$_3$ | —OC(O)H) | —H | —H | —CH$_3$ | —H | —CH$_3$ | —CH$_3$ | —CH$_3$ |
| 137 | —H | —CH$_2$CH$_3$ | —OC(O)H) | —H | —H | —CH$_3$ | —H | —CH$_3$ | —CH$_2$CH$_3$ | —CH$_3$ |
| 138 | —H | —CH$_2$CH$_3$ | —OC(O)H) | —H | —H | —CH$_3$ | —H | —CH$_2$CH$_3$ | —CH$_3$ | —CH$_3$ |
| 139 | —H | —CH$_2$CH$_3$ | —OC(O)H) | —H | —H | —CH$_3$ | —CH$_3$ | —H | —CH$_3$ | —CH$_3$ |

TABLE I-continued

| | | | | | | | | | | |
|---|---|---|---|---|---|---|---|---|---|---|
| 140 | —H | —CH₂CH₃ | —OC(O)H | —H | —H | —CH₃ | —CH₃ | —H | —CH₂CH₃ | —CH₃ |
| 141 | —H | —CH₂CH₃ | —OC(O)H | —H | —H | —CH₃ | —CH₃ | —CH₃ | —CH₃ | —CH₃ |
| 142 | —H | —CH₂CH₃ | —OC(O)H | —H | —H | —CH₃ | —CH₃ | —CH₃ | —CH₂CH₃ | —CH₃ |
| 143 | —H | —CH₂CH₃ | —OC(O)H | —H | —H | —CH₃ | —CH₃ | —CH₂CH₃ | —CH₃ | —CH₃ |
| 144 | —H | —CH₂CH₃ | —OC(O)H | —H | —H | —CH₃ | —CH₂CH₃ | —H | —CH₃ | —CH₃ |
| 145 | —H | —CH₂CH₃ | —OC(O)H | —H | —H | —CH₃ | —CH₂CH₃ | —CH₃ | —CH₃ | —CH₃ |
| 146 | —H | —CH₂CH₃ | —OC(O)H | —H | —H | —CH₂CH₃ | —CH₃ | —H | —CH₃ | —CH₃ |
| 147 | —H | —CH₂CH₃ | —OC(O)H | —H | —H | —CH₂CH₃ | —H | —CH₃ | —CH₃ | —CH₃ |
| 148 | —H | —CH₂CH₃ | —OC(O)H | —H | —H | —CH₂CH₃ | —CH₃ | —H | —CH₃ | —CH₃ |
| 149 | —H | —CH₂CH₃ | —OC(O)H | —H | —H | —CH₂CH₃ | —CH₃ | —CH₃ | —CH₃ | —CH₃ |
| 150 | —H | —CH₂CH₃ | —OC(O)H | —H | —CH₃ | —CH₃ | —H | —H | —CH₃ | —CH₃ |
| 151 | —H | —CH₂CH₃ | —OC(O)H | —H | —CH₃ | —CH₃ | —H | —H | —CH₂CH₃ | —CH₃ |
| 152 | —H | —CH₂CH₃ | —OC(O)H | —H | —CH₃ | —CH₃ | —H | —CH₃ | —CH₃ | —CH₃ |
| 153 | —H | —CH₂CH₃ | —OC(O)H | —H | —CH₃ | —CH₃ | —H | —CH₃ | —CH₂CH₃ | —CH₃ |
| 154 | —H | —CH₂CH₃ | —OC(O)H | —H | —CH₃ | —CH₃ | —H | —CH₂CH₃ | —CH₃ | —CH₃ |
| 155 | —H | —CH₂CH₃ | —OC(O)H | —H | —CH₃ | —CH₃ | —CH₃ | —H | —CH₃ | —CH₃ |
| 156 | —H | —CH₂CH₃ | —OC(O)H | —H | —CH₃ | —CH₃ | —CH₃ | —H | —CH₂CH₃ | —CH₃ |
| 157 | —H | —CH₂CH₃ | —OC(O)H | —H | —CH₃ | —CH₃ | —CH₃ | —CH₃ | —CH₃ | —CH₃ |
| 158 | —H | —CH₂CH₃ | —OC(O)H | —H | —CH₃ | —CH₃ | —CH₃ | —CH₃ | —CH₂CH₃ | —CH₃ |
| 159 | —H | —CH₂CH₃ | —OC(O)H | —H | —CH₃ | —CH₃ | —CH₃ | —CH₂CH₃ | —CH₃ | —CH₃ |
| 160 | —H | —CH₂CH₃ | —OC(O)H | —H | —CH₃ | —CH₃ | —CH₂CH₃ | —H | —CH₃ | —CH₃ |
| 161 | —H | —CH₂CH₃ | —OC(O)H | —H | —CH₃ | —CH₃ | —CH₂CH₃ | —CH₃ | —CH₃ | —CH₃ |
| 162 | —H | —CH₂CH₃ | —OC(O)H | —H | —CH₃ | —CH₂CH₃ | —H | —H | —CH₃ | —CH₃ |
| 163 | —H | —CH₂CH₃ | —OC(O)H | —H | —CH₃ | —CH₂CH₃ | —H | —CH₃ | —CH₃ | —CH₃ |
| 164 | —H | —CH₂CH₃ | —OC(O)H | —H | —CH₃ | —CH₂CH₃ | —CH₃ | —H | —CH₃ | —CH₃ |
| 165 | —H | —CH₂CH₃ | —OC(O)H | —H | —CH₃ | —CH₂CH₃ | —CH₃ | —CH₃ | —CH₃ | —CH₃ |
| 166 | —H | —CH₂CH₃ | —OC(O)H | —H | —CH₃ | —CH₂CH₃ | —H | —H | —CH₃ | —CH₃ |
| 167 | —H | —CH₂CH₃ | —OC(O)H | —H | —CH₃ | —CH₂CH₃ | —H | —CH₃ | —CH₃ | —CH₃ |
| 168 | —H | —CH₂CH₃ | —OC(O)H | —H | —CH₃ | —CH₂CH₃ | —CH₃ | —H | —CH₃ | —CH₃ |
| 169 | —H | —CH₂CH₃ | —OC(O)H | —H | —CH₃ | —CH₂CH₃ | —CH₃ | —CH₃ | —CH₃ | —CH₃ |
| 170 | —H | —CH₂CH₃ | —OC(O)H | —H | —CH₃ | —CH₃ | —H | —H | —H | —CH₃ |
| 171 | —H | —CH₂CH₃ | —OC(O)H | —H | —CH₃ | —CH₂CH₃ | —H | —H | —H | —CH₃ |
| 172 | —H | —CH₂CH₃ | —OC(O)H | —H | —CH₃ | —CH₃ | —H | —CH₃ | —H | —CH₃ |
| 173 | —H | —CH₂CH₃ | —OC(O)H | —H | —CH₃ | —CH₂CH₃ | —H | —CH₃ | —H | —CH₃ |
| 174 | —H | —CH₂CH₃ | —OC(O)H | —H | —CH₃ | —CH₃ | —H | —CH₂CH₃ | —H | —CH₃ |
| 175 | —H | —CH₂CH₃ | —OC(O)H | —H | —CH₃ | —CH₃ | —CH₃ | —H | —H | —CH₃ |
| 176 | —H | —CH₂CH₃ | —OC(O)H | —H | —CH₃ | —CH₂CH₃ | —CH₃ | —H | —H | —CH₃ |
| 177 | —H | —CH₂CH₃ | —OC(O)H | —H | —CH₃ | —CH₃ | —CH₃ | —CH₃ | —H | —CH₃ |
| 178 | —H | —CH₂CH₃ | —OC(O)H | —H | —CH₃ | —CH₂CH₃ | —CH₃ | —CH₃ | —H | —CH₃ |
| 179 | —H | —CH₂CH₃ | —OC(O)H | —H | —CH₃ | —CH₃ | —CH₃ | —CH₂CH₃ | —H | —CH₃ |
| 180 | —H | —CH₂CH₃ | —OC(O)H | —H | —CH₃ | —CH₃ | —CH₂CH₃ | —H | —H | —CH₃ |
| 181 | —H | —CH₂CH₃ | —OC(O)H | —H | —CH₃ | —CH₃ | —CH₂CH₃ | —CH₃ | —H | —CH₃ |
| 182 | —CH₃ | —CH₂CH₃ | —OC(O)H | —H | —H | —CH₃ | —H | —H | —CH₃ | —CH₃ |
| 183 | —CH₃ | —CH₂CH₃ | —OC(O)H | —H | —H | —CH₃ | —H | —H | —CH₂CH₃ | —CH₃ |
| 184 | —CH₃ | —CH₂CH₃ | —OC(O)H | —H | —H | —CH₂CH₃ | —H | —H | —CH₃ | —CH₃ |
| 185 | —CH₃ | —CH₂CH₃ | —OC(O)H | —H | —CH₃ | —CH₃ | —H | —H | —CH₃ | —CH₃ |
| 186 | —CH₃ | —CH₂CH₃ | —OC(O)H | —H | —CH₃ | —CH₃ | —H | —H | —CH₂CH₃ | —CH₃ |
| 187 | —CH₃ | —CH₂CH₃ | —OC(O)H | —H | —CH₃ | —CH₂CH₃ | —H | —H | —CH₃ | —CH₃ |
| 188 | —CH₃ | —CH₂CH₃ | —OC(O)H | —H | —CH₃ | —CH₂CH₃ | —H | —H | —CH₃ | —CH₃ |
| 189 | —CH₃ | —CH₂CH₃ | —OC(O)H | —H | —CH₃ | —CH₃ | —H | —H | —H | —CH₃ |
| 190 | —CH₃ | —CH₂CH₃ | —OC(O)H | —H | —CH₃ | —CH₂CH₃ | —H | —H | —H | —CH₃ |
| 191 | —CH₂CH₃ | —CH₂CH₃ | —OC(O)H | —H | —H | —CH₃ | —H | —H | —CH₃ | —CH₃ |
| 192 | —CH₂CH₃ | —CH₂CH₃ | —OC(O)H | —H | —H | —CH₃ | —H | —H | —CH₂CH₃ | —CH₃ |
| 193 | —CH₂CH₃ | —CH₂CH₃ | —OC(O)H | —H | —H | —CH₂CH₃ | —H | —H | —CH₃ | —CH₃ |
| 194 | —CH₂CH₃ | —CH₂CH₃ | —OC(O)H | —H | —CH₃ | —CH₃ | —H | —H | —CH₃ | —CH₃ |
| 195 | —CH₂CH₃ | —CH₂CH₃ | —OC(O)H | —H | —CH₃ | —CH₃ | —H | —H | —CH₂CH₃ | —CH₃ |
| 196 | —CH₂CH₃ | —CH₂CH₃ | —OC(O)H | —H | —CH₃ | —CH₂CH₃ | —H | —H | —CH₃ | —CH₃ |
| 197 | —CH₂CH₃ | —CH₂CH₃ | —OC(O)H | —H | —CH₃ | —CH₂CH₃ | —H | —H | —CH₃ | —CH₃ |
| 198 | —CH₂CH₃ | —CH₂CH₃ | —OC(O)H | —H | —CH₃ | —CH₃ | —H | —H | —H | —CH₃ |
| 199 | —CH₂CH₃ | —CH₂CH₃ | —OC(O)H | —H | —CH₃ | —CH₂CH₃ | —H | —H | —H | —CH₃ |
| 200 | —CH₃ | —OCH₃ | —OC(O)H | —H | —H | —CH₃ | —H | —H | —CH₃ | —CH₃ |
| 201 | —CH₃ | —OCH₃ | —OC(O)H | —H | —H | —CH₃ | —H | —H | —CH₂CH₃ | —CH₃ |
| 202 | —CH₃ | —OCH₃ | —OC(O)H | —H | —H | —CH₂CH₃ | —H | —H | —CH₃ | —CH₃ |
| 203 | —CH₃ | —OCH₃ | —OC(O)H | —H | —CH₃ | —CH₃ | —H | —H | —CH₃ | —CH₃ |
| 204 | —CH₃ | —OCH₃ | —OC(O)H | —H | —CH₃ | —CH₃ | —H | —H | —CH₂CH₃ | —CH₃ |
| 205 | —CH₃ | —OCH₃ | —OC(O)H | —H | —CH₃ | —CH₂CH₃ | —H | —H | —CH₃ | —CH₃ |
| 206 | —CH₃ | —OCH₃ | —OC(O)H | —H | —CH₃ | —CH₂CH₃ | —H | —H | —CH₃ | —CH₃ |
| 207 | —CH₃ | —OCH₃ | —OC(O)H | —H | —CH₃ | —CH₃ | —H | —H | —H | —CH₃ |
| 208 | —CH₃ | —OCH₃ | —OC(O)H | —H | —CH₃ | —CH₂CH₃ | —H | —H | —H | —CH₃ |
| 209 | —CH₂CH₃ | —OCH₃ | —OC(O)H | —H | —H | —CH₃ | —H | —H | —CH₃ | —CH₃ |
| 210 | —CH₂CH₃ | —OCH₃ | —OC(O)H | —H | —H | —CH₃ | —H | —H | —CH₂CH₃ | —CH₃ |
| 211 | —CH₂CH₃ | —OCH₃ | —OC(O)H | —H | —H | —CH₂CH₃ | —H | —H | —CH₃ | —CH₃ |
| 212 | —CH₂CH₃ | —OCH₃ | —OC(O)H | —H | —CH₃ | —CH₃ | —H | —H | —CH₃ | —CH₃ |
| 213 | —CH₂CH₃ | —OCH₃ | —OC(O)H | —H | —CH₃ | —CH₃ | —H | —H | —CH₂CH₃ | —CH₃ |
| 214 | —CH₂CH₃ | —OCH₃ | —OC(O)H | —H | —CH₃ | —CH₂CH₃ | —H | —H | —CH₃ | —CH₃ |
| 215 | —CH₂CH₃ | —OCH₃ | —OC(O)H | —H | —CH₃ | —CH₂CH₃ | —H | —H | —CH₃ | —CH₃ |
| 216 | —CH₂CH₃ | —OCH₃ | —OC(O)H | —H | —CH₃ | —CH₃ | —H | —H | —H | —CH₃ |
| 217 | —CH₂CH₃ | —OCH₃ | —OC(O)H | —H | —CH₃ | —CH₂CH₃ | —H | —H | —H | —CH₃ |
| 218 | —CH₃ | —OH | —OC(O)H | —H | —H | —CH₃ | —H | —H | —CH₃ | —CH₃ |
| 219 | —CH₃ | —OH | —OC(O)H | —H | —H | —CH₃ | —H | —H | —CH₂CH₃ | —CH₃ |
| 220 | —CH₃ | —OH | —OC(O)H | —H | —H | —CH₂CH₃ | —H | —H | —CH₃ | —CH₃ |
| 221 | —CH₃ | —OH | —OC(O)H | —H | —CH₃ | —CH₃ | —H | —H | —CH₃ | —CH₃ |

TABLE I-continued

| | | | | | | | | | | |
|---|---|---|---|---|---|---|---|---|---|---|
| 222 | —CH₃ | —OH | —OC(O)H | —H | —CH₃ | —CH₃ | —H | —H | —CH₂CH₃ | —CH₃ |
| 223 | —CH₃ | —OH | —OC(O)H | —H | —CH₃ | —CH₂CH₃ | —H | —H | —CH₃ | —CH₃ |
| 224 | —CH₃ | —OH | —OC(O)H | —H | —CH₃ | —CH₂CH₃ | —H | —H | —CH₃ | —CH₃ |
| 225 | —CH₃ | —OH | —OC(O)H | —H | —CH₃ | —CH₃ | —H | —H | —H | —CH₃ |
| 226 | —CH₃ | —OH | —OC(O)H | —H | —CH₃ | —CH₂CH₃ | —H | —H | —H | —CH₃ |
| 227 | —CH₂CH₃ | —OH | —OC(O)H | —H | —H | —CH₃ | —H | —H | —CH₃ | —CH₃ |
| 228 | —CH₂CH₃ | —OH | —OC(O)H | —H | —H | —CH₃ | —H | —H | —CH₂CH₃ | —CH₃ |
| 229 | —CH₂CH₃ | —OH | —OC(O)H | —H | —H | —CH₂CH₃ | —H | —H | —CH₃ | —CH₃ |
| 230 | —CH₂CH₃ | —OH | —OC(O)H | —H | —CH₃ | —CH₃ | —H | —H | —CH₃ | —CH₃ |
| 231 | —CH₂CH₃ | —OH | —OC(O)H | —H | —CH₃ | —CH₃ | —H | —H | —CH₂CH₃ | —CH₃ |
| 232 | —CH₂CH₃ | —OH | —OC(O)H | —H | —CH₃ | —CH₂CH₃ | —H | —H | —CH₃ | —CH₃ |
| 233 | —CH₂CH₃ | —OH | —OC(O)H | —H | —CH₃ | —CH₂CH₃ | —H | —H | —CH₃ | —CH₃ |
| 234 | —CH₂CH₃ | —OH | —OC(O)H | —H | —CH₃ | —CH₃ | —H | —H | —H | —CH₃ |
| 235 | —CH₂CH₃ | —OH | —OC(O)H | —H | —CH₃ | —CH₂CH₃ | —H | —H | —H | —CH₃ |
| 236 | —OCH₃ | —CH₃ | —OC(O)H | —H | —H | —CH₃ | —H | —H | —CH₃ | —CH₃ |
| 237 | —OCH₃ | —CH₃ | —OC(O)H | —H | —H | —CH₃ | —H | —H | —CH₂CH₃ | —CH₃ |
| 238 | —OCH₃ | —CH₃ | —OC(O)H | —H | —H | —CH₃ | —H | —CH₃ | —CH₃ | —CH₃ |
| 239 | —OCH₃ | —CH₃ | —OC(O)H | —H | —H | —CH₃ | —H | —CH₃ | —CH₂CH₃ | —CH₃ |
| 240 | —OCH₃ | —CH₃ | —OC(O)H | —H | —H | —CH₃ | —H | —CH₂CH₃ | —CH₃ | —CH₃ |
| 241 | —OCH₃ | —CH₃ | —OC(O)H | —H | —H | —CH₃ | —CH₃ | —H | —CH₃ | —CH₃ |
| 242 | —OCH₃ | —CH₃ | —OC(O)H | —H | —H | —CH₃ | —CH₃ | —H | —CH₂CH₃ | —CH₃ |
| 243 | —OCH₃ | —CH₃ | —OC(O)H | —H | —H | —CH₃ | —CH₃ | —CH₃ | —CH₃ | —CH₃ |
| 244 | —OCH₃ | —CH₃ | —OC(O)H | —H | —H | —CH₃ | —CH₃ | —CH₃ | —CH₂CH₃ | —CH₃ |
| 245 | —OCH₃ | —CH₃ | —OC(O)H | —H | —H | —CH₃ | —CH₃ | —CH₂CH₃ | —CH₃ | —CH₃ |
| 246 | —OCH₃ | —CH₃ | —OC(O)H | —H | —H | —CH₃ | —CH₂CH₃ | —H | —CH₃ | —CH₃ |
| 247 | —OCH₃ | —CH₃ | —OC(O)H | —H | —H | —CH₃ | —CH₂CH₃ | —CH₃ | —CH₃ | —CH₃ |
| 248 | —OCH₃ | —CH₃ | —OC(O)H | —H | —H | —CH₂CH₃ | —H | —H | —CH₃ | —CH₃ |
| 249 | —OCH₃ | —CH₃ | —OC(O)H | —H | —H | —CH₂CH₃ | —H | —CH₃ | —CH₃ | —CH₃ |
| 250 | —OCH₃ | —CH₃ | —OC(O)H | —H | —H | —CH₂CH₃ | —CH₃ | —H | —CH₃ | —CH₃ |
| 251 | —OCH₃ | —CH₃ | —OC(O)H | —H | —H | —CH₂CH₃ | —CH₃ | —CH₃ | —CH₃ | —CH₃ |
| 252 | —OCH₃ | —CH₃ | —OC(O)H | —H | —CH₃ | —CH₃ | —H | —H | —CH₃ | —CH₃ |
| 253 | —OCH₃ | —CH₃ | —OC(O)H | —H | —CH₃ | —CH₃ | —H | —H | —CH₂CH₃ | —CH₃ |
| 254 | —OCH₃ | —CH₃ | —OC(O)H | —H | —CH₃ | —CH₃ | —H | —CH₃ | —CH₃ | —CH₃ |
| 255 | —OCH₃ | —CH₃ | —OC(O)H | —H | —CH₃ | —CH₃ | —H | —CH₃ | —CH₂CH₃ | —CH₃ |
| 256 | —OCH₃ | —CH₃ | —OC(O)H | —H | —CH₃ | —CH₃ | —H | —CH₂CH₃ | —CH₃ | —CH₃ |
| 257 | —OCH₃ | —CH₃ | —OC(O)H | —H | —CH₃ | —CH₃ | —CH₃ | —H | —CH₃ | —CH₃ |
| 258 | —OCH₃ | —CH₃ | —OC(O)H | —H | —CH₃ | —CH₃ | —CH₃ | —H | —CH₂CH₃ | —CH₃ |
| 259 | —OCH₃ | —CH₃ | —OC(O)H | —H | —CH₃ | —CH₃ | —CH₃ | —CH₃ | —CH₃ | —CH₃ |
| 260 | —OCH₃ | —CH₃ | —OC(O)H | —H | —CH₃ | —CH₃ | —CH₃ | —CH₃ | —CH₂CH₃ | —CH₃ |
| 261 | —OCH₃ | —CH₃ | —OC(O)H | —H | —CH₃ | —CH₃ | —CH₃ | —CH₂CH₃ | —CH₃ | —CH₃ |
| 262 | —OCH₃ | —CH₃ | —OC(O)H | —H | —CH₃ | —CH₃ | —CH₂CH₃ | —H | —CH₃ | —CH₃ |
| 263 | —OCH₃ | —CH₃ | —OC(O)H | —H | —CH₃ | —CH₃ | —CH₂CH₃ | —CH₃ | —CH₃ | —CH₃ |
| 264 | —OCH₃ | —CH₃ | —OC(O)H | —H | —CH₃ | —CH₂CH₃ | —H | —H | —CH₃ | —CH₃ |
| 265 | —OCH₃ | —CH₃ | —OC(O)H | —H | —CH₃ | —CH₂CH₃ | —H | —CH₃ | —CH₃ | —CH₃ |
| 266 | —OCH₃ | —CH₃ | —OC(O)H | —H | —CH₃ | —CH₂CH₃ | —CH₃ | —H | —CH₃ | —CH₃ |
| 267 | —OCH₃ | —CH₃ | —OC(O)H | —H | —CH₃ | —CH₂CH₃ | —CH₃ | —CH₃ | —CH₃ | —CH₃ |
| 268 | —OCH₃ | —CH₃ | —OC(O)H | —H | —CH₃ | —CH₂CH₃ | —H | —H | —CH₃ | —CH₃ |
| 269 | —OCH₃ | —CH₃ | —OC(O)H | —H | —CH₃ | —CH₂CH₃ | —H | —CH₃ | —CH₃ | —CH₃ |
| 270 | —OCH₃ | —CH₃ | —OC(O)H | —H | —CH₃ | —CH₂CH₃ | —CH₃ | —H | —CH₃ | —CH₃ |
| 271 | —OCH₃ | —CH₃ | —OC(O)H | —H | —CH₃ | —CH₂CH₃ | —CH₃ | —CH₃ | —CH₃ | —CH₃ |
| 272 | —OCH₃ | —CH₃ | —OC(O)H | —H | —CH₃ | —CH₃ | —H | —H | —H | —CH₃ |
| 273 | —OCH₃ | —CH₃ | —OC(O)H | —H | —CH₃ | —CH₂CH₃ | —H | —H | —H | —CH₃ |
| 274 | —OCH₃ | —CH₃ | —OC(O)H | —H | —CH₃ | —CH₃ | —H | —CH₃ | —H | —CH₃ |
| 275 | —OCH₃ | —CH₃ | —OC(O)H | —H | —CH₃ | —CH₂CH₃ | —H | —CH₃ | —H | —CH₃ |
| 276 | —OCH₃ | —CH₃ | —OC(O)H | —H | —CH₃ | —CH₃ | —H | —CH₂CH₃ | —H | —CH₃ |
| 277 | —OCH₃ | —CH₃ | —OC(O)H | —H | —CH₃ | —CH₃ | —CH₃ | —H | —H | —CH₃ |
| 278 | —OCH₃ | —CH₃ | —OC(O)H | —H | —CH₃ | —CH₂CH₃ | —CH₃ | —H | —H | —CH₃ |
| 279 | —OCH₃ | —CH₃ | —OC(O)H | —H | —CH₃ | —CH₃ | —CH₃ | —CH₃ | —H | —CH₃ |
| 280 | —OCH₃ | —CH₃ | —OC(O)H | —H | —CH₃ | —CH₂CH₃ | —CH₃ | —CH₃ | —H | —CH₃ |
| 281 | —OCH₃ | —CH₃ | —OC(O)H | —H | —CH₃ | —CH₃ | —CH₃ | —CH₂CH₃ | —H | —CH₃ |
| 282 | —OCH₃ | —CH₃ | —OC(O)H | —H | —CH₃ | —CH₃ | —CH₂CH₃ | —H | —H | —CH₃ |
| 283 | —OCH₃ | —CH₃ | —OC(O)H | —H | —CH₃ | —CH₃ | —CH₂CH₃ | —CH₃ | —H | —CH₃ |
| 284 | —OCH₃ | —CH₂CH₃ | —OC(O)H | —H | —H | —CH₃ | —H | —H | —CH₃ | —CH₃ |
| 285 | —OCH₃ | —CH₂CH₃ | —OC(O)H | —H | —H | —CH₃ | —H | —H | —CH₂CH₃ | —CH₃ |
| 286 | —OCH₃ | —CH₂CH₃ | —OC(O)H | —H | —H | —CH₃ | —H | —CH₃ | —CH₃ | —CH₃ |
| 287 | —OCH₃ | —CH₂CH₃ | —OC(O)H | —H | —H | —CH₃ | —H | —CH₃ | —CH₂CH₃ | —CH₃ |
| 288 | —OCH₃ | —CH₂CH₃ | —OC(O)H | —H | —H | —CH₃ | —H | —CH₂CH₃ | —CH₃ | —CH₃ |
| 289 | —OCH₃ | —CH₂CH₃ | —OC(O)H | —H | —H | —CH₃ | —CH₃ | —H | —CH₃ | —CH₃ |
| 290 | —OCH₃ | —CH₂CH₃ | —OC(O)H | —H | —H | —CH₃ | —CH₃ | —H | —CH₂CH₃ | —CH₃ |
| 291 | —OCH₃ | —CH₂CH₃ | —OC(O)H | —H | —H | —CH₃ | —CH₃ | —CH₃ | —CH₃ | —CH₃ |
| 292 | —OCH₃ | —CH₂CH₃ | —OC(O)H | —H | —H | —CH₃ | —CH₃ | —CH₃ | —CH₂CH₃ | —CH₃ |
| 293 | —OCH₃ | —CH₂CH₃ | —OC(O)H | —H | —H | —CH₃ | —CH₃ | —CH₂CH₃ | —CH₃ | —CH₃ |
| 294 | —OCH₃ | —CH₂CH₃ | —OC(O)H | —H | —H | —CH₃ | —CH₂CH₃ | —H | —CH₃ | —CH₃ |
| 295 | —OCH₃ | —CH₂CH₃ | —OC(O)H | —H | —H | —CH₃ | —CH₂CH₃ | —CH₃ | —CH₃ | —CH₃ |
| 296 | —OCH₃ | —CH₂CH₃ | —OC(O)H | —H | —H | —CH₂CH₃ | —H | —H | —CH₃ | —CH₃ |
| 297 | —OCH₃ | —CH₂CH₃ | —OC(O)H | —H | —H | —CH₂CH₃ | —H | —CH₃ | —CH₃ | —CH₃ |
| 298 | —OCH₃ | —CH₂CH₃ | —OC(O)H | —H | —H | —CH₂CH₃ | —CH₃ | —H | —CH₃ | —CH₃ |
| 299 | —OCH₃ | —CH₂CH₃ | —OC(O)H | —H | —H | —CH₂CH₃ | —CH₃ | —CH₃ | —CH₃ | —CH₃ |
| 300 | —OCH₃ | —CH₂CH₃ | —OC(O)H | —H | —CH₃ | —CH₃ | —H | —H | —CH₃ | —CH₃ |
| 301 | —OCH₃ | —CH₂CH₃ | —OC(O)H | —H | —CH₃ | —CH₃ | —H | —H | —CH₂CH₃ | —CH₃ |
| 302 | —OCH₃ | —CH₂CH₃ | —OC(O)H | —H | —CH₃ | —CH₃ | —H | —CH₃ | —CH₃ | —CH₃ |
| 303 | —OCH₃ | —CH₂CH₃ | —OC(O)H | —H | —CH₃ | —CH₃ | —H | —CH₃ | —CH₂CH₃ | —CH₃ |

5,292,719

TABLE I-continued

| | | | | | | | | | | |
|---|---|---|---|---|---|---|---|---|---|---|
| 304 | —OCH₃ | —CH₂CH₃ | —OC(O)H | —H | —CH₃ | —CH₃ | —H | —CH₂CH₃ | —CH₃ | —CH₃ |
| 305 | —OCH₃ | —CH₂CH₃ | —OC(O)H | —H | —CH₃ | —CH₃ | —CH₃ | —H | —CH₃ | —CH₃ |
| 306 | —OCH₃ | —CH₂CH₃ | —OC(O)H | —H | —CH₃ | —CH₃ | —CH₃ | —H | —CH₂CH₃ | —CH₃ |
| 307 | —OCH₃ | —CH₂CH₃ | —OC(O)H | —H | —CH₃ | —CH₃ | —CH₃ | —CH₃ | —CH₃ | —CH₃ |
| 308 | —OCH₃ | —CH₂CH₃ | —OC(O)H | —H | —CH₃ | —CH₃ | —CH₃ | —CH₃ | —CH₂CH₃ | —CH₃ |
| 309 | —OCH₃ | —CH₂CH₃ | —OC(O)H | —H | —CH₃ | —CH₃ | —CH₃ | —CH₂CH₃ | —CH₃ | —CH₃ |
| 310 | —OCH₃ | —CH₂CH₃ | —OC(O)H | —H | —CH₃ | —CH₃ | —CH₂CH₃ | —H | —CH₃ | —CH₃ |
| 311 | —OCH₃ | —CH₂CH₃ | —OC(O)H | —H | —CH₃ | —CH₃ | —CH₂CH₃ | —CH₃ | —CH₃ | —CH₃ |
| 312 | —OCH₃ | —CH₂CH₃ | —OC(O)H | —H | —CH₃ | —CH₂CH₃ | —H | —H | —CH₃ | —CH₃ |
| 313 | —OCH₃ | —CH₂CH₃ | —OC(O)H | —H | —CH₃ | —CH₂CH₃ | —H | —CH₃ | —CH₃ | —CH₃ |
| 314 | —OCH₃ | —CH₂CH₃ | —OC(O)H | —H | —CH₃ | —CH₂CH₃ | —CH₃ | —H | —CH₃ | —CH₃ |
| 315 | —OCH₃ | —CH₂CH₃ | —OC(O)H | —H | —CH₃ | —CH₂CH₃ | —CH₃ | —CH₃ | —CH₃ | —CH₃ |
| 316 | —OCH₃ | —CH₂CH₃ | —OC(O)H | —H | —CH₃ | —CH₂CH₃ | —H | —H | —CH₃ | —CH₃ |
| 317 | —OCH₃ | —CH₂CH₃ | —OC(O)H | —H | —CH₃ | —CH₂CH₃ | —H | —CH₃ | —CH₃ | —CH₃ |
| 318 | —OCH₃ | —CH₂CH₃ | —OC(O)H | —H | —CH₃ | —CH₂CH₃ | —CH₃ | —H | —CH₃ | —CH₃ |
| 319 | —OCH₃ | —CH₂CH₃ | —OC(O)H | —H | —CH₃ | —CH₂CH₃ | —CH₃ | —CH₃ | —CH₃ | —CH₃ |
| 320 | —OCH₃ | —CH₂CH₃ | —OC(O)H | —H | —CH₃ | —CH₃ | —H | —H | —H | —CH₃ |
| 321 | —OCH₃ | —CH₂CH₃ | —OC(O)H | —H | —CH₃ | —CH₂CH₃ | —H | —H | —H | —CH₃ |
| 322 | —OCH₃ | —CH₂CH₃ | —OC(O)H | —H | —CH₃ | —CH₃ | —H | —CH₃ | —H | —CH₃ |
| 323 | —OCH₃ | —CH₂CH₃ | —OC(O)H | —H | —CH₃ | —CH₂CH₃ | —H | —CH₃ | —H | —CH₃ |
| 324 | —OCH₃ | —CH₂CH₃ | —OC(O)H | —H | —CH₃ | —CH₃ | —H | —CH₂CH₃ | —H | —CH₃ |
| 325 | —OCH₃ | —CH₂CH₃ | —OC(O)H | —H | —CH₃ | —CH₃ | —CH₃ | —H | —H | —CH₃ |
| 326 | —OCH₃ | —CH₂CH₃ | —OC(O)H | —H | —CH₃ | —CH₂CH₃ | —CH₃ | —H | —H | —CH₃ |
| 327 | —OCH₃ | —CH₂CH₃ | —OC(O)H | —H | —CH₃ | —CH₃ | —CH₃ | —CH₃ | —H | —CH₃ |
| 328 | —OCH₃ | —CH₂CH₃ | —OC(O)H | —H | —CH₃ | —CH₂CH₃ | —CH₃ | —CH₃ | —H | —CH₃ |
| 329 | —OCH₃ | —CH₂CH₃ | —OC(O)H | —H | —CH₃ | —CH₃ | —CH₃ | —CH₂CH₃ | —H | —CH₃ |
| 330 | —OCH₃ | —CH₂CH₃ | —OC(O)H | —H | —CH₃ | —CH₃ | —CH₂CH₃ | —H | —H | —CH₃ |
| 331 | —OCH₃ | —CH₂CH₃ | —OC(O)H | —H | —CH₃ | —CH₃ | —CH₂CH₃ | —CH₃ | —H | —CH₃ |
| 332 | —OCH₃ | —OCH₃ | —OC(O)H | —H | —H | —CH₃ | —H | —H | —CH₃ | —CH₃ |
| 333 | —OCH₃ | —OCH₃ | —OC(O)H | —H | —H | —CH₃ | —H | —H | —CH₂CH₃ | —CH₃ |
| 334 | —OCH₃ | —OCH₃ | —OC(O)H | —H | —H | —CH₃ | —H | —CH₃ | —CH₃ | —CH₃ |
| 335 | —OCH₃ | —OCH₃ | —OC(O)H | —H | —H | —CH₃ | —H | —CH₃ | —CH₂CH₃ | —CH₃ |
| 336 | —OCH₃ | —OCH₃ | —OC(O)H | —H | —H | —CH₃ | —H | —CH₂CH₃ | —CH₃ | —CH₃ |
| 337 | —OCH₃ | —OCH₃ | —OC(O)H | —H | —H | —CH₃ | —CH₃ | —H | —CH₃ | —CH₃ |
| 338 | —OCH₃ | —OCH₃ | —OC(O)H | —H | —H | —CH₃ | —CH₃ | —H | —CH₂CH₃ | —CH₃ |
| 339 | —OCH₃ | —OCH₃ | —OC(O)H | —H | —H | —CH₃ | —CH₃ | —CH₃ | —CH₃ | —CH₃ |
| 340 | —OCH₃ | —OCH₃ | —OC(O)H | —H | —H | —CH₃ | —CH₃ | —CH₃ | —CH₂CH₃ | —CH₃ |
| 341 | —OCH₃ | —OCH₃ | —OC(O)H | —H | —H | —CH₃ | —CH₂CH₃ | —CH₃ | —CH₃ | —CH₃ |
| 342 | —OCH₃ | —OCH₃ | —OC(O)H | —H | —H | —CH₃ | —CH₂CH₃ | —H | —CH₃ | —CH₃ |
| 343 | —OCH₃ | —OCH₃ | —OC(O)H | —H | —H | —CH₃ | —CH₂CH₃ | —CH₃ | —CH₃ | —CH₃ |
| 344 | —OCH₃ | —OCH₃ | —OC(O)H | —H | —H | —CH₂CH₃ | —H | —H | —CH₃ | —CH₃ |
| 345 | —OCH₃ | —OCH₃ | —OC(O)H | —H | —H | —CH₂CH₃ | —H | —CH₃ | —CH₃ | —CH₃ |
| 346 | —OCH₃ | —OCH₃ | —OC(O)H | —H | —H | —CH₂CH₃ | —CH₃ | —H | —CH₃ | —CH₃ |
| 347 | —OCH₃ | —OCH₃ | —OC(O)H | —H | —H | —CH₂CH₃ | —CH₃ | —CH₃ | —CH₃ | —CH₃ |
| 348 | —OCH₃ | —OCH₃ | —OC(O)H | —H | —CH₃ | —CH₃ | —H | —H | —CH₃ | —CH₃ |
| 349 | —OCH₃ | —OCH₃ | —OC(O)H | —H | —CH₃ | —CH₃ | —H | —H | —CH₂CH₃ | —CH₃ |
| 350 | —OCH₃ | —OCH₃ | —OC(O)H | —H | —CH₃ | —CH₃ | —H | —CH₃ | —CH₃ | —CH₃ |
| 351 | —OCH₃ | —OCH₃ | —OC(O)H | —H | —CH₃ | —CH₃ | —H | —CH₃ | —CH₂CH₃ | —CH₃ |
| 352 | —OCH₃ | —OCH₃ | —OC(O)H | —H | —CH₃ | —CH₃ | —H | —CH₂CH₃ | —CH₃ | —CH₃ |
| 353 | —OCH₃ | —OCH₃ | —OC(O)H | —H | —CH₃ | —CH₃ | —CH₃ | —H | —CH₃ | —CH₃ |
| 354 | —OCH₃ | —OCH₃ | —OC(O)H | —H | —CH₃ | —CH₃ | —CH₃ | —H | —CH₂CH₃ | —CH₃ |
| 355 | —OCH₃ | —OCH₃ | —OC(O)H | —H | —CH₃ | —CH₃ | —CH₃ | —CH₃ | —CH₃ | —CH₃ |
| 356 | —OCH₃ | —OCH₃ | —OC(O)H | —H | —CH₃ | —CH₃ | —CH₃ | —CH₃ | —CH₂CH₃ | —CH₃ |
| 357 | —OCH₃ | —OCH₃ | —OC(O)H | —H | —CH₃ | —CH₃ | —CH₃ | —CH₂CH₃ | —CH₃ | —CH₃ |
| 358 | —OCH₃ | —OCH₃ | —OC(O)H | —H | —CH₃ | —CH₃ | —CH₂CH₃ | —H | —CH₃ | —CH₃ |
| 359 | —OCH₃ | —OCH₃ | —OC(O)H | —H | —CH₃ | —CH₃ | —CH₂CH₃ | —CH₃ | —CH₃ | —CH₃ |
| 360 | —OCH₃ | —OCH₃ | —OC(O)H | —H | —CH₃ | —CH₂CH₃ | —H | —H | —CH₃ | —CH₃ |
| 361 | —OCH₃ | —OCH₃ | —OC(O)H | —H | —CH₃ | —CH₂CH₃ | —H | —CH₃ | —CH₃ | —CH₃ |
| 362 | —OCH₃ | —OCH₃ | —OC(O)H | —H | —CH₃ | —CH₂CH₃ | —CH₃ | —H | —CH₃ | —CH₃ |
| 363 | —OCH₃ | —OCH₃ | —OC(O)H | —H | —CH₃ | —CH₂CH₃ | —CH₃ | —CH₃ | —CH₃ | —CH₃ |
| 364 | —OCH₃ | —OCH₃ | —OC(O)H | —H | —CH₃ | —CH₂CH₃ | —H | —H | —CH₃ | —CH₃ |
| 365 | —OCH₃ | —OCH₃ | —OC(O)H | —H | —CH₃ | —CH₂CH₃ | —H | —CH₃ | —CH₃ | —CH₃ |
| 366 | —OCH₃ | —OCH₃ | —OC(O)H | —H | —CH₃ | —CH₂CH₃ | —CH₃ | —H | —CH₃ | —CH₃ |
| 367 | —OCH₃ | —OCH₃ | —OC(O)H | —H | —CH₃ | —CH₂CH₃ | —CH₃ | —CH₃ | —CH₃ | —CH₃ |
| 368 | —OCH₃ | —OCH₃ | —OC(O)H | —H | —CH₃ | —CH₃ | —H | —H | —H | —CH₃ |
| 369 | —OCH₃ | —OCH₃ | —OC(O)H | —H | —CH₃ | —CH₂CH₃ | —H | —H | —H | —CH₃ |
| 370 | —OCH₃ | —OCH₃ | —OC(O)H | —H | —CH₃ | —CH₃ | —H | —CH₃ | —H | —CH₃ |
| 371 | —OCH₃ | —OCH₃ | —OC(O)H | —H | —CH₃ | —CH₂CH₃ | —H | —CH₃ | —H | —CH₃ |
| 372 | —OCH₃ | —OCH₃ | —OC(O)H | —H | —CH₃ | —CH₃ | —H | —CH₂CH₃ | —H | —CH₃ |
| 373 | —OCH₃ | —OCH₃ | —OC(O)H | —H | —CH₃ | —CH₃ | —CH₃ | —H | —H | —CH₃ |
| 374 | —OCH₃ | —OCH₃ | —OC(O)H | —H | —CH₃ | —CH₂CH₃ | —CH₃ | —H | —H | —CH₃ |
| 375 | —OCH₃ | —OCH₃ | —OC(O)H | —H | —CH₃ | —CH₃ | —CH₃ | —CH₃ | —H | —CH₃ |
| 376 | —OCH₃ | —OCH₃ | —OC(O)H | —H | —CH₃ | —CH₂CH₃ | —CH₃ | —CH₃ | —H | —CH₃ |
| 377 | —OCH₃ | —OCH₃ | —OC(O)H | —H | —CH₃ | —CH₃ | —CH₃ | —CH₂CH₃ | —H | —CH₃ |
| 378 | —OCH₃ | —OCH₃ | —OC(O)H | —H | —CH₃ | —CH₃ | —CH₂CH₃ | —H | —H | —CH₃ |
| 379 | —OCH₃ | —OCH₃ | —OC(O)H | —H | —CH₃ | —CH₃ | —CH₂CH₃ | —CH₃ | —H | —CH₃ |
| 380 | —OH | —OH | —CH₃ | —OC(O)H | —H | —CH₃ | —H | —H | —CH₃ | —CH₃ |
| 381 | —OH | —CH₃ | —OC(O)H | —H | —H | —CH₃ | —H | —H | —CH₂CH₃ | —CH₃ |
| 382 | —OH | —CH₃ | —OC(O)H | —H | —H | —CH₃ | —H | —CH₃ | —CH₃ | —CH₃ |

-continued

| | | | | | | | | | |
|---|---|---|---|---|---|---|---|---|---|
| 383 | —OH | —CH₃ | —OC(O)H | —H | —H | —CH₃ | —H | —CH₃ | —CH₂CH₃ | —CH₃ |
| 384 | —OH | —CH₃ | —OC(O)H | —H | —H | —CH₃ | —H | —CH₂CH₃ | —CH₃ | —CH₃ |
| 385 | —OH | —CH₃ | —OC(O)H | —H | —H | —CH₃ | —CH₃ | —H | —CH₃ | —CH₃ |
| 386 | —OH | —CH₃ | —OC(O)H | —H | —H | —CH₃ | —CH₃ | —H | —CH₂CH₃ | —CH₃ |
| 387 | —OH | —CH₃ | —OC(O)H | —H | —H | —CH₃ | —CH₃ | —CH₃ | —CH₃ | —CH₃ |
| 388 | —OH | —CH₃ | —OC(O)H | —H | —H | —CH₃ | —CH₃ | —CH₃ | —CH₂CH₃ | —CH₃ |
| 389 | —OH | —CH₃ | —OC(O)H | —H | —H | —CH₃ | —CH₃ | —CH₂CH₃ | —CH₃ | —CH₃ |
| 390 | —OH | —CH₃ | —OC(O)H | —H | —H | —CH₃ | —CH₂CH₃ | —H | —CH₃ | —CH₃ |
| 391 | —OH | —CH₃ | —OC(O)H | —H | —H | —CH₃ | —CH₂CH₃ | —CH₃ | —CH₃ | —CH₃ |
| 392 | —OH | —CH₃ | —OC(O)H | —H | —H | —CH₂CH₃ | —H | —H | —CH₃ | —CH₃ |
| 393 | —OH | —CH₃ | —OC(O)H | —H | —H | —CH₂CH₃ | —H | —CH₃ | —CH₃ | —CH₃ |
| 394 | —OH | —CH₃ | —OC(O)H | —H | —H | —CH₂CH₃ | —CH₃ | —H | —CH₃ | —CH₃ |
| 395 | —OH | —CH₃ | —OC(O)H | —H | —H | —CH₂CH₃ | —CH₃ | —CH₃ | —CH₃ | —CH₃ |
| 396 | —OH | —CH₃ | —OC(O)H | —H | —CH₃ | —CH₃ | —H | —H | —CH₃ | —CH₃ |
| 397 | —OH | —CH₃ | —OC(O)H | —H | —CH₃ | —CH₃ | —H | —H | —CH₂CH₃ | —CH₃ |
| 398 | —OH | —CH₃ | —OC(O)H | —H | —CH₃ | —CH₃ | —H | —CH₃ | —CH₃ | —CH₃ |
| 399 | —OH | —CH₃ | —OC(O)H | —H | —CH₃ | —CH₃ | —H | —CH₃ | —CH₂CH₃ | —CH₃ |
| 400 | —OH | —CH₃ | —OC(O)H | —H | —CH₃ | —CH₃ | —H | —CH₂CH₃ | —CH₃ | —CH₃ |
| 401 | —OH | —CH₃ | —OC(O)H | —H | —CH₃ | —CH₃ | —CH₃ | —H | —CH₃ | —CH₃ |
| 402 | —OH | —CH₃ | —OC(O)H | —H | —CH₃ | —CH₃ | —CH₃ | —H | —CH₂CH₃ | —CH₃ |
| 403 | —OH | —CH₃ | —OC(O)H | —H | —CH₃ | —CH₃ | —CH₃ | —CH₃ | —CH₃ | —CH₃ |
| 404 | —OH | —CH₃ | —OC(O)H | —H | —CH₃ | —CH₃ | —CH₃ | —CH₃ | —CH₂CH₃ | —CH₃ |
| 405 | —OH | —CH₃ | —OC(O)H | —H | —CH₃ | —CH₃ | —CH₃ | —CH₂CH₃ | —CH₃ | —CH₃ |
| 406 | —OH | —CH₃ | —OC(O)H | —H | —CH₃ | —CH₃ | —CH₂CH₃ | —H | —CH₃ | —CH₃ |
| 407 | —OH | —CH₃ | —OC(O)H | —H | —CH₃ | —CH₃ | —CH₂CH₃ | —CH₃ | —CH₃ | —CH₃ |
| 408 | —OH | —CH₃ | —OC(O)H | —H | —CH₃ | —CH₂CH₃ | —H | —H | —CH₃ | —CH₃ |
| 409 | —OH | —CH₃ | —OC(O)H | —H | —CH₃ | —CH₂CH₃ | —H | —CH₃ | —CH₃ | —CH₃ |
| 410 | —OH | —CH₃ | —OC(O)H | —H | —CH₃ | —CH₂CH₃ | —CH₃ | —H | —CH₃ | —CH₃ |
| 411 | —OH | —CH₃ | —OC(O)H | —H | —CH₃ | —CH₂CH₃ | —CH₃ | —CH₃ | —CH₃ | —CH₃ |
| 412 | —OH | —CH₃ | —OC(O)H | —H | —CH₃ | —CH₂CH₃ | —H | —H | —CH₃ | —CH₃ |
| 413 | —OH | —CH₃ | —OC(O)H | —H | —CH₃ | —CH₂CH₃ | —H | —CH₃ | —CH₃ | —CH₃ |
| 414 | —OH | —CH₃ | —OC(O)H | —H | —CH₃ | —CH₂CH₃ | —CH₃ | —H | —CH₃ | —CH₃ |
| 415 | —OH | —CH₃ | —OC(O)H | —H | —CH₃ | —CH₂CH₃ | —CH₃ | —CH₃ | —CH₃ | —CH₃ |
| 416 | —OH | —CH₃ | —OC(O)H | —H | —CH₃ | —CH₃ | —H | —H | —H | —CH₃ |
| 417 | —OH | —CH₃ | —OC(O)H | —H | —CH₃ | —CH₂CH₃ | —H | —H | —H | —CH₃ |
| 418 | —OH | —CH₃ | —OC(O)H | —H | —CH₃ | —CH₃ | —H | —CH₃ | —H | —CH₃ |
| 419 | —OH | —CH₃ | —OC(O)H | —H | —CH₃ | —CH₂CH₃ | —H | —CH₃ | —H | —CH₃ |
| 420 | —OH | —CH₃ | —OC(O)H | —H | —CH₃ | —CH₃ | —H | —CH₂CH₃ | —H | —CH₃ |
| 421 | —OH | —CH₃ | —OC(O)H | —H | —CH₃ | —CH₃ | —CH₃ | —H | —H | —CH₃ |
| 422 | —OH | —CH₃ | —OC(O)H | —H | —CH₃ | —CH₂CH₃ | —CH₃ | —H | —H | —CH₃ |
| 423 | —OH | —CH₃ | —OC(O)H | —H | —CH₃ | —CH₃ | —CH₃ | —CH₃ | —H | —CH₃ |
| 424 | —OH | —CH₃ | —OC(O)H | —H | —CH₃ | —CH₂CH₃ | —CH₃ | —CH₃ | —H | —CH₃ |
| 425 | —OH | —CH₃ | —OC(O)H | —H | —CH₃ | —CH₃ | —CH₃ | —CH₂CH₃ | —H | —CH₃ |
| 426 | —OH | —CH₃ | —OC(O)H | —H | —CH₃ | —CH₃ | —CH₂CH₃ | —H | —H | —CH₃ |
| 427 | —OH | —CH₃ | —OC(O)H | —H | —CH₃ | —CH₃ | —CH₂CH₃ | —CH₃ | —H | —CH₃ |
| 428 | —OH | —CH₂CH₃ | —OC(O)H | —H | —H | —CH₃ | —H | —H | —CH₃ | —CH₃ |
| 429 | —OH | —CH₂CH₃ | —OC(O)H | —H | —H | —CH₃ | —H | —H | —CH₂CH₃ | —CH₃ |
| 430 | —OH | —CH₂CH₃ | —OC(O)H | —H | —H | —CH₃ | —H | —CH₃ | —CH₃ | —CH₃ |
| 431 | —OH | —CH₂CH₃ | —OC(O)H | —H | —H | —CH₃ | —H | —CH₃ | —CH₂CH₃ | —CH₃ |
| 432 | —OH | —CH₂CH₃ | —OC(O)H | —H | —H | —CH₃ | —H | —CH₂CH₃ | —CH₃ | —CH₃ |
| 433 | —OH | —CH₂CH₃ | —OC(O)H | —H | —H | —CH₃ | —CH₃ | —H | —CH₃ | —CH₃ |
| 434 | —OH | —CH₂CH₃ | —OC(O)H | —H | —H | —CH₃ | —CH₃ | —H | —CH₂CH₃ | —CH₃ |
| 435 | —OH | —CH₂CH₃ | —OC(O)H | —H | —H | —CH₃ | —CH₃ | —CH₃ | —CH₃ | —CH₃ |
| 436 | —OH | —CH₂CH₃ | —OC(O)H | —H | —H | —CH₃ | —CH₃ | —CH₃ | —CH₂CH₃ | —CH₃ |
| 437 | —OH | —CH₂CH₃ | —OC(O)H | —H | —H | —CH₃ | —CH₃ | —CH₂CH₃ | —CH₃ | —CH₃ |
| 438 | —OH | —CH₂CH₃ | —OC(O)H | —H | —H | —CH₃ | —CH₂CH₃ | —H | —CH₃ | —CH₃ |
| 439 | —OH | —CH₂CH₃ | —OC(O)H | —H | —H | —CH₃ | —CH₂CH₃ | —CH₃ | —CH₃ | —CH₃ |
| 440 | —OH | —CH₂CH₃ | —OC(O)H | —H | —H | —CH₂CH₃ | —H | —H | —CH₃ | —CH₃ |
| 441 | —OH | —CH₂CH₃ | —OC(O)H | —H | —H | —CH₂CH₃ | —H | —CH₃ | —CH₃ | —CH₃ |
| 442 | —OH | —CH₂CH₃ | —OC(O)H | —H | —H | —CH₂CH₃ | —CH₃ | —H | —CH₃ | —CH₃ |
| 443 | —OH | —CH₂CH₃ | —OC(O)H | —H | —H | —CH₂CH₃ | —CH₃ | —CH₃ | —CH₃ | —CH₃ |
| 444 | —OH | —CH₂CH₃ | —OC(O)H | —H | —CH₃ | —CH₃ | —H | —H | —CH₃ | —CH₃ |
| 445 | —OH | —CH₂CH₃ | —OC(O)H | —H | —CH₃ | —CH₃ | —H | —H | —CH₂CH₃ | —CH₃ |
| 446 | —OH | —CH₂CH₃ | —OC(O)H | —H | —CH₃ | —CH₃ | —H | —CH₃ | —CH₃ | —CH₃ |
| 447 | —OH | —CH₂CH₃ | —OC(O)H | —H | —CH₃ | —CH₃ | —H | —CH₃ | —CH₂CH₃ | —CH₃ |
| 448 | —OH | —CH₂CH₃ | —OC(O)H | —H | —CH₃ | —CH₃ | —H | —CH₂CH₃ | —CH₃ | —CH₃ |
| 449 | —OH | —CH₂CH₃ | —OC(O)H | —H | —CH₃ | —CH₃ | —CH₃ | —H | —CH₃ | —CH₃ |
| 450 | —OH | —CH₂CH₃ | —OC(O)H | —H | —CH₃ | —CH₃ | —CH₃ | —H | —CH₂CH₃ | —CH₃ |
| 451 | —OH | —CH₂CH₃ | —OC(O)H | —H | —CH₃ | —CH₃ | —CH₃ | —CH₃ | —CH₃ | —CH₃ |
| 452 | —OH | —CH₂CH₃ | —OC(O)H | —H | —CH₃ | —CH₃ | —CH₃ | —CH₃ | —CH₂CH₃ | —CH₃ |
| 453 | —OH | —CH₂CH₃ | —OC(O)H | —H | —CH₃ | —CH₃ | —CH₃ | —CH₂CH₃ | —CH₃ | —CH₃ |
| 454 | —OH | —CH₂CH₃ | —OC(O)H | —H | —CH₃ | —CH₃ | —CH₂CH₃ | —H | —CH₃ | —CH₃ |
| 455 | —OH | —CH₂CH₃ | —OC(O)H | —H | —CH₃ | —CH₃ | —CH₂CH₃ | —CH₃ | —CH₃ | —CH₃ |
| 456 | —OH | —CH₂CH₃ | —OC(O)H | —H | —CH₃ | —CH₂CH₃ | —H | —H | —CH₃ | —CH₃ |
| 457 | —OH | —CH₂CH₃ | —OC(O)H | —H | —CH₃ | —CH₂CH₃ | —H | —CH₃ | —CH₃ | —CH₃ |
| 458 | —OH | —CH₂CH₃ | —OC(O)H | —H | —CH₃ | —CH₂CH₃ | —CH₃ | —H | —CH₃ | —CH₃ |
| 459 | —OH | —CH₂CH₃ | —OC(O)H | —H | —CH₃ | —CH₂CH₃ | —CH₃ | —CH₃ | —CH₃ | —CH₃ |
| 460 | —OH | —CH₂CH₃ | —OC(O)H | —H | —CH₃ | —CH₂CH₃ | —H | —H | —CH₃ | —CH₃ |
| 461 | —OH | —CH₂CH₃ | —OC(O)H | —H | —CH₃ | —CH₂CH₃ | —H | —CH₃ | —CH₃ | —CH₃ |
| 462 | —OH | —CH₂CH₃ | —OC(O)H | —H | —CH₃ | —CH₂CH₃ | —CH₃ | —H | —CH₃ | —CH₃ |
| 463 | —OH | —CH₂CH₃ | —OC(O)H | —H | —CH₃ | —CH₂CH₃ | —CH₃ | —CH₃ | —CH₃ | —CH₃ |
| 464 | —OH | —CH₂CH₃ | —OC(O)H | —H | —CH₃ | —CH₃ | —H | —H | —H | —CH₃ |
| 465 | —OH | —CH₂CH₃ | —OC(O)H | —H | —CH₃ | —CH₂CH₃ | —H | —H | —H | —CH₃ |

-continued

| | | | | | | | | | |
|---|---|---|---|---|---|---|---|---|---|
| 466 | —OH | —CH₂CH₃ | —OC(O)H | —H | —CH₃ | —CH₃ | —H | —CH₃ | —H | —CH₃ |
| 467 | —OH | —CH₂CH₃ | —OC(O)H | —H | —CH₃ | —CH₂CH₃ | —H | —CH₃ | —H | —CH₃ |
| 468 | —OH | —CH₂CH₃ | —OC(O)H | —H | —CH₃ | —CH₃ | —H | —CH₂CH₃ | —H | —CH₃ |
| 469 | —OH | —CH₂CH₃ | —OC(O)H | —H | —CH₃ | —CH₃ | —CH₃ | —H | —H | —CH₃ |
| 470 | —OH | —CH₂CH₃ | —OC(O)H | —H | —CH₃ | —CH₂CH₃ | —CH₃ | —H | —H | —CH₃ |
| 471 | —OH | —CH₂CH₃ | —OC(O)H | —H | —CH₃ | —CH₃ | —CH₃ | —CH₃ | —H | —CH₃ |
| 472 | —OH | —CH₂CH₃ | —OC(O)H | —H | —CH₃ | —CH₂CH₃ | —CH₃ | —CH₃ | —H | —CH₃ |
| 473 | —OH | —CH₂CH₃ | —OC(O)H | —H | —CH₃ | —CH₃ | —CH₃ | —CH₂CH₃ | —H | —CH₃ |
| 474 | —OH | —CH₂CH₃ | —OC(O)H | —H | —CH₃ | —CH₃ | —CH₂CH₃ | —H | —H | —CH₃ |
| 475 | —OH | —CH₂CH₃ | —OC(O)H | —H | —CH₃ | —CH₃ | —CH₂CH₃ | —CH₃ | —H | —CH₃ |
| 476 | —CH₃ | —OC(O)H | —H | —H | —H | —CH₃ | —H | —H | —CH₃ | —CH₃ |
| 477 | —CH₃ | —OC(O)H | —H | —H | —H | —CH₃ | —H | —H | —CH₂CH₃ | —CH₃ |
| 478 | —CH₃ | —OC(O)H | —H | —H | —H | —CH₂CH₃ | —H | —H | —CH₃ | —CH₃ |
| 479 | —CH₃ | —OC(O)H | —H | —H | —CH₃ | —CH₃ | —H | —H | —CH₃ | —CH₃ |
| 480 | —CH₃ | —OC(O)H | —H | —H | —CH₃ | —CH₃ | —H | —H | —CH₂CH₃ | —CH₃ |
| 481 | —CH₃ | —OC(O)H | —H | —H | —CH₃ | —CH₂CH₃ | —H | —H | —CH₃ | —CH₃ |
| 482 | —CH₃ | —OC(O)H | —H | —H | —CH₃ | —CH₂CH₃ | —H | —H | —CH₃ | —CH₃ |
| 483 | —CH₃ | —OC(O)H | —H | —H | —CH₃ | —CH₃ | —H | —H | —H | —CH₃ |
| 484 | —CH₃ | —OC(O)H | —H | —H | —CH₃ | —CH₂CH₃ | —H | —H | —H | —CH₃ |
| 485 | —CH₂CH₃ | —OC(O)H | —H | —H | —CH₃ | —CH₂CH₃ | —H | —H | —H | —CH₃ |
| 486 | —CH₂CH₃ | —OC(O)H | —H | —H | —H | —CH₃ | —H | —H | —CH₃ | —CH₃ |
| 487 | —CH₂CH₃ | —OC(O)H | —H | —H | —H | —CH₃ | —H | —H | —CH₂CH₃ | —CH₃ |
| 488 | —CH₂CH₃ | —OC(O)H | —H | —H | —H | —CH₂CH₃ | —H | —H | —CH₃ | —CH₃ |
| 489 | —CH₂CH₃ | —OC(O)H | —H | —H | —CH₃ | —CH₃ | —H | —H | —CH₃ | —CH₃ |
| 490 | —CH₂CH₃ | —OC(O)H | —H | —H | —CH₃ | —CH₃ | —H | —H | —CH₂CH₃ | —CH₃ |
| 491 | —CH₂CH₃ | —OC(O)H | —H | —H | —CH₃ | —CH₂CH₃ | —H | —H | —CH₃ | —CH₃ |
| 492 | —CH₂CH₃ | —OC(O)H | —H | —H | —CH₃ | —CH₂CH₃ | —H | —H | —CH₃ | —CH₃ |
| 493 | —CH₂CH₃ | —OC(O)H | —H | —H | —CH₃ | —CH₃ | —H | —H | —H | —CH₃ |
| 494 | —CH₃ | —OC(O)H | —CH₃ | —H | —H | —CH₃ | —H | —H | —CH₃ | —CH₃ |
| 495 | —CH₃ | —OC(O)H | —CH₃ | —H | —H | —CH₃ | —H | —H | —CH₂CH₃ | —CH₃ |
| 496 | —CH₃ | —OC(O)H | —CH₃ | —H | —H | —CH₂CH₃ | —H | —H | —CH₃ | —CH₃ |
| 497 | —CH₃ | —OC(O)H | —CH₃ | —H | —CH₃ | —CH₃ | —H | —H | —CH₃ | —CH₃ |
| 498 | —CH₃ | —OC(O)H | —CH₃ | —H | —CH₃ | —CH₃ | —H | —H | —CH₂CH₃ | —CH₃ |
| 499 | —CH₃ | —OC(O)H | —CH₃ | —H | —CH₃ | —CH₂CH₃ | —H | —H | —CH₃ | —CH₃ |
| 500 | —CH₃ | —OC(O)H | —CH₃ | —H | —CH₃ | —CH₂CH₃ | —H | —H | —CH₃ | —CH₃ |
| 501 | —CH₃ | —OC(O)H | —CH₃ | —H | —CH₃ | —CH₃ | —H | —H | —H | —CH₃ |
| 502 | —CH₃ | —OC(O)H | —CH₃ | —H | —CH₃ | —CH₂CH₃ | —H | —H | —H | —CH₃ |
| 503 | —CH₂CH₃ | —OC(O)H | —CH₃ | —H | —H | —CH₃ | —H | —H | —CH₃ | —CH₃ |
| 504 | —CH₂CH₃ | —OC(O)H | —CH₃ | —H | —H | —CH₃ | —H | —H | —CH₂CH₃ | —CH₃ |
| 505 | —CH₂CH₃ | —OC(O)H | —CH₃ | —H | —H | —CH₂CH₃ | —H | —H | —CH₃ | —CH₃ |
| 506 | —CH₂CH₃ | —OC(O)H | —CH₃ | —H | —CH₃ | —CH₃ | —H | —H | —CH₃ | —CH₃ |
| 507 | —CH₂CH₃ | —OC(O)H | —CH₃ | —H | —CH₃ | —CH₃ | —H | —H | —CH₂CH₃ | —CH₃ |
| 508 | —CH₂CH₃ | —OC(O)H | —CH₃ | —H | —CH₃ | —CH₂CH₃ | —H | —H | —CH₃ | —CH₃ |
| 509 | —CH₂CH₃ | —OC(O)H | —CH₃ | —H | —CH₃ | —CH₂CH₃ | —H | —H | —CH₃ | —CH₃ |
| 510 | —CH₂CH₃ | —OC(O)H | —CH₃ | —H | —CH₃ | —CH₃ | —H | —H | —H | —CH₃ |
| 511 | —CH₂CH₃ | —OC(O)H | —CH₃ | —H | —CH₃ | —CH₂CH₃ | —H | —H | —H | —CH₃ |
| 512 | —CH₃ | —OC(O)H | —CH₂CH₃ | —H | —H | —CH₃ | —H | —H | —CH₃ | —CH₃ |
| 513 | —CH₃ | —OC(O)H | —CH₂CH₃ | —H | —H | —CH₃ | —H | —H | —CH₂CH₃ | —CH₃ |
| 514 | —CH₃ | —OC(O)H | —CH₂CH₃ | —H | —H | —CH₂CH₃ | —H | —H | —CH₃ | —CH₃ |
| 515 | —CH₃ | —OC(O)H | —CH₂CH₃ | —H | —CH₃ | —CH₃ | —H | —H | —CH₃ | —CH₃ |
| 516 | —CH₃ | —OC(O)H | —CH₂CH₃ | —H | —CH₃ | —CH₃ | —H | —H | —CH₂CH₃ | —CH₃ |
| 517 | —CH₃ | —OC(O)H | —CH₂CH₃ | —H | —CH₃ | —CH₂CH₃ | —H | —H | —CH₃ | —CH₃ |
| 518 | —CH₃ | —OC(O)H | —CH₂CH₃ | —H | —CH₃ | —CH₂CH₃ | —H | —H | —CH₃ | —CH₃ |
| 519 | —CH₃ | —OC(O)H | —CH₂CH₃ | —H | —CH₃ | —CH₃ | —H | —H | —H | —CH₃ |
| 520 | —CH₃ | —OC(O)H | —CH₂CH₃ | —H | —CH₃ | —CH₂CH₃ | —H | —H | —H | —CH₃ |
| 521 | —CH₂CH₃ | —OC(O)H | —CH₂CH₃ | —H | —H | —CH₃ | —H | —H | —CH₃ | —CH₃ |
| 522 | —CH₂CH₃ | —OC(O)H | —CH₂CH₃ | —H | —H | —CH₃ | —H | —H | —CH₂CH₃ | —CH₃ |
| 523 | —CH₂CH₃ | —OC(O)H | —CH₂CH₃ | —H | —H | —CH₂CH₃ | —H | —H | —CH₃ | —CH₃ |
| 524 | —CH₂CH₃ | —OC(O)H | —CH₂CH₃ | —H | —CH₃ | —CH₃ | —H | —H | —CH₃ | —CH₃ |
| 525 | —CH₂CH₃ | —OC(O)H | —CH₂CH₃ | —H | —CH₃ | —CH₃ | —H | —H | —CH₂CH₃ | —CH₃ |
| 526 | —CH₂CH₃ | —OC(O)H | —CH₂CH₃ | —H | —CH₃ | —CH₂CH₃ | —H | —H | —CH₃ | —CH₃ |
| 527 | —CH₂CH₃ | —OC(O)H | —CH₂CH₃ | —H | —CH₃ | —CH₂CH₃ | —H | —H | —CH₃ | —CH₃ |
| 528 | —CH₂CH₃ | —OC(O)H | —CH₂CH₃ | —H | —CH₃ | —CH₃ | —H | —H | —H | —CH₃ |
| 529 | —CH₂CH₃ | —OC(O)H | —CH₂CH₃ | —H | —CH₃ | —CH₂CH₃ | —H | —H | —H | —CH₃ |
| 530 | —CH₃ | —OC(O)H | —OCH₃ | —H | —H | —CH₃ | —H | —H | —CH₃ | —CH₃ |
| 531 | —CH₃ | —OC(O)H | —OCH₃ | —H | —H | —CH₃ | —H | —H | —CH₂CH₃ | —CH₃ |
| 532 | —CH₃ | —OC(O)H | —OCH₃ | —H | —H | —CH₂CH₃ | —H | —H | —CH₃ | —CH₃ |
| 533 | —CH₃ | —OC(O)H | —OCH₃ | —H | —CH₃ | —CH₃ | —H | —H | —CH₃ | —CH₃ |
| 534 | —CH₃ | —OC(O)H | —OCH₃ | —H | —CH₃ | —CH₃ | —H | —H | —CH₂CH₃ | —CH₃ |
| 535 | —CH₃ | —OC(O)H | —OCH₃ | —H | —CH₃ | —CH₂CH₃ | —H | —H | —CH₃ | —CH₃ |
| 536 | —CH₃ | —OC(O)H | —OCH₃ | —H | —CH₃ | —CH₂CH₃ | —H | —H | —CH₃ | —CH₃ |
| 537 | —CH₃ | —OC(O)H | —OCH₃ | —H | —CH₃ | —CH₃ | —H | —H | —H | —CH₃ |
| 538 | —CH₃ | —OC(O)H | —OCH₃ | —H | —CH₃ | —CH₂CH₃ | —H | —H | —H | —CH₃ |
| 539 | —CH₂CH₃ | —OC(O)H | —OCH₃ | —H | —H | —CH₃ | —H | —H | —CH₃ | —CH₃ |
| 540 | —CH₂CH₃ | —OC(O)H | —OCH₃ | —H | —H | —CH₃ | —H | —H | —CH₂CH₃ | —CH₃ |
| 541 | —CH₂CH₃ | —OC(O)H | —OCH₃ | —H | —H | —CH₂CH₃ | —H | —H | —CH₃ | —CH₃ |
| 542 | —CH₂CH₃ | —OC(O)H | —OCH₃ | —H | —CH₃ | —CH₃ | —H | —H | —CH₃ | —CH₃ |
| 543 | —CH₂CH₃ | —OC(O)H | —OCH₃ | —H | —CH₃ | —CH₃ | —H | —H | —CH₂CH₃ | —CH₃ |
| 544 | —CH₂CH₃ | —OC(O)H | —OCH₃ | —H | —CH₃ | —CH₂CH₃ | —H | —H | —CH₃ | —CH₃ |
| 545 | —CH₂CH₃ | —OC(O)H | —OCH₃ | —H | —CH₃ | —CH₂CH₃ | —H | —H | —CH₃ | —CH₃ |
| 546 | —CH₂CH₃ | —OC(O)H | —OCH₃ | —H | —CH₃ | —CH₃ | —H | —H | —H | —CH₃ |
| 547 | —CH₂CH₃ | —OC(O)H | —OCH₃ | —H | —CH₃ | —CH₂CH₃ | —H | —H | —H | —CH₃ |
| 548 | —CH₃ | —OC(O)H | —OH | —H | —H | —CH₃ | —H | —H | —CH₃ | —CH₃ |

-continued

| # | 1 | 2 | 3 | 4 | 5 | 6 | 7 | 8 | 9 | 10 |
|---|---|---|---|---|---|---|---|---|---|---|
| 549 | —CH₃ | —OC(O)H | —OH | —H | —H | —CH₃ | —H | —H | —CH₂CH₃ | —CH₃ |
| 550 | —CH₃ | —OC(O)H | —OH | —H | —H | —CH₂CH₃ | —H | —H | —CH₃ | —CH₃ |
| 551 | —CH₃ | —OC(O)H | —OH | —H | —CH₃ | —CH₃ | —H | —H | —CH₃ | —CH₃ |
| 552 | —CH₃ | —OC(O)H | —OH | —H | —CH₃ | —CH₃ | —H | —H | —CH₂CH₃ | —CH₃ |
| 553 | —CH₃ | —OC(O)H | —OH | —H | —CH₃ | —CH₂CH₃ | —H | —H | —CH₃ | —CH₃ |
| 554 | —CH₃ | —OC(O)H | —OH | —H | —CH₃ | —CH₂CH₃ | —H | —H | —CH₃ | —CH₃ |
| 555 | —CH₃ | —OC(O)H | —OH | —H | —CH₃ | —CH₃ | —H | —H | —H | —CH₃ |
| 556 | —CH₃ | —OC(O)H | —OH | —H | —CH₃ | —CH₂CH₃ | —H | —H | —H | —CH₃ |
| 557 | —CH₂CH₃ | —OC(O)H | —OH | —H | —H | —CH₃ | —H | —H | —CH₃ | —CH₃ |
| 558 | —CH₂CH₃ | —OC(O)H | —OH | —H | —H | —CH₃ | —H | —H | —CH₂CH₃ | —CH₃ |
| 559 | —CH₂CH₃ | —OC(O)H | —OH | —H | —H | —CH₂CH₃ | —H | —H | —CH₃ | —CH₃ |
| 560 | —CH₂CH₃ | —OC(O)H | —OH | —H | —CH₃ | —CH₃ | —H | —H | —CH₃ | —CH₃ |
| 561 | —CH₂CH₃ | —OC(O)H | —OH | —H | —CH₃ | —CH₃ | —H | —H | —CH₂CH₃ | —CH₃ |
| 562 | —CH₂CH₃ | —OC(O)H | —OH | —H | —CH₃ | —CH₂CH₃ | —H | —H | —CH₃ | —CH₃ |
| 563 | —CH₂CH₃ | —OC(O)H | —OH | —H | —CH₃ | —CH₂CH₃ | —H | —H | —CH₃ | —CH₃ |
| 564 | —CH₂CH₃ | —OC(O)H | —OH | —H | —CH₃ | —CH₃ | —H | —H | —H | —CH₃ |
| 565 | —CH₂CH₃ | —OC(O)H | —OH | —H | —CH₃ | —CH₂CH₃ | —H | —H | —H | —CH₃ |
| 566 | —OCH₃ | —OC(O)H | —CH₃ | —H | —H | —CH₃ | —H | —H | —CH₃ | —CH₃ |
| 567 | —OCH₃ | —OC(O)H | —CH₃ | —H | —H | —CH₃ | —H | —H | —CH₂CH₃ | —CH₃ |
| 568 | —OCH₃ | —OC(O)H | —CH₃ | —H | —H | —CH₃ | —H | —CH₃ | —CH₃ | —CH₃ |
| 569 | —OCH₃ | —OC(O)H | —CH₃ | —H | —H | —CH₃ | —H | —CH₃ | —CH₂CH₃ | —CH₃ |
| 570 | —OCH₃ | —OC(O)H | —CH₃ | —H | —H | —CH₃ | —H | —CH₂CH₃ | —CH₃ | —CH₃ |
| 571 | —OCH₃ | —OC(O)H | —CH₃ | —H | —H | —CH₃ | —CH₃ | —H | —CH₃ | —CH₃ |
| 572 | —OCH₃ | —OC(O)H | —CH₃ | —H | —H | —CH₃ | —CH₃ | —H | —CH₂CH₃ | —CH₃ |
| 573 | —OCH₃ | —OC(O)H | —CH₃ | —H | —H | —CH₃ | —CH₃ | —CH₃ | —CH₃ | —CH₃ |
| 574 | —OCH₃ | —OC(O)H | —CH₃ | —H | —H | —CH₃ | —CH₃ | —CH₃ | —CH₂CH₃ | —CH₃ |
| 575 | —OCH₃ | —OC(O)H | —CH₃ | —H | —H | —CH₃ | —CH₃ | —CH₂CH₃ | —CH₃ | —CH₃ |
| 576 | —OCH₃ | —OC(O)H | —CH₃ | —H | —H | —CH₃ | —CH₂CH₃ | —H | —CH₃ | —CH₃ |
| 577 | —OCH₃ | —OC(O)H | —CH₃ | —H | —H | —CH₃ | —CH₂CH₃ | —CH₃ | —CH₃ | —CH₃ |
| 578 | —OCH₃ | —OC(O)H | —CH₃ | —H | —H | —CH₂CH₃ | —H | —H | —CH₃ | —CH₃ |
| 579 | —OCH₃ | —OC(O)H | —CH₃ | —H | —H | —CH₂CH₃ | —H | —CH₃ | —CH₃ | —CH₃ |
| 580 | —OCH₃ | —OC(O)H | —CH₃ | —H | —H | —CH₂CH₃ | —CH₃ | —H | —CH₃ | —CH₃ |
| 581 | —OCH₃ | —OC(O)H | —CH₃ | —H | —H | —CH₂CH₃ | —CH₃ | —CH₃ | —CH₃ | —CH₃ |
| 582 | —OCH₃ | —OC(O)H | —CH₃ | —H | —CH₃ | —CH₃ | —H | —H | —CH₃ | —CH₃ |
| 583 | —OCH₃ | —OC(O)H | —CH₃ | —H | —CH₃ | —CH₃ | —H | —H | —CH₂CH₃ | —CH₃ |
| 584 | —OCH₃ | —OC(O)H | —CH₃ | —H | —CH₃ | —CH₃ | —H | —CH₃ | —CH₃ | —CH₃ |
| 585 | —OCH₃ | —OC(O)H | —CH₃ | —H | —CH₃ | —CH₃ | —H | —CH₃ | —CH₂CH₃ | —CH₃ |
| 586 | —OCH₃ | —OC(O)H | —CH₃ | —H | —CH₃ | —CH₃ | —H | —CH₂CH₃ | —CH₃ | —CH₃ |
| 587 | —OCH₃ | —OC(O)H | —CH₃ | —H | —CH₃ | —CH₃ | —CH₃ | —H | —CH₃ | —CH₃ |
| 588 | —OCH₃ | —OC(O)H | —CH₃ | —H | —CH₃ | —CH₃ | —CH₃ | —H | —CH₂CH₃ | —CH₃ |
| 589 | —OCH₃ | —OC(O)H | —CH₃ | —H | —CH₃ | —CH₃ | —CH₃ | —CH₃ | —CH₃ | —CH₃ |
| 590 | —OCH₃ | —OC(O)H | —CH₃ | —H | —CH₃ | —CH₃ | —CH₃ | —CH₃ | —CH₂CH₃ | —CH₃ |
| 591 | —OCH₃ | —OC(O)H | —CH₃ | —H | —CH₃ | —CH₃ | —CH₃ | —CH₂CH₃ | —CH₃ | —CH₃ |
| 592 | —OCH₃ | —OC(O)H | —CH₃ | —H | —CH₃ | —CH₃ | —CH₂CH₃ | —H | —CH₃ | —CH₃ |
| 593 | —OCH₃ | —OC(O)H | —CH₃ | —H | —CH₃ | —CH₃ | —CH₂CH₃ | —CH₃ | —CH₃ | —CH₃ |
| 594 | —OCH₃ | —OC(O)H | —CH₃ | —H | —CH₃ | —CH₂CH₃ | —H | —H | —CH₃ | —CH₃ |
| 595 | —OCH₃ | —OC(O)H | —CH₃ | —H | —CH₃ | —CH₂CH₃ | —H | —CH₃ | —CH₃ | —CH₃ |
| 596 | —OCH₃ | —OC(O)H | —CH₃ | —H | —CH₃ | —CH₂CH₃ | —CH₃ | —H | —CH₃ | —CH₃ |
| 597 | —OCH₃ | —OC(O)H | —CH₃ | —H | —CH₃ | —CH₂CH₃ | —CH₃ | —CH₃ | —CH₃ | —CH₃ |
| 598 | —OCH₃ | —OC(O)H | —CH₃ | —H | —CH₃ | —CH₂CH₃ | —H | —H | —CH₃ | —CH₃ |
| 599 | —OCH₃ | —OC(O)H | —CH₃ | —H | —CH₃ | —CH₂CH₃ | —H | —H | —CH₃ | —CH₃ |
| 600 | —OCH₃ | —OC(O)H | —CH₃ | —H | —CH₃ | —CH₂CH₃ | —CH₃ | —H | —CH₃ | —CH₃ |
| 601 | —OCH₃ | —OC(O)H | —CH₃ | —H | —CH₃ | —CH₂CH₃ | —CH₃ | —CH₃ | —CH₃ | —CH₃ |
| 602 | —OCH₃ | —OC(O)H | —CH₃ | —H | —CH₃ | —CH₃ | —H | —H | —H | —CH₃ |
| 603 | —OCH₃ | —OC(O)H | —CH₃ | —H | —CH₃ | —CH₂CH₃ | —H | —H | —H | —CH₃ |
| 604 | —OCH₃ | —OC(O)H | —CH₃ | —H | —CH₃ | —CH₃ | —H | —CH₃ | —H | —CH₃ |
| 605 | —OCH₃ | —OC(O)H | —CH₃ | —H | —CH₃ | —CH₂CH₃ | —H | —CH₃ | —H | —CH₃ |
| 606 | —OCH₃ | —OC(O)H | —CH₃ | —H | —CH₃ | —CH₃ | —H | —CH₂CH₃ | —H | —CH₃ |
| 607 | —OCH₃ | —OC(O)H | —CH₃ | —H | —CH₃ | —CH₃ | —CH₃ | —H | —H | —CH₃ |
| 608 | —OCH₃ | —OC(O)H | —CH₃ | —H | —CH₃ | —CH₂CH₃ | —CH₃ | —H | —H | —CH₃ |
| 609 | —OCH₃ | —OC(O)H | —CH₃ | —H | —CH₃ | —CH₃ | —CH₃ | —CH₃ | —H | —CH₃ |
| 610 | —OCH₃ | —OC(O)H | —CH₃ | —H | —CH₃ | —CH₂CH₃ | —CH₃ | —CH₃ | —H | —CH₃ |
| 611 | —OCH₃ | —OC(O)H | —CH₃ | —H | —CH₃ | —CH₃ | —CH₃ | —CH₂CH₃ | —H | —CH₃ |
| 612 | —OCH₃ | —OC(O)H | —CH₃ | —H | —CH₃ | —CH₃ | —CH₂CH₃ | —H | —H | —CH₃ |
| 613 | —OCH₃ | —OC(O)H | —CH₃ | —H | —CH₃ | —CH₃ | —CH₂CH₃ | —CH₃ | —H | —CH₃ |
| 614 | —OCH₃ | —OC(O)H | —CH₂CH₃ | —H | —H | —CH₃ | —H | —H | —CH₃ | —CH₃ |
| 615 | —OCH₃ | —OC(O)H | —CH₂CH₃ | —H | —H | —CH₃ | —H | —H | —CH₂CH₃ | —CH₃ |
| 616 | —OCH₃ | —OC(O)H | —CH₂CH₃ | —H | —H | —CH₃ | —H | —CH₃ | —CH₃ | —CH₃ |
| 617 | —OCH₃ | —OC(O)H | —CH₂CH₃ | —H | —H | —CH₃ | —H | —CH₃ | —CH₂CH₃ | —CH₃ |
| 618 | —OCH₃ | —OC(O)H | —CH₂CH₃ | —H | —H | —CH₃ | —H | —CH₂CH₃ | —CH₃ | —CH₃ |
| 619 | —OCH₃ | —OC(O)H | —CH₂CH₃ | —H | —H | —CH₃ | —CH₃ | —H | —CH₃ | —CH₃ |
| 620 | —OCH₃ | —OC(O)H | —CH₂CH₃ | —H | —H | —CH₃ | —CH₃ | —H | —CH₂CH₃ | —CH₃ |
| 621 | —OCH₃ | —OC(O)H | —CH₂CH₃ | —H | —H | —CH₃ | —CH₃ | —CH₃ | —CH₃ | —CH₃ |
| 622 | —OCH₃ | —OC(O)H | —CH₂CH₃ | —H | —H | —CH₃ | —CH₃ | —CH₃ | —CH₂CH₃ | —CH₃ |
| 623 | —OCH₃ | —OC(O)H | —CH₂CH₃ | —H | —H | —CH₃ | —CH₃ | —CH₂CH₃ | —CH₃ | —CH₃ |
| 624 | —OCH₃ | —OC(O)H | —CH₂CH₃ | —H | —H | —CH₃ | —CH₂CH₃ | —H | —CH₃ | —CH₃ |
| 625 | —OCH₃ | —OC(O)H | —CH₂CH₃ | —H | —H | —CH₃ | —CH₂CH₃ | —CH₃ | —CH₃ | —CH₃ |
| 626 | —OCH₃ | —OC(O)H | —CH₂CH₃ | —H | —H | —CH₂CH₃ | —H | —H | —CH₃ | —CH₃ |
| 627 | —OCH₃ | —OC(O)H | —CH₂CH₃ | —H | —H | —CH₂CH₃ | —H | —CH₃ | —CH₃ | —CH₃ |
| 628 | —OCH₃ | —OC(O)H | —CH₂CH₃ | —H | —H | —CH₂CH₃ | —CH₃ | —H | —CH₃ | —CH₃ |
| 629 | —OCH₃ | —OC(O)H | —CH₂CH₃ | —H | —H | —CH₂CH₃ | —CH₃ | —CH₃ | —CH₃ | —CH₃ |
| 630 | —OCH₃ | —OC(O)H | —CH₂CH₃ | —H | —CH₃ | —CH₃ | —H | —H | —CH₃ | —CH₃ |
| 631 | —OCH₃ | —OC(O)H | —CH₂CH₃ | —H | —CH₃ | —CH₃ | —H | —H | —CH₂CH₃ | —CH₃ |

-continued

| | | | | | | | | | |
|---|---|---|---|---|---|---|---|---|---|
| 632 | —OCH$_3$ | —OC(O)H | —CH$_2$CH$_3$ | —H | —CH$_3$ | —CH$_3$ | —H | —CH$_3$ | —CH$_3$ | —CH$_3$ |
| 633 | —OCH$_3$ | —OC(O)H | —CH$_2$CH$_3$ | —H | —CH$_3$ | —CH$_3$ | —H | —CH$_3$ | —CH$_2$CH$_3$ | —CH$_3$ |
| 634 | —OCH$_3$ | —OC(O)H | —CH$_2$CH$_3$ | —H | —CH$_3$ | —CH$_3$ | —H | —CH$_2$CH$_3$ | —CH$_3$ | —CH$_3$ |
| 635 | —OCH$_3$ | —OC(O)H | —CH$_2$CH$_3$ | —H | —CH$_3$ | —CH$_3$ | —CH$_3$ | —H | —CH$_3$ | —CH$_3$ |
| 636 | —OCH$_3$ | —OC(O)H | —CH$_2$CH$_3$ | —H | —CH$_3$ | —CH$_3$ | —CH$_3$ | —H | —CH$_2$CH$_3$ | —CH$_3$ |
| 637 | —OCH$_3$ | —OC(O)H | —CH$_2$CH$_3$ | —H | —CH$_3$ | —CH$_3$ | —CH$_3$ | —CH$_3$ | —CH$_3$ | —CH$_3$ |
| 638 | —OCH$_3$ | —OC(O)H | —CH$_2$CH$_3$ | —H | —CH$_3$ | —CH$_3$ | —CH$_3$ | —CH$_3$ | —CH$_2$CH$_3$ | —CH$_3$ |
| 639 | —OCH$_3$ | —OC(O)H | —CH$_2$CH$_3$ | —H | —CH$_3$ | —CH$_3$ | —CH$_3$ | —CH$_2$CH$_3$ | —CH$_3$ | —CH$_3$ |
| 640 | —OCH$_3$ | —OC(O)H | —CH$_2$CH$_3$ | —H | —CH$_3$ | —CH$_3$ | —CH$_2$CH$_3$ | —H | —CH$_3$ | —CH$_3$ |
| 641 | —OCH$_3$ | —OC(O)H | —CH$_2$CH$_3$ | —H | —CH$_3$ | —CH$_3$ | —CH$_2$CH$_3$ | —CH$_3$ | —CH$_3$ | —CH$_3$ |
| 642 | —OCH$_3$ | —OC(O)H | —CH$_2$CH$_3$ | —H | —CH$_3$ | —CH$_2$CH$_3$ | —H | —H | —CH$_3$ | —CH$_3$ |
| 643 | —OCH$_3$ | —OC(O)H | —CH$_2$CH$_3$ | —H | —CH$_3$ | —CH$_2$CH$_3$ | —H | —CH$_3$ | —CH$_3$ | —CH$_3$ |
| 644 | —OCH$_3$ | —OC(O)H | —CH$_2$CH$_3$ | —H | —CH$_3$ | —CH$_2$CH$_3$ | —CH$_3$ | —H | —CH$_3$ | —CH$_3$ |
| 645 | —OCH$_3$ | —OC(O)H | —CH$_2$CH$_3$ | —H | —CH$_3$ | —CH$_2$CH$_3$ | —CH$_3$ | —CH$_3$ | —CH$_3$ | —CH$_3$ |
| 646 | —OCH$_3$ | —OC(O)H | —CH$_2$CH$_3$ | —H | —CH$_3$ | —CH$_2$CH$_3$ | —H | —H | —CH$_3$ | —CH$_3$ |
| 647 | —OCH$_3$ | —OC(O)H | —CH$_2$CH$_3$ | —H | —CH$_3$ | —CH$_2$CH$_3$ | —H | —CH$_3$ | —CH$_3$ | —CH$_3$ |
| 648 | —OCH$_3$ | —OC(O)H | —CH$_2$CH$_3$ | —H | —CH$_3$ | —CH$_2$CH$_3$ | —CH$_3$ | —H | —CH$_3$ | —CH$_3$ |
| 649 | —OCH$_3$ | —OC(O)H | —CH$_2$CH$_3$ | —H | —CH$_3$ | —CH$_2$CH$_3$ | —CH$_3$ | —CH$_3$ | —CH$_3$ | —CH$_3$ |
| 650 | —OCH$_3$ | —OC(O)H | —CH$_2$CH$_3$ | —H | —CH$_3$ | —CH$_3$ | —H | —H | —H | —CH$_3$ |
| 651 | —OCH$_3$ | —OC(O)H | —CH$_2$CH$_3$ | —H | —CH$_3$ | —CH$_2$CH$_3$ | —H | —H | —H | —CH$_3$ |
| 652 | —OCH$_3$ | —OC(O)H | —CH$_2$CH$_3$ | —H | —CH$_3$ | —CH$_3$ | —H | —CH$_3$ | —H | —CH$_3$ |
| 653 | —OCH$_3$ | —OC(O)H | —CH$_2$CH$_3$ | —H | —CH$_3$ | —CH$_2$CH$_3$ | —H | —CH$_3$ | —H | —CH$_3$ |
| 654 | —OCH$_3$ | —OC(O)H | —CH$_2$CH$_3$ | —H | —CH$_3$ | —CH$_3$ | —H | —CH$_2$CH$_3$ | —H | —CH$_3$ |
| 655 | —OCH$_3$ | —OC(O)H | —CH$_2$CH$_3$ | —H | —CH$_3$ | —CH$_3$ | —CH$_3$ | —H | —H | —CH$_3$ |
| 656 | —OCH$_3$ | —OC(O)H | —CH$_2$CH$_3$ | —H | —CH$_3$ | —CH$_2$CH$_3$ | —CH$_3$ | —H | —H | —CH$_3$ |
| 657 | —OCH$_3$ | —OC(O)H | —CH$_2$CH$_3$ | —H | —CH$_3$ | —CH$_3$ | —CH$_3$ | —CH$_3$ | —H | —CH$_3$ |
| 658 | —OCH$_3$ | —OC(O)H | —CH$_2$CH$_3$ | —H | —CH$_3$ | —CH$_2$CH$_3$ | —CH$_3$ | —CH$_3$ | —H | —CH$_3$ |
| 659 | —OCH$_3$ | —OC(O)H | —CH$_2$CH$_3$ | —H | —CH$_3$ | —CH$_3$ | —CH$_3$ | —CH$_2$CH$_3$ | —H | —CH$_3$ |
| 660 | —OCH$_3$ | —OC(O)H | —CH$_2$CH$_3$ | —H | —CH$_3$ | —CH$_3$ | —CH$_2$CH$_3$ | —H | —H | —CH$_3$ |
| 661 | —OCH$_3$ | —OC(O)H | —CH$_2$CH$_3$ | —H | —CH$_3$ | —CH$_3$ | —CH$_2$CH$_3$ | —CH$_3$ | —H | —CH$_3$ |
| 662 | —OCH$_3$ | —OC(O)H | —OCH$_3$ | —H | —H | —CH$_3$ | —H | —H | —CH$_3$ | —CH$_3$ |
| 663 | —OCH$_3$ | —OC(O)H | —OCH$_3$ | —H | —H | —CH$_3$ | —H | —H | —CH$_2$CH$_3$ | —CH$_3$ |
| 664 | —OCH$_3$ | —OC(O)H | —OCH$_3$ | —H | —H | —CH$_3$ | —H | —CH$_3$ | —CH$_3$ | —CH$_3$ |
| 665 | —OCH$_3$ | —OC(O)H | —OCH$_3$ | —H | —H | —CH$_3$ | —H | —CH$_3$ | —CH$_2$CH$_3$ | —CH$_3$ |
| 666 | —OCH$_3$ | —OC(O)H | —OCH$_3$ | —H | —H | —CH$_3$ | —H | —CH$_2$CH$_3$ | —CH$_3$ | —CH$_3$ |
| 667 | —OCH$_3$ | —OC(O)H | —OCH$_3$ | —H | —H | —CH$_3$ | —CH$_3$ | —H | —CH$_3$ | —CH$_3$ |
| 668 | —OCH$_3$ | —OC(O)H | —OCH$_3$ | —H | —H | —CH$_3$ | —CH$_3$ | —H | —CH$_2$CH$_3$ | —CH$_3$ |
| 669 | —OCH$_3$ | —OC(O)H | —OCH$_3$ | —H | —H | —CH$_3$ | —CH$_3$ | —CH$_3$ | —CH$_3$ | —CH$_3$ |
| 670 | —OCH$_3$ | —OC(O)H | —OCH$_3$ | —H | —H | —CH$_3$ | —CH$_3$ | —CH$_3$ | —CH$_2$CH$_3$ | —CH$_3$ |
| 671 | —OCH$_3$ | —OC(O)H | —OCH$_3$ | —H | —H | —CH$_3$ | —CH$_3$ | —CH$_2$CH$_3$ | —CH$_3$ | —CH$_3$ |
| 672 | —OCH$_3$ | —OC(O)H | —OCH$_3$ | —H | —H | —CH$_3$ | —CH$_2$CH$_3$ | —H | —CH$_3$ | —CH$_3$ |
| 673 | —OCH$_3$ | —OC(O)H | —OCH$_3$ | —H | —H | —CH$_3$ | —CH$_2$CH$_3$ | —CH$_3$ | —CH$_3$ | —CH$_3$ |
| 674 | —OCH$_3$ | —OC(O)H | —OCH$_3$ | —H | —H | —CH$_2$CH$_3$ | —H | —H | —CH$_3$ | —CH$_3$ |
| 675 | —OCH$_3$ | —OC(O)H | —OCH$_3$ | —H | —H | —CH$_2$CH$_3$ | —H | —CH$_3$ | —CH$_3$ | —CH$_3$ |
| 676 | —OCH$_3$ | —OC(O)H | —OCH$_3$ | —H | —H | —CH$_2$CH$_3$ | —CH$_3$ | —H | —CH$_3$ | —CH$_3$ |
| 677 | —OCH$_3$ | —OC(O)H | —OCH$_3$ | —H | —H | —CH$_2$CH$_3$ | —CH$_3$ | —CH$_3$ | —CH$_3$ | —CH$_3$ |
| 678 | —OCH$_3$ | —OC(O)H | —OCH$_3$ | —H | —CH$_3$ | —CH$_3$ | —H | —H | —CH$_3$ | —CH$_3$ |
| 679 | —OCH$_3$ | —OC(O)H | —OCH$_3$ | —H | —CH$_3$ | —CH$_3$ | —H | —H | —CH$_2$CH$_3$ | —CH$_3$ |
| 680 | —OCH$_3$ | —OC(O)H | —OCH$_3$ | —H | —CH$_3$ | —CH$_3$ | —H | —CH$_3$ | —CH$_3$ | —CH$_3$ |
| 681 | —OCH$_3$ | —OC(O)H | —OCH$_3$ | —H | —CH$_3$ | —CH$_3$ | —H | —CH$_3$ | —CH$_2$CH$_3$ | —CH$_3$ |
| 682 | —OCH$_3$ | —OC(O)H | —OCH$_3$ | —H | —CH$_3$ | —CH$_3$ | —H | —CH$_2$CH$_3$ | —CH$_3$ | —CH$_3$ |
| 683 | —OCH$_3$ | —OC(O)H | —OCH$_3$ | —H | —CH$_3$ | —CH$_3$ | —CH$_3$ | —H | —CH$_3$ | —CH$_3$ |
| 684 | —OCH$_3$ | —OC(O)H | —OCH$_3$ | —H | —CH$_3$ | —CH$_3$ | —CH$_3$ | —H | —CH$_2$CH$_3$ | —CH$_3$ |
| 685 | —OCH$_3$ | —OC(O)H | —OCH$_3$ | —H | —CH$_3$ | —CH$_3$ | —CH$_3$ | —CH$_3$ | —CH$_3$ | —CH$_3$ |
| 686 | —OCH$_3$ | —OC(O)H | —OCH$_3$ | —H | —CH$_3$ | —CH$_3$ | —CH$_3$ | —CH$_3$ | —CH$_2$CH$_3$ | —CH$_3$ |
| 687 | —OCH$_3$ | —OC(O)H | —OCH$_3$ | —H | —CH$_3$ | —CH$_3$ | —CH$_3$ | —CH$_2$CH$_3$ | —CH$_3$ | —CH$_3$ |
| 688 | —OCH$_3$ | —OC(O)H | —OCH$_3$ | —H | —CH$_3$ | —CH$_3$ | —CH$_2$CH$_3$ | —H | —CH$_3$ | —CH$_3$ |
| 689 | —OCH$_3$ | —OC(O)H | —OCH$_3$ | —H | —CH$_3$ | —CH$_3$ | —CH$_2$CH$_3$ | —CH$_3$ | —CH$_3$ | —CH$_3$ |
| 690 | —OCH$_3$ | —OC(O)H | —OCH$_3$ | —H | —CH$_3$ | —CH$_2$CH$_3$ | —H | —H | —CH$_3$ | —CH$_3$ |
| 691 | —OCH$_3$ | —OC(O)H | —OCH$_3$ | —H | —CH$_3$ | —CH$_2$CH$_3$ | —H | —CH$_3$ | —CH$_3$ | —CH$_3$ |
| 692 | —OCH$_3$ | —OC(O)H | —OCH$_3$ | —H | —CH$_3$ | —CH$_2$CH$_3$ | —CH$_3$ | —H | —CH$_3$ | —CH$_3$ |
| 693 | —OCH$_3$ | —OC(O)H | —OCH$_3$ | —H | —CH$_3$ | —CH$_2$CH$_3$ | —CH$_3$ | —CH$_3$ | —CH$_3$ | —CH$_3$ |
| 694 | —OCH$_3$ | —OC(O)H | —OCH$_3$ | —H | —CH$_3$ | —CH$_2$CH$_3$ | —H | —H | —CH$_3$ | —CH$_3$ |
| 695 | —OCH$_3$ | —OC(O)H | —OCH$_3$ | —H | —CH$_3$ | —CH$_2$CH$_3$ | —H | —CH$_3$ | —CH$_3$ | —CH$_3$ |
| 696 | —OCH$_3$ | —OC(O)H | —OCH$_3$ | —H | —CH$_3$ | —CH$_2$CH$_3$ | —CH$_3$ | —H | —CH$_3$ | —CH$_3$ |
| 697 | —OCH$_3$ | —OC(O)H | —OCH$_3$ | —H | —CH$_3$ | —CH$_2$CH$_3$ | —CH$_3$ | —CH$_3$ | —CH$_3$ | —CH$_3$ |
| 698 | —OCH$_3$ | —OC(O)H | —OCH$_3$ | —H | —CH$_3$ | —CH$_3$ | —H | —H | —H | —CH$_3$ |
| 699 | —OCH$_3$ | —OC(O)H | —OCH$_3$ | —H | —CH$_3$ | —CH$_2$CH$_3$ | —H | —H | —H | —CH$_3$ |
| 700 | —OCH$_3$ | —OC(O)H | —OCH$_3$ | —H | —CH$_3$ | —CH$_3$ | —H | —CH$_3$ | —H | —CH$_3$ |
| 701 | —OCH$_3$ | —OC(O)H | —OCH$_3$ | —H | —CH$_3$ | —CH$_2$CH$_3$ | —H | —CH$_3$ | —H | —CH$_3$ |
| 702 | —OCH$_3$ | —OC(O)H | —OCH$_3$ | —H | —CH$_3$ | —CH$_3$ | —H | —CH$_2$CH$_3$ | —H | —CH$_3$ |
| 703 | —OCH$_3$ | —OC(O)H | —OCH$_3$ | —H | —CH$_3$ | —CH$_3$ | —CH$_3$ | —H | —H | —CH$_3$ |
| 704 | —OCH$_3$ | —OC(O)H | —OCH$_3$ | —H | —CH$_3$ | —CH$_2$CH$_3$ | —CH$_3$ | —H | —H | —CH$_3$ |
| 705 | —OCH$_3$ | —OC(O)H | —OCH$_3$ | —H | —CH$_3$ | —CH$_3$ | —CH$_3$ | —CH$_3$ | —H | —CH$_3$ |
| 706 | —OCH$_3$ | —OC(O)H | —OCH$_3$ | —H | —CH$_3$ | —CH$_2$CH$_3$ | —CH$_3$ | —CH$_3$ | —H | —CH$_3$ |
| 707 | —OCH$_3$ | —OC(O)H | —OCH$_3$ | —H | —CH$_3$ | —CH$_3$ | —CH$_3$ | —CH$_2$CH$_3$ | —H | —CH$_3$ |
| 708 | —OCH$_3$ | —OC(O)H | —OCH$_3$ | —H | —CH$_3$ | —CH$_3$ | —CH$_2$CH$_3$ | —H | —H | —CH$_3$ |
| 709 | —OCH$_3$ | —OC(O)H | —OCH$_3$ | —H | —CH$_3$ | —CH$_3$ | —CH$_2$CH$_3$ | —CH$_3$ | —H | —CH$_3$ |
| 710 | —OH | —OC(O)H | —CH$_3$ | —H | —H | —CH$_3$ | —H | —H | —CH$_3$ | —CH$_3$ |
| 711 | —OH | —OC(O)H | —CH$_3$ | —H | —H | —CH$_3$ | —H | —H | —CH$_2$CH$_3$ | —CH$_3$ |

| | | | | | | | | | |
|---|---|---|---|---|---|---|---|---|---|
| 712 | —OH | —OC(O)H | —CH₃ | —H | —H | —CH₃ | —H | —CH₃ | —CH₃ | —CH₃ |
| 713 | —OH | —OC(O)H | —CH₃ | —H | —H | —CH₃ | —H | —CH₃ | —CH₂CH₃ | —CH₃ |
| 714 | —OH | —OC(O)H | —CH₃ | —H | —H | —CH₃ | —H | —CH₂CH₃ | —CH₃ | —CH₃ |
| 715 | —OH | —OC(O)H | —CH₃ | —H | —H | —CH₃ | —CH₃ | —H | —CH₃ | —CH₃ |
| 716 | —OH | —OC(O)H | —CH₃ | —H | —H | —CH₃ | —CH₃ | —H | —CH₂CH₃ | —CH₃ |
| 717 | —OH | —OC(O)H | —CH₃ | —H | —H | —CH₃ | —CH₃ | —CH₃ | —CH₃ | —CH₃ |
| 718 | —OH | —OC(O)H | —CH₃ | —H | —H | —CH₃ | —CH₃ | —CH₃ | —CH₂CH₃ | —CH₃ |
| 719 | —OH | —OC(O)H | —CH₃ | —H | —H | —CH₃ | —CH₃ | —CH₂CH₃ | —CH₃ | —CH₃ |
| 720 | —OH | —OC(O)H | —CH₃ | —H | —H | —CH₃ | —CH₂CH₃ | —H | —CH₃ | —CH₃ |
| 721 | —OH | —OC(O)H | —CH₃ | —H | —H | —CH₃ | —CH₂CH₃ | —CH₃ | —CH₃ | —CH₃ |
| 722 | —OH | —OC(O)H | —CH₃ | —H | —H | —CH₂CH₃ | —H | —H | —CH₃ | —CH₃ |
| 723 | —OH | —OC(O)H | —CH₃ | —H | —H | —CH₂CH₃ | —H | —CH₃ | —CH₃ | —CH₃ |
| 724 | —OH | —OC(O)H | —CH₃ | —H | —H | —CH₂CH₃ | —CH₃ | —H | —CH₃ | —CH₃ |
| 725 | —OH | —OC(O)H | —CH₃ | —H | —H | —CH₂CH₃ | —CH₃ | —CH₃ | —CH₃ | —CH₃ |
| 726 | —OH | —OC(O)H | —CH₃ | —H | —CH₃ | —CH₃ | —H | —H | —CH₃ | —CH₃ |
| 727 | —OH | —OC(O)H | —CH₃ | —H | —CH₃ | —CH₃ | —H | —H | —CH₂CH₃ | —CH₃ |
| 728 | —OH | —OC(O)H | —CH₃ | —H | —CH₃ | —CH₃ | —H | —CH₃ | —CH₃ | —CH₃ |
| 729 | —OH | —OC(O)H | —CH₃ | —H | —CH₃ | —CH₃ | —H | —CH₃ | —CH₂CH₃ | —CH₃ |
| 730 | —OH | —OC(O)H | —CH₃ | —H | —CH₃ | —CH₃ | —H | —CH₂CH₃ | —CH₃ | —CH₃ |
| 731 | —OH | —OC(O)H | —CH₃ | —H | —CH₃ | —CH₃ | —CH₃ | —H | —CH₃ | —CH₃ |
| 732 | —OH | —OC(O)H | —CH₃ | —H | —CH₃ | —CH₃ | —CH₃ | —H | —CH₂CH₃ | —CH₃ |
| 733 | —OH | —OC(O)H | —CH₃ | —H | —CH₃ | —CH₃ | —CH₃ | —CH₃ | —CH₃ | —CH₃ |
| 734 | —OH | —OC(O)H | —CH₃ | —H | —CH₃ | —CH₃ | —CH₃ | —CH₃ | —CH₂CH₃ | —CH₃ |
| 735 | —OH | —OC(O)H | —CH₃ | —H | —CH₃ | —CH₃ | —CH₃ | —CH₂CH₃ | —CH₃ | —CH₃ |
| 736 | —OH | —OC(O)H | —CH₃ | —H | —CH₃ | —CH₃ | —CH₂CH₃ | —H | —CH₃ | —CH₃ |
| 737 | —OH | —OC(O)H | —CH₃ | —H | —CH₃ | —CH₃ | —CH₂CH₃ | —CH₃ | —CH₃ | —CH₃ |
| 738 | —OH | —OC(O)H | —CH₃ | —H | —CH₃ | —CH₂CH₃ | —H | —H | —CH₃ | —CH₃ |
| 739 | —OH | —OC(O)H | —CH₃ | —H | —CH₃ | —CH₂CH₃ | —H | —CH₃ | —CH₃ | —CH₃ |
| 740 | —OH | —OC(O)H | —CH₃ | —H | —CH₃ | —CH₂CH₃ | —CH₃ | —H | —CH₃ | —CH₃ |
| 741 | —OH | —OC(O)H | —CH₃ | —H | —CH₃ | —CH₂CH₃ | —CH₃ | —CH₃ | —CH₃ | —CH₃ |
| 742 | —OH | —OC(O)H | —CH₃ | —H | —CH₃ | —CH₂CH₃ | —H | —H | —CH₃ | —CH₃ |
| 743 | —OH | —OC(O)H | —CH₃ | —H | —CH₃ | —CH₂CH₃ | —H | —CH₃ | —CH₃ | —CH₃ |
| 744 | —OH | —OC(O)H | —CH₃ | —H | —CH₃ | —CH₂CH₃ | —CH₃ | —H | —CH₃ | —CH₃ |
| 745 | —OH | —OC(O)H | —CH₃ | —H | —CH₃ | —CH₂CH₃ | —CH₃ | —CH₃ | —CH₃ | —CH₃ |
| 746 | —OH | —OC(O)H | —CH₃ | —H | —CH₃ | —CH₃ | —H | —H | —H | —CH₃ |
| 747 | —OH | —OC(O)H | —CH₃ | —H | —CH₃ | —CH₂CH₃ | —H | —H | —H | —CH₃ |
| 748 | —OH | —OC(O)H | —CH₃ | —H | —CH₃ | —CH₃ | —H | —CH₃ | —H | —CH₃ |
| 749 | —OH | —OC(O)H | —CH₃ | —H | —CH₃ | —CH₂CH₃ | —H | —CH₃ | —H | —CH₃ |
| 750 | —OH | —OC(O)H | —CH₃ | —H | —CH₃ | —CH₃ | —H | —CH₂CH₃ | —H | —CH₃ |
| 751 | —OH | —OC(O)H | —CH₃ | —H | —CH₃ | —CH₃ | —CH₃ | —H | —H | —CH₃ |
| 752 | —OH | —OC(O)H | —CH₃ | —H | —CH₃ | —CH₂CH₃ | —CH₃ | —H | —H | —CH₃ |
| 753 | —OH | —OC(O)H | —CH₃ | —H | —CH₃ | —CH₃ | —CH₃ | —CH₃ | —H | —CH₃ |
| 754 | —OH | —OC(O)H | —CH₃ | —H | —CH₃ | —CH₂CH₃ | —CH₃ | —CH₃ | —H | —CH₃ |
| 755 | —OH | —OC(O)H | —CH₃ | —H | —CH₃ | —CH₃ | —CH₃ | —CH₂CH₃ | —H | —CH₃ |
| 756 | —OH | —OC(O)H | —CH₃ | —H | —CH₃ | —CH₃ | —CH₂CH₃ | —H | —H | —CH₃ |
| 757 | —OH | —OC(O)H | —CH₃ | —H | —CH₃ | —CH₃ | —CH₂CH₃ | —CH₃ | —H | —CH₃ |
| 758 | —OH | —OC(O)H | —CH₂CH₃ | —H | —H | —CH₃ | —H | —H | —CH₃ | —CH₃ |
| 759 | —OH | —OC(O)H | —CH₂CH₃ | —H | —H | —CH₃ | —H | —H | —CH₂CH₃ | —CH₃ |
| 760 | —OH | —OC(O)H | —CH₂CH₃ | —H | —H | —CH₃ | —H | —CH₃ | —CH₃ | —CH₃ |
| 761 | —OH | —OC(O)H | —CH₂CH₃ | —H | —H | —CH₃ | —H | —CH₃ | —CH₂CH₃ | —CH₃ |
| 762 | —OH | —OC(O)H | —CH₂CH₃ | —H | —H | —CH₃ | —H | —CH₂CH₃ | —CH₃ | —CH₃ |
| 763 | —OH | —OC(O)H | —CH₂CH₃ | —H | —H | —CH₃ | —CH₃ | —H | —CH₃ | —CH₃ |
| 764 | —OH | —OC(O)H | —CH₂CH₃ | —H | —H | —CH₃ | —CH₃ | —H | —CH₂CH₃ | —CH₃ |
| 765 | —OH | —OC(O)H | —CH₂CH₃ | —H | —H | —CH₃ | —CH₃ | —CH₃ | —CH₃ | —CH₃ |
| 766 | —OH | —OC(O)H | —CH₂CH₃ | —H | —H | —CH₃ | —CH₃ | —CH₃ | —CH₂CH₃ | —CH₃ |
| 767 | —OH | —OC(O)H | —CH₂CH₃ | —H | —H | —CH₃ | —CH₃ | —CH₂CH₃ | —CH₃ | —CH₃ |
| 768 | —OH | —OC(O)H | —CH₂CH₃ | —H | —H | —CH₃ | —CH₂CH₃ | —H | —CH₃ | —CH₃ |
| 769 | —OH | —OC(O)H | —CH₂CH₃ | —H | —H | —CH₃ | —CH₂CH₃ | —CH₃ | —CH₃ | —CH₃ |
| 770 | —OH | —OC(O)H | —CH₂CH₃ | —H | —H | —CH₂CH₃ | —H | —H | —CH₃ | —CH₃ |
| 771 | —OH | —OC(O)H | —CH₂CH₃ | —H | —H | —CH₂CH₃ | —H | —CH₃ | —CH₃ | —CH₃ |
| 772 | —OH | —OC(O)H | —CH₂CH₃ | —H | —H | —CH₂CH₃ | —CH₃ | —H | —CH₃ | —CH₃ |
| 773 | —OH | —OC(O)H | —CH₂CH₃ | —H | —H | —CH₂CH₃ | —CH₃ | —CH₃ | —CH₃ | —CH₃ |
| 774 | —OH | —OC(O)H | —CH₂CH₃ | —H | —CH₃ | —CH₃ | —H | —H | —CH₃ | —CH₃ |
| 775 | —OH | —OC(O)H | —CH₂CH₃ | —H | —CH₃ | —CH₃ | —H | —H | —CH₂CH₃ | —CH₃ |
| 776 | —OH | —OC(O)H | —CH₂CH₃ | —H | —CH₃ | —CH₃ | —H | —CH₃ | —CH₃ | —CH₃ |
| 777 | —OH | —OC(O)H | —CH₂CH₃ | —H | —CH₃ | —CH₃ | —H | —CH₃ | —CH₂CH₃ | —CH₃ |
| 778 | —OH | —OC(O)H | —CH₂CH₃ | —H | —CH₃ | —CH₃ | —H | —CH₂CH₃ | —CH₃ | —CH₃ |
| 779 | —OH | —OC(O)H | —CH₂CH₃ | —H | —CH₃ | —CH₃ | —CH₃ | —H | —CH₃ | —CH₃ |
| 780 | —OH | —OC(O)H | —CH₂CH₃ | —H | —CH₃ | —CH₃ | —CH₃ | —H | —CH₂CH₃ | —CH₃ |
| 781 | —OH | —OC(O)H | —CH₂CH₃ | —H | —CH₃ | —CH₃ | —CH₃ | —CH₃ | —CH₃ | —CH₃ |
| 782 | —OH | —OC(O)H | —CH₂CH₃ | —H | —CH₃ | —CH₃ | —CH₃ | —CH₃ | —CH₂CH₃ | —CH₃ |
| 783 | —OH | —OC(O)H | —CH₂CH₃ | —H | —CH₃ | —CH₃ | —CH₃ | —CH₂CH₃ | —CH₃ | —CH₃ |
| 784 | —OH | —OC(O)H | —CH₂CH₃ | —H | —CH₃ | —CH₃ | —CH₂CH₃ | —H | —CH₃ | —CH₃ |
| 785 | —OH | —OC(O)H | —CH₂CH₃ | —H | —CH₃ | —CH₃ | —CH₂CH₃ | —CH₃ | —CH₃ | —CH₃ |
| 786 | —OH | —OC(O)H | —CH₂CH₃ | —H | —CH₃ | —CH₂CH₃ | —H | —H | —CH₃ | —CH₃ |
| 787 | —OH | —OC(O)H | —CH₂CH₃ | —H | —CH₃ | —CH₂CH₃ | —H | —CH₃ | —CH₃ | —CH₃ |
| 788 | —OH | —OC(O)H | —CH₂CH₃ | —H | —CH₃ | —CH₂CH₃ | —CH₃ | —H | —CH₃ | —CH₃ |
| 789 | —OH | —OC(O)H | —CH₂CH₃ | —H | —CH₃ | —CH₂CH₃ | —CH₃ | —CH₃ | —CH₃ | —CH₃ |
| 790 | —OH | —OC(O)H | —CH₂CH₃ | —H | —CH₃ | —CH₂CH₃ | —H | —H | —CH₃ | —CH₃ |
| 791 | —OH | —OC(O)H | —CH₂CH₃ | —H | —CH₃ | —CH₂CH₃ | —H | —CH₃ | —CH₃ | —CH₃ |
| 792 | —OH | —OC(O)H | —CH₂CH₃ | —H | —CH₃ | —CH₂CH₃ | —CH₃ | —H | —CH₃ | —CH₃ |
| 793 | —OH | —OC(O)H | —CH₂CH₃ | —H | —CH₃ | —CH₂CH₃ | —CH₃ | —CH₃ | —CH₃ | —CH₃ |
| 794 | —OH | —OC(O)H | —CH₂CH₃ | —H | —CH₃ | —CH₃ | —H | —H | —H | —CH₃ |

-continued

| | | | | | | | | | |
|---|---|---|---|---|---|---|---|---|---|
| 795 | —OH | —OC(O)H | —CH₂CH₃ | —H | —CH₃ | —CH₂CH₃ | —H | —H | —H | —CH₃ |
| 796 | —OH | —OC(O)H | —CH₂CH₃ | —H | —CH₃ | —CH₂CH₃ | —H | —CH₃ | —H | —CH₃ |
| 797 | —OH | —OC(O)H | —CH₂CH₃ | —H | —CH₃ | —CH₂CH₃ | —H | —CH₃ | —H | —CH₃ |
| 798 | —OH | —OC(O)H | —CH₂CH₃ | —H | —CH₃ | —CH₃ | —H | —CH₂CH₃ | —H | —CH₃ |
| 799 | —OH | —OC(O)H | —CH₂CH₃ | —H | —CH₃ | —CH₃ | —CH₃ | —H | —H | —CH₃ |
| 800 | —OH | —OC(O)H | —CH₂CH₃ | —H | —CH₃ | —CH₂CH₃ | —CH₃ | —H | —H | —CH₃ |
| 801 | —OH | —OC(O)H | —CH₂CH₃ | —H | —CH₃ | —CH₃ | —CH₃ | —CH₃ | —H | —CH₃ |
| 802 | —OH | —OC(O)H | —CH₂CH₃ | —H | —CH₃ | —CH₂CH₃ | —CH₃ | —CH₃ | —H | —CH₃ |
| 803 | —OH | —OC(O)H | —CH₂CH₃ | —H | —CH₃ | —CH₃ | —CH₃ | —CH₂CH₃ | —H | —CH₃ |
| 804 | —OH | —OC(O)H | —CH₂CH₃ | —H | —CH₃ | —CH₃ | —CH₂CH₃ | —H | —H | —CH₃ |
| 805 | —OH | —OC(O)H | —CH₂CH₃ | —H | —CH₃ | —CH₃ | —CH₂CH₃ | —CH₃ | —H | —CH₃ |
| 806 | —H | —H | —OC(O)H | —(CH₂)₂— | —CH₃ | —H | —H | —H | —CH₃ | —CH₃ |
| 807 | —H | —H | —OC(O)H | —(CH₂)₂— | —CH₃ | —H | —H | —CH₂CH₃ | —CH₃ | —CH₃ |
| 808 | —H | —H | —OC(O)H | —(CH₂)₂— | —CH₃ | —H | —CH₃ | —CH₃ | —CH₃ | —CH₃ |
| 809 | —H | —H | —OC(O)H | —(CH₂)₂— | —CH₃ | —H | —CH₃ | —CH₂CH₃ | —CH₃ | —CH₃ |
| 810 | —H | —H | —OC(O)H | —(CH₂)₂— | —CH₃ | —H | —CH₂CH₃ | —CH₃ | —CH₃ | —CH₃ |
| 811 | —H | —H | —OC(O)H | —(CH₂)₂— | —CH₃ | —CH₃ | —H | —CH₃ | —CH₃ | —CH₃ |
| 812 | —H | —H | —OC(O)H | —(CH₂)₂— | —CH₃ | —CH₃ | —H | —CH₂CH₃ | —CH₃ | —CH₃ |
| 813 | —H | —H | —OC(O)H | —(CH₂)₂— | —CH₃ | —CH₃ | —CH₃ | —CH₃ | —CH₃ | —CH₃ |
| 814 | —H | —H | —OC(O)H | —(CH₂)₂— | —CH₂CH₃ | —H | —H | —H | —CH₃ | —CH₃ |
| 815 | —H | —CH₃ | —OC(O)H | —(CH₂)₂— | —CH₃ | —H | —H | —CH₃ | —CH₃ | —CH₃ |
| 816 | —H | —CH₃ | —OC(O)H | —(CH₂)₂— | —CH₃ | —H | —H | —CH₂CH₃ | —CH₃ | —CH₃ |
| 817 | —H | —CH₃ | —OC(O)H | —(CH₂)₂— | —CH₃ | —H | —CH₃ | —CH₃ | —CH₃ | —CH₃ |
| 818 | —H | —CH₃ | —OC(O)H | —(CH₂)₂— | —CH₃ | —H | —CH₃ | —CH₂CH₃ | —CH₃ | —CH₃ |
| 819 | —H | —CH₃ | —OC(O)H | —(CH₂)₂— | —CH₃ | —H | —CH₂CH₃ | —CH₃ | —CH₃ | —CH₃ |
| 820 | —H | —CH₃ | —OC(O)H | —(CH₂)₂— | —CH₃ | —CH₃ | —H | —CH₃ | —CH₃ | —CH₃ |
| 821 | —H | —CH₃ | —OC(O)H | —(CH₂)₂— | —CH₃ | —CH₃ | —H | —CH₂CH₃ | —CH₃ | —CH₃ |
| 822 | —H | —CH₃ | —OC(O)H | —(CH₂)₂— | —CH₃ | —CH₃ | —CH₃ | —CH₃ | —CH₃ | —CH₃ |
| 823 | —H | —CH₃ | —OC(O)H | —(CH₂)₂— | —CH₃ | —CH₃ | —CH₃ | —CH₂CH₃ | —CH₃ | —CH₃ |
| 824 | —H | —CH₃ | —OC(O)H | —(CH₂)₂— | —CH₃ | —CH₃ | —CH₂CH₃ | —CH₃ | —CH₃ | —CH₃ |
| 825 | —H | —CH₃ | —OC(O)H | —(CH₂)₂— | —CH₃ | —CH₂CH₃ | —H | —CH₃ | —CH₃ | —CH₃ |
| 826 | —H | —CH₃ | —OC(O)H | —(CH₂)₂— | —CH₃ | —CH₂CH₃ | —CH₃ | —CH₃ | —CH₃ | —CH₃ |
| 827 | —H | —CH₃ | —OC(O)H | —(CH₂)₂— | —CH₂CH₃ | —H | —H | —CH₃ | —CH₃ | —CH₃ |
| 828 | —H | —CH₃ | —OC(O)H | —(CH₂)₂— | —CH₂CH₃ | —H | —CH₃ | —CH₃ | —CH₃ | —CH₃ |
| 829 | —H | —CH₃ | —OC(O)H | —(CH₂)₂— | —CH₂CH₃ | —CH₃ | —H | —CH₃ | —CH₃ | —CH₃ |
| 830 | —H | —CH₃ | —OC(O)H | —(CH₂)₂— | —CH₂CH₃ | —CH₃ | —CH₃ | —CH₃ | —CH₃ | —CH₃ |
| 831 | —H | —CH₂CH₃ | —OC(O)H | —(CH₂)₂— | —CH₃ | —H | —H | —CH₃ | —CH₃ | —CH₃ |
| 832 | —H | —CH₂CH₃ | —OC(O)H | —(CH₂)₂— | —CH₃ | —H | —H | —CH₂CH₃ | —CH₃ | —CH₃ |
| 833 | —H | —CH₂CH₃ | —OC(O)H | —(CH₂)₂— | —CH₂CH₃ | —H | —H | —CH₃ | —CH₃ | —CH₃ |
| 834 | —OCH₃ | —CH₃ | —OC(O)H | —(CH₂)₂— | —CH₃ | —H | —H | —CH₃ | —CH₃ | —CH₃ |
| 835 | —OCH₃ | —CH₃ | —OC(O)H | —(CH₂)₂— | —CH₃ | —H | —H | —CH₂CH₃ | —CH₃ | —CH₃ |
| 836 | —OCH₃ | —CH₃ | —OC(O)H | —(CH₂)₂— | —CH₂CH₃ | —H | —H | —CH₃ | —CH₃ | —CH₃ |
| 837 | —OCH₃ | —CH₂CH₃ | —OC(O)H | —(CH₂)₂— | —CH₃ | —H | —H | —CH₃ | —CH₃ | —CH₃ |
| 838 | —OCH₃ | —CH₂CH₃ | —OC(O)H | —(CH₂)₂— | —CH₃ | —H | —H | —CH₂CH₃ | —CH₃ | —CH₃ |
| 839 | —OCH₃ | —CH₂CH₃ | —OC(O)H | —(CH₂)₂— | —CH₂CH₃ | —H | —H | —CH₃ | —CH₃ | —CH₃ |
| 840 | —OCH₃ | —OCH₃ | —OC(O)H | —(CH₂)₂— | —CH₃ | —H | —H | —CH₃ | —CH₃ | —CH₃ |
| 841 | —OCH₃ | —OCH₃ | —OC(O)H | —(CH₂)₂— | —CH₃ | —H | —H | —CH₂CH₃ | —CH₃ | —CH₃ |
| 842 | —OH | —CH₃ | —OC(O)H | —(CH₂)₂— | —CH₃ | —H | —H | —CH₃ | —CH₃ | —CH₃ |
| 843 | —OH | —CH₃ | —OC(O)H | —(CH₂)₂— | —CH₃ | —H | —H | —CH₂CH₃ | —CH₃ | —CH₃ |
| 844 | —OH | —CH₃ | —OC(O)H | —(CH₂)₂— | —CH₂CH₃ | —H | —H | —CH₃ | —CH₃ | —CH₃ |
| 845 | —OH | —CH₂CH₃ | —OC(O)H | —(CH₂)₂— | —CH₃ | —H | —H | —CH₃ | —CH₃ | —CH₃ |
| 846 | —OH | —CH₂CH₃ | —OC(O)H | —(CH₂)₂— | —CH₃ | —H | —H | —CH₂CH₃ | —CH₃ | —CH₃ |
| 847 | —OH | —CH₂CH₃ | —OC(O)H | —(CH₂)₂— | —CH₂CH₃ | —H | —H | —CH₃ | —CH₃ | —CH₃ |
| 848 | —H | —OC(O)H | —H | —(CH₂)₂— | —CH₃ | —H | —H | —CH₃ | —CH₃ | —CH₃ |
| 849 | —H | —OC(O)H | —H | —(CH₂)₂— | —CH₃ | —H | —H | —CH₂CH₃ | —CH₃ | —CH₃ |
| 850 | —H | —OC(O)H | —H | —(CH₂)₂— | —CH₂CH₃ | —H | —H | —CH₃ | —CH₃ | —CH₃ |
| 851 | —H | —OC(O)H | —CH₃ | —(CH₂)₂— | —CH₃ | —H | —H | —CH₃ | —CH₃ | —CH₃ |
| 852 | —H | —OC(O)H | —CH₃ | —(CH₂)₂— | —CH₃ | —H | —H | —CH₂CH₃ | —CH₃ | —CH₃ |
| 853 | —H | —OC(O)H | —CH₃ | —(CH₂)₂— | —CH₂CH₃ | —H | —H | —CH₃ | —CH₃ | —CH₃ |
| 854 | —H | —OC(O)H | —CH₂CH₃ | —(CH₂)₂— | —CH₃ | —H | —H | —CH₃ | —CH₃ | —CH₃ |
| 855 | —H | —OC(O)H | —CH₂CH₃ | —(CH₂)₂— | —CH₃ | —H | —H | —CH₂CH₃ | —CH₃ | —CH₃ |
| 856 | —H | —OC(O)H | —CH₂CH₃ | —(CH₂)₂— | —CH₂CH₃ | —H | —H | —CH₃ | —CH₃ | —CH₃ |
| 857 | —OCH₃ | —OC(O)H | —CH₃ | —(CH₂)₂— | —CH₃ | —H | —H | —CH₃ | —CH₃ | —CH₃ |
| 858 | —OCH₃ | —OC(O)H | —CH₃ | —(CH₂)₂— | —CH₃ | —H | —H | —CH₂CH₃ | —CH₃ | —CH₃ |
| 859 | —OCH₃ | —OC(O)H | —CH₃ | —(CH₂)₂— | —CH₂CH₃ | —H | —H | —CH₃ | —CH₃ | —CH₃ |
| 860 | —OCH₃ | —OC(O)H | —CH₂CH₃ | —(CH₂)₂— | —CH₃ | —H | —H | —CH₃ | —CH₃ | —CH₃ |
| 861 | —OCH₃ | —OC(O)H | —CH₂CH₃ | —(CH₂)₂— | —CH₃ | —H | —H | —CH₂CH₃ | —CH₃ | —CH₃ |
| 862 | —OCH₃ | —OC(O)H | —CH₂CH₃ | —(CH₂)₂— | —CH₂CH₃ | —H | —H | —CH₃ | —CH₃ | —CH₃ |
| 863 | —OCH₃ | —OC(O)H | —OCH₃ | —(CH₂)₂— | —CH₃ | —H | —H | —CH₃ | —CH₃ | —CH₃ |
| 864 | —OCH₃ | —OC(O)H | —OCH₃ | —(CH₂)₂— | —CH₃ | —H | —H | —CH₂CH₃ | —CH₃ | —CH₃ |
| 865 | —OCH₃ | —OC(O)H | —OCH₃ | —(CH₂)₂— | —CH₂CH₃ | —H | —H | —CH₃ | —CH₃ | —CH₃ |
| 866 | —OH | —OC(O)H | —CH₃ | —(CH₂)₂— | —CH₃ | —H | —H | —CH₃ | —CH₃ | —CH₃ |
| 867 | —OH | —OC(O)H | —CH₃ | —(CH₂)₂— | —CH₃ | —H | —H | —CH₂CH₃ | —CH₃ | —CH₃ |
| 868 | —OH | —OC(O)H | —CH₃ | —(CH₂)₂— | —CH₂CH₃ | —H | —H | —CH₃ | —CH₃ | —CH₃ |
| 869 | —OH | —OC(O)H | —CH₂CH₃ | —(CH₂)₂— | —CH₃ | —H | —H | —CH₃ | —CH₃ | —CH₃ |
| 870 | —OH | —OC(O)H | —CH₂CH₃ | —(CH₂)₂— | —CH₃ | —H | —H | —CH₂CH₃ | —CH₃ | —CH₃ |
| 871 | —OH | —OC(O)H | —CH₂CH₃ | —(CH₂)₂— | —CH₂CH₃ | —H | —H | —CH₃ | —CH₃ | —CH₃ |
| 872 | —H | —H | —OC(O)H | —H | —H | —(CH₂)₃— | —H | —CH₃ | —CH₃ | |
| 873 | —H | —H | —OC(O)H | —H | —H | —(CH₂)₃— | —H | —CH₂CH₃ | —CH₃ | |
| 874 | —H | —H | —OC(O)H | —H | —CH₃ | —(CH₂)₃— | —H | —H | —CH₃ | |
| 875 | —H | —H | —OC(O)H | —H | —CH₃ | —(CH₂)₃— | —H | —CH₃ | —CH₃ | |
| 876 | —H | —H | —OC(O)H | —H | —CH₃ | —(CH₂)₃— | —H | —CH₂CH₃ | —CH₃ | |
| 877 | —H | —H | —OC(O)H | —H | —CH₂CH₃ | —(CH₂)₃— | —H | —H | —CH₃ | |

-continued

| | | | | | | | | |
|---|---|---|---|---|---|---|---|---|
| 878 | —H | —H | —OC(O)H | —H | —CH$_2$CH$_3$ | —(CH$_2$)$_3$— | —H | —CH$_3$ | —CH$_3$ |
| 879 | —H | —CH$_3$ | —OC(O)H | —H | —H | —(CH$_2$)$_3$— | —H | —CH$_3$ | —CH$_3$ |
| 880 | —H | —CH$_3$ | —OC(O)H | —H | —H | —(CH$_2$)$_3$— | —H | —CH$_2$CH$_3$ | —CH$_3$ |
| 881 | —H | —CH$_3$ | —OC(O)H | —H | —CH$_3$ | —(CH$_2$)$_3$— | —H | —H | —CH$_3$ |
| 882 | —H | —CH$_3$ | —OC(O)H | —H | —CH$_3$ | —(CH$_2$)$_3$— | —H | —CH$_3$ | —CH$_3$ |
| 883 | —H | —CH$_3$ | —OC(O)H | —H | —CH$_3$ | —(CH$_2$)$_3$— | —H | —CH$_2$CH$_3$ | —CH$_3$ |
| 884 | —H | —CH$_3$ | —OC(O)H | —H | —CH$_2$CH$_3$ | —(CH$_2$)$_3$— | —H | —H | —CH$_3$ |
| 885 | —H | —CH$_3$ | —OC(O)H | —H | —CH$_2$CH$_3$ | —(CH$_2$)$_3$— | —H | —CH$_3$ | —CH$_3$ |
| 886 | —OCH$_3$ | —CH$_3$ | —OC(O)H | —H | —H | —(CH$_2$)$_3$— | —H | —CH$_3$ | —CH$_3$ |
| 887 | —OCH$_3$ | —CH$_3$ | —OC(O)H | —H | —H | —(CH$_2$)$_3$— | —H | —CH$_2$CH$_3$ | —CH$_3$ |
| 888 | —OCH$_3$ | —CH$_3$ | —OC(O)H | —H | —CH$_3$ | —(CH$_2$)$_3$— | —H | —H | —CH$_3$ |
| 889 | —OCH$_3$ | —CH$_3$ | —OC(O)H | —H | —CH$_3$ | —(CH$_2$)$_3$— | —H | —CH$_3$ | —CH$_3$ |
| 890 | —OCH$_3$ | —CH$_3$ | —OC(O)H | —H | —CH$_3$ | —(CH$_2$)$_3$— | —H | —CH$_2$CH$_3$ | —CH$_3$ |
| 891 | —OCH$_3$ | —CH$_3$ | —OC(O)H | —H | —CH$_2$CH$_3$ | —(CH$_2$)$_3$— | —H | —H | —CH$_3$ |
| 892 | —OCH$_3$ | —CH$_3$ | —OC(O)H | —H | —CH$_2$CH$_3$ | —(CH$_2$)$_3$— | —H | —CH$_3$ | —CH$_3$ |
| 893 | —OH | —CH$_3$ | —OC(O)H | —H | —H | —(CH$_2$)$_3$— | —H | —CH$_3$ | —CH$_3$ |
| 894 | —OH | —CH$_3$ | —OC(O)H | —H | —H | —(CH$_2$)$_3$— | —H | —CH$_2$CH$_3$ | —CH$_3$ |
| 895 | —OH | —CH$_3$ | —OC(O)H | —H | —CH$_3$ | —(CH$_2$)$_3$— | —H | —H | —CH$_3$ |
| 896 | —OH | —CH$_3$ | —OC(O)H | —H | —CH$_3$ | —(CH$_2$)$_3$— | —H | —CH$_3$ | —CH$_3$ |
| 897 | —OH | —CH$_3$ | —OC(O)H | —H | —CH$_3$ | —(CH$_2$)$_3$— | —H | —CH$_2$CH$_3$ | —CH$_3$ |
| 898 | —OH | —CH$_3$ | —OC(O)H | —H | —CH$_2$CH$_3$ | —(CH$_2$)$_3$— | —H | —H | —CH$_3$ |
| 899 | —OH | —CH$_3$ | —OC(O)H | —H | —CH$_2$CH$_3$ | —(CH$_2$)$_3$— | —H | —CH$_3$ | —CH$_3$ |
| 900 | —H | —CH$_2$CH$_3$ | —OC(O)H | —H | —H | —(CH$_2$)$_3$— | —H | —CH$_3$ | —CH$_3$ |
| 901 | —H | —CH$_2$CH$_3$ | —OC(O)H | —H | —H | —(CH$_2$)$_3$— | —H | —CH$_2$CH$_3$ | —CH$_3$ |
| 902 | —H | —CH$_2$CH$_3$ | —OC(O)H | —H | —CH$_3$ | —(CH$_2$)$_3$— | —H | —H | —CH$_3$ |
| 903 | —H | —CH$_2$CH$_3$ | —OC(O)H | —H | —CH$_3$ | —(CH$_2$)$_3$— | —H | —CH$_3$ | —CH$_3$ |
| 904 | —H | —CH$_2$CH$_3$ | —OC(O)H | —H | —CH$_3$ | —(CH$_2$)$_3$— | —H | —CH$_2$CH$_3$ | —CH$_3$ |
| 905 | —H | —CH$_2$CH$_3$ | —OC(O)H | —H | —CH$_2$CH$_3$ | —(CH$_2$)$_3$— | —H | —H | —CH$_3$ |
| 906 | —H | —CH$_2$CH$_3$ | —OC(O)H | —H | —CH$_2$CH$_3$ | —(CH$_2$)$_3$— | —H | —CH$_3$ | —CH$_3$ |
| 907 | —OCH$_3$ | —CH$_2$CH$_3$ | —OC(O)H | —H | —H | —(CH$_2$)$_3$— | —H | —CH$_3$ | —CH$_3$ |
| 908 | —OCH$_3$ | —CH$_2$CH$_3$ | —OC(O)H | —H | —H | —(CH$_2$)$_3$— | —H | —CH$_2$CH$_3$ | —CH$_3$ |
| 909 | —OCH$_3$ | —CH$_2$CH$_3$ | —OC(O)H | —H | —CH$_3$ | —(CH$_2$)$_3$— | —H | —H | —CH$_3$ |
| 910 | —OCH$_3$ | —CH$_2$CH$_3$ | —OC(O)H | —H | —CH$_3$ | —(CH$_2$)$_3$— | —H | —CH$_3$ | —CH$_3$ |
| 911 | —OCH$_3$ | —CH$_2$CH$_3$ | —OC(O)H | —H | —CH$_3$ | —(CH$_2$)$_3$— | —H | —CH$_2$CH$_3$ | —CH$_3$ |
| 912 | —OCH$_3$ | —CH$_2$CH$_3$ | —OC(O)H | —H | —CH$_2$CH$_3$ | —(CH$_2$)$_3$— | —H | —H | —CH$_3$ |
| 913 | —OH | —CH$_2$CH$_3$ | —OC(O)H | —H | —H | —(CH$_2$)$_3$— | —H | —CH$_3$ | —CH$_3$ |
| 914 | —OH | —CH$_2$CH$_3$ | —OC(O)H | —H | —H | —(CH$_2$)$_3$— | —H | —CH$_2$CH$_3$ | —CH$_3$ |
| 915 | —OH | —CH$_2$CH$_3$ | —OC(O)H | —H | —CH$_3$ | —(CH$_2$)$_3$— | —H | —H | —CH$_3$ |
| 916 | —OH | —CH$_2$CH$_3$ | —OC(O)H | —H | —CH$_3$ | —(CH$_2$)$_3$— | —H | —CH$_3$ | —CH$_3$ |
| 917 | —OH | —CH$_2$CH$_3$ | —OC(O)H | —H | —CH$_3$ | —(CH$_2$)$_3$— | —H | —CH$_2$CH$_3$ | —CH$_3$ |
| 918 | —OH | —CH$_2$CH$_3$ | —OC(O)H | —H | —CH$_2$CH$_3$ | —(CH$_2$)$_3$— | —H | —H | —CH$_3$ |
| 919 | —OH | —CH$_2$CH$_3$ | —OC(O)H | —H | —CH$_2$CH$_3$ | —(CH$_2$)$_3$— | —H | —CH$_3$ | —CH$_3$ |
| 920 | —OCH$_3$ | —OCH$_3$ | —OC(O)H | —H | —H | —(CH$_2$)$_3$— | —H | —CH$_3$ | —CH$_3$ |
| 921 | —OCH$_3$ | —OCH$_3$ | —OC(O)H | —H | —H | —(CH$_2$)$_3$— | —H | —CH$_2$CH$_3$ | —CH$_3$ |
| 922 | —OCH$_3$ | —OCH$_3$ | —OC(O)H | —H | —CH$_3$ | —(CH$_2$)$_3$— | —H | —H | —CH$_3$ |
| 923 | —OCH$_3$ | —OCH$_3$ | —OC(O)H | —H | —CH$_3$ | —(CH$_2$)$_3$— | —H | —CH$_3$ | —CH$_3$ |
| 924 | —OCH$_3$ | —OCH$_3$ | —OC(O)H | —H | —CH$_3$ | —(CH$_2$)$_3$— | —H | —CH$_2$CH$_3$ | —CH$_3$ |
| 925 | —OCH$_3$ | —OCH$_3$ | —OC(O)H | —H | —CH$_2$CH$_3$ | —(CH$_2$)$_3$— | —H | —H | —CH$_3$ |
| 926 | —OCH$_3$ | —OCH$_3$ | —OC(O)H | —H | —CH$_2$CH$_3$ | —(CH$_2$)$_3$— | —H | —CH$_3$ | —CH$_3$ |
| 927 | —H | —OC(O)H | —H | —H | —H | —(CH$_2$)$_3$— | —H | —CH$_3$ | —CH$_3$ |
| 928 | —H | —OC(O)H | —H | —H | —H | —(CH$_2$)$_3$— | —H | —CH$_2$CH$_3$ | —CH$_3$ |
| 929 | —H | —OC(O)H | —H | —H | —CH$_3$ | —(CH$_2$)$_3$— | —H | —H | —CH$_3$ |
| 930 | —H | —OC(O)H | —H | —H | —CH$_3$ | —(CH$_2$)$_3$— | —H | —CH$_3$ | —CH$_3$ |
| 931 | —H | —OC(O)H | —H | —H | —CH$_3$ | —(CH$_2$)$_3$— | —H | —CH$_2$CH$_3$ | —CH$_3$ |
| 932 | —H | —OC(O)H | —H | —H | —CH$_2$CH$_3$ | —(CH$_2$)$_3$— | —H | —H | —CH$_3$ |
| 933 | —H | —OC(O)H | —H | —H | —CH$_2$CH$_3$ | —(CH$_2$)$_3$— | —H | —CH$_3$ | —CH$_3$ |
| 934 | —H | —OC(O)H | —CH$_3$ | —H | —H | —(CH$_2$)$_3$— | —H | —CH$_3$ | —CH$_3$ |
| 935 | —H | —OC(O)H | —CH$_3$ | —H | —H | —(CH$_2$)$_3$— | —H | —CH$_2$CH$_3$ | —CH$_3$ |
| 936 | —H | —OC(O)H | —CH$_3$ | —H | —CH$_3$ | —(CH$_2$)$_3$— | —H | —H | —CH$_3$ |
| 937 | —H | —OC(O)H | —CH$_3$ | —H | —CH$_3$ | —(CH$_2$)$_3$— | —H | —CH$_3$ | —CH$_3$ |
| 938 | —H | —OC(O)H | —CH$_3$ | —H | —CH$_3$ | —(CH$_2$)$_3$— | —H | —CH$_2$CH$_3$ | —CH$_3$ |
| 939 | —H | —OC(O)H | —CH$_3$ | —H | —CH$_2$CH$_3$ | —(CH$_2$)$_3$— | —H | —H | —CH$_3$ |
| 940 | —H | —OC(O)H | —CH$_3$ | —H | —CH$_2$CH$_3$ | —(CH$_2$)$_3$— | —H | —CH$_3$ | —CH$_3$ |
| 941 | —OCH$_3$ | —OC(O)H | —CH$_3$ | —H | —H | —(CH$_2$)$_3$— | —H | —CH$_3$ | —CH$_3$ |
| 942 | —OCH$_3$ | —OC(O)H | —CH$_3$ | —H | —H | —(CH$_2$)$_3$— | —H | —CH$_2$CH$_3$ | —CH$_3$ |
| 943 | —OCH$_3$ | —OC(O)H | —CH$_3$ | —H | —CH$_3$ | —(CH$_2$)$_3$— | —H | —H | —CH$_3$ |
| 944 | —OCH$_3$ | —OC(O)H | —CH$_3$ | —H | —CH$_3$ | —(CH$_2$)$_3$— | —H | —CH$_3$ | —CH$_3$ |
| 945 | —OCH$_3$ | —OC(O)H | —CH$_3$ | —H | —CH$_3$ | —(CH$_2$)$_3$— | —H | —CH$_2$CH$_3$ | —CH$_3$ |
| 946 | —OCH$_3$ | —OC(O)H | —CH$_3$ | —H | —CH$_2$CH$_3$ | —(CH$_2$)$_3$— | —H | —H | —CH$_3$ |
| 947 | —OCH$_3$ | —OC(O)H | —CH$_3$ | —H | —CH$_2$CH$_3$ | —(CH$_2$)$_3$— | —H | —CH$_3$ | —CH$_3$ |
| 948 | —OH | —OC(O)H | —CH$_3$ | —H | —H | —(CH$_2$)$_3$— | —H | —CH$_3$ | —CH$_3$ |
| 949 | —OH | —OC(O)H | —CH$_3$ | —H | —H | —(CH$_2$)$_3$— | —H | —CH$_2$CH$_3$ | —CH$_3$ |
| 950 | —OH | —OC(O)H | —CH$_3$ | —H | —CH$_3$ | —(CH$_2$)$_3$— | —H | —H | —CH$_3$ |
| 951 | —OH | —OC(O)H | —CH$_3$ | —H | —CH$_3$ | —(CH$_2$)$_3$— | —H | —CH$_3$ | —CH$_3$ |
| 952 | —OH | —OC(O)H | —CH$_3$ | —H | —CH$_3$ | —(CH$_2$)$_3$— | —H | —CH$_2$CH$_3$ | —CH$_3$ |
| 953 | —OH | —OC(O)H | —CH$_3$ | —H | —CH$_2$CH$_3$ | —(CH$_2$)$_3$— | —H | —H | —CH$_3$ |
| 954 | —OH | —OC(O)H | —CH$_3$ | —H | —CH$_2$CH$_3$ | —(CH$_2$)$_3$— | —H | —CH$_3$ | —CH$_3$ |
| 955 | —H | —OC(O)H | —CH$_2$CH$_3$ | —H | —H | —(CH$_2$)$_3$— | —H | —CH$_3$ | —CH$_3$ |
| 956 | —H | —OC(O)H | —CH$_2$CH$_3$ | —H | —H | —(CH$_2$)$_3$— | —H | —CH$_2$CH$_3$ | —CH$_3$ |
| 957 | —H | —OC(O)H | —CH$_2$CH$_3$ | —H | —CH$_3$ | —(CH$_2$)$_3$— | —H | —H | —CH$_3$ |
| 958 | —H | —OC(O)H | —CH$_2$CH$_3$ | —H | —CH$_3$ | —(CH$_2$)$_3$— | —H | —CH$_3$ | —CH$_3$ |
| 959 | —H | —OC(O)H | —CH$_2$CH$_3$ | —H | —CH$_3$ | —(CH$_2$)$_3$— | —H | —CH$_2$CH$_3$ | —CH$_3$ |
| 960 | —H | —OC(O)H | —CH$_2$CH$_3$ | —H | —CH$_2$CH$_3$ | —(CH$_2$)$_3$— | —H | —H | —CH$_3$ |

| | | | | | -continued | | | | |
|---|---|---|---|---|---|---|---|---|---|
| 961 | —H | —OC(O)H | —CH₂CH₃ | —H | —CH₂CH₃ | —(CH₂)₃— | —H | —CH₃ | —CH₃ |
| 962 | —OCH₃ | —OC(O)H | —CH₂CH₃ | —H | —H | —(CH₂)₃— | —H | —CH₃ | —CH₃ |
| 963 | —OCH₃ | —OC(O)H | —CH₂CH₃ | —H | —H | —(CH₂)₃— | —H | —CH₂CH₃ | —CH₃ |
| 964 | —OCH₃ | —OC(O)H | —CH₂CH₃ | —H | —CH₃ | —(CH₂)₃— | —H | —H | —CH₃ |
| 965 | —OCH₃ | —OC(O)H | —CH₂CH₃ | —H | —CH₃ | —(CH₂)₃— | —H | —CH₃ | —CH₃ |
| 966 | —OCH₃ | —OC(O)H | —CH₂CH₃ | —H | —CH₃ | —(CH₂)₃— | —H | —CH₂CH₃ | —CH₃ |
| 967 | —OCH₃ | —OC(O)H | —CH₂CH₃ | —H | —CH₂CH₃ | —(CH₂)₃— | —H | —H | —CH₃ |
| 968 | —OCH₃ | —OC(O)H | —CH₂CH₃ | —H | —CH₂CH₃ | —(CH₂)₃— | —H | —CH₃ | —CH₃ |
| 969 | —OH | —OC(O)H | —CH₂CH₃ | —H | —H | —(CH₂)₃— | —H | —CH₃ | —CH₃ |
| 970 | —OH | —OC(O)H | —CH₂CH₃ | —H | —H | —(CH₂)₃— | —H | —CH₂CH₃ | —CH₃ |
| 971 | —OH | —OC(O)H | —CH₂CH₃ | —H | —CH₃ | —(CH₂)₃— | —H | —H | —CH₃ |
| 972 | —OH | —OC(O)H | —CH₂CH₃ | —H | —CH₃ | —(CH₂)₃— | —H | —CH₃ | —CH₃ |
| 973 | —OH | —OC(O)H | —CH₂CH₃ | —H | —CH₃ | —(CH₂)₃— | —H | —CH₂CH₃ | —CH₃ |
| 974 | —OH | —OC(O)H | —CH₂CH₃ | —H | —CH₂CH₃ | —(CH₂)₃— | —H | —H | —CH₃ |
| 975 | —OH | —OC(O)H | —CH₂CH₃ | —H | —CH₂CH₃ | —(CH₂)₃— | —H | —CH₃ | —CH₃ |
| 976 | —OCH₃ | —OC(O)H | —OCH₃ | —H | —H | —(CH₂)₃— | —H | —CH₃ | —CH₃ |
| 977 | —OCH₃ | —OC(O)H | —OCH₃ | —H | —H | —(CH₂)₃— | —H | —CH₂CH₃ | —CH₃ |
| 978 | —OCH₃ | —OC(O)H | —OCH₃ | —H | —CH₃ | —(CH₂)₃— | —H | —H | —CH₃ |
| 979 | —OCH₃ | —OC(O)H | —OCH₃ | —H | —CH₃ | —(CH₂)₃— | —H | —CH₃ | —CH₃ |
| 980 | —OCH₃ | —OC(O)H | —OCH₃ | —H | —CH₃ | —(CH₂)₃— | —H | —CH₂CH₃ | —CH₃ |
| 981 | —OCH₃ | —OC(O)H | —OCH₃ | —H | —CH₂CH₃ | —(CH₂)₃— | —H | —H | —CH₃ |
| 982 | —OCH₃ | —OC(O)H | —OCH₃ | —H | —CH₂CH₃ | —(CH₂)₃— | —H | —CH₃ | —CH₃ |

The novel formate ester tetralin compounds of the present invention, with their musk aroma properties, have high utility in the fragrance industry. These compounds can be employed alone, in combination with one another, and/or in combination with one or more ingredients to provide excellent musk fragrance compositions. The compounds of the invention are particularly useful in rounding off compositions, and blend particularly well with aldehydes of various fragrance types.

For example, the compounds of Formula [I] may be used as olfactory components in anionic, cationic, non-ionic and zwitterionic detergents, soaps, fabric softener compositions, fabric softener articles for use in clothes dryers, space odorants and deodorants, perfumes, colognes, toilet water, toiletries, bath preparations, deodorants, cosmetics, hand lotions, sunscreens, powders, as well as in other ways. The amount of the subject compounds to be used in modifying the olfactory or fragrance properties of a composition (that is, modifying, augmenting, enhancing, or improving the aroma of such compositions), will vary depending upon the particular use intended, as will be readily apparent to those skilled in the art. Although they may be present in major or minor amounts, preferably, because of the strength of their odor, the compounds of the invention are generally employed as a minor ingredient, that is, in an amount of about 0.1 percent by weight of the fragrance composition up to about 50 percent by weight of the fragrance composition, preferably about 0.1 percent by weight up to about 30 percent by weight of the fragrance composition, and most preferably about 0.1 percent by weight up to about 5.0 percent by weight of the fragrance composition. Within these basic parameters, the olfactorily effective amount (that is, the amount of the compounds of Formula [I] effective to modify, augment, enhance or improve the aroma properties of a composition) will be well within the ambit of one skilled in the art, once armed with the present disclosures.

The fragrance compositions of the invention may, if desired, contain a carrier or vehicle (as used herein, the term "carrier" shall be considered synonymous with the term "vehicle"). Such carriers include liquids such as a non-toxic alcohol, a non-toxic glycol, or the like. An example of a non-toxic alcohol is ethyl alcohol. An example of a non-toxic glycol is 1,2-propylene glycol. Alternatively, the carrier can be an absorbent solid such as a gum, e.g., gum arabic, xantham gum or guar gum, or components for encapsulating a composition such as gelatin, by means of coacervation or such as a urea formaldehyde polymer whereby a polymeric shell is formed around a liquid perfume oil center. The amount of the vehicle or carrier will vary depending upon the particular vehicle or carrier employed and use intended, as will be readily apparent to those skilled in the art. However, the vehicle or carrier can generally be employed in an amount of about 5 percent by weight up to about 95 percent by weight of the fragrance composition.

The fragrance composition may alternatively or additionally contain other perfumery materials. Typical additional perfumery materials which may form part of compositions of the invention include: natural essential oils such as lemon oil, mandarin oil, clove leaf oil, petitgrain oil, cedar wood oil, patchouli oil, lavandin oil, neroli oil, ylang oil, rose absolute or jasmine absolute; natural resins such as labdanum resin or olibanum resin; single perfumery chemicals which may be isolated from natural sources or manufactures synthetically, as for example, alcohols such as geraniol, nerol, citronellol, linalol, tetrahydrogeraniol, betaphenylethyl alcohol, methyl phenyl carbinol, dimethyl benzyl carbinol, menthol or cedrol; acetates and other esters derived from such alcohols; aldehydes such as citral, citronellal, hydroxycitronellal, lauric aldehyde, undecylenic aldehyde, cinnamaldehyde, amyl cinnamic aldehyde, vanillin or heliotropin; acetals derived from such aldehydes; ketones such as methyl hexyl ketone, the ionones and the methylionones; phenolic compounds such as eugenol and isoeugenol; other synthetic musks such as musk xylene, musk ketone, hexamethylisochroman, 5-acetylisopropyltetramethylindane, 6-acetyl-hexamethyltetralin (TETRALIDE ®, a registered trademark of Bush Boake Allen Limited), 5-acetyl-hexamethylindane, and ethylene brassylate; and other materials commonly employed in the art of perfumery. Typically at least five, and usually at least ten, of such materials will be present as components of the active ingredient. The amount of the additional perfumery material will vary depending upon the particular perfumery material employed and use intended, as will be apparent to those skilled in the art.

Fragrance compositions and preparatory techniques are well known in the art, and are disclosed, for example, in "Soap, Perfumery and Cosmetics", by W. A.

Poucher, 7th edition, published by Chapman & Hall (London) (1959); "Perfume and Flavour Chemicals", by S. Arctander, published by the author (Montclair) (1959); and "Perfume and Flavour Materials of Natural Origin", also by S. Arctander, self-published (Elizabeth, N.J.) (1960), the disclosures of each of which are incorporated herein by reference, in their entirety.

This invention is further described in the following Examples 1-24, which illustrate methods of preparation for compounds of the invention. Examples 1-2 are actual examples, Examples 3-24 are prophetic examples. A summary of these examples is set forth below. These examples are intended to be illustrative only, and are not to be construed as limiting the scope of the appended claims.

Example 1 describes the preparation and fragrance testing of 1,1,4,4,7-pentamethyl-5-methoxy-1,2,3,4-tetrahydronaphthalene-6-ol formate ester, a compound of Formula I wherein $R^1$ is $-OCH_3$, $R^2$ is $-OC(O)H$, $R^3$ is $-CH_3$, $R^4$ is $-H$, $R^5$ is $-CH_3$, $R^6$ is $-CH_3$, $R^7$ is $-H$, $R^8$ is $-H$, $R^9$ is $-CH_3$ and $R^{10}$ is $-CH_3$.

Example 2 describes the preparation and fragrance testing of 1,1,3,4,4,6-hexamethyl-1,2,3,4-tetrahydronaphthalene-7-ol formate ester, a compound of Formula I wherein $R^1$ is $-H$, $R^2$ is $-OC(O)H$, $R^3$ is $-CH_3$, $R^4$ is $-H$, $R^5$ is $-CH_3$, $R^6$ is $-CH_3$, $R^7$ is $-CH_3$, $R^8$ is $-H$, $R^9$ is $-CH_3$ and $R^{10}$ is $-CH_3$.

Example 3 describes the preparation of 1,1,2,4,4,6-hexamethyl-1,2,3,4-tetrahydronaphthalene-7-ol formate ester, a compound of Formula I wherein $R^1$ is $-H$, $R^2$ is $-OC(O)H$, $R^3$ is $-CH_3$, $R^4$ is $-H$, $R^5$ is $-CH_3$, $R^6$ is $-CH_3$, $R^7$ is $-H$, $R^8$ is $-CH_3$, $R^9$ is $-CH_3$ and $R^{10}$ is $-CH_3$.

Example 4 describes the preparation of 1,1,4,4,5,7-hexamethyl-1,2,3,4-tetrahydronaphthalene-6-ol formate ester, a compound of Formula I wherein $R^1$ is $-CH_3$, $R^2$ is $-OC(O)H$, $R^3$ is $-CH_3$, $R^4$ is $-H$, $R^5$ is $-CH_3$, $R^6$ is $-CH_3$, $R^7$ is $-H$, $R^8$ is $-H$, $R^9$ is $-CH_3$ and $R^{10}$ is $-CH_3$.

Example 5 describes the preparation of 1,1,4,4-tetramethyl-6-ethyl-1,2,3,4-tetrahydronaphthalene-7-ol formate ester, a compound of Formula I wherein $R^1$ is $-H$, $R^2$ is $-OC(O)H$, $R^3$ is $-CH_2CH_3$, $R^4$ is $-H$, $R^5$ is $-CH_3$, $R^6$ is $-CH_3$, $R^7$ is $-H$, $R^8$ is $-H$, $R^9$ is $-CH_3$ and $R^{10}$ is $-CH_3$.

Example 6 describes the preparation of 1,1,2,4,4,5,7-heptamethyl-1,2,3,4-tetrahydronaphthalene-6-ol formate ester, a compound of Formula I wherein $R^1$ is $-CH_3$, $R^2$ is $-OC(O)H$, $R^3$ is $-CH_3$, $R^4$ is $-H$, $R^5$ is $-CH_3$, $R^6$ is $-CH_3$, $R^7$ is $-CH_3$, $R^8$ is $-H$, $R^9$ is $-CH_3$ and $R^{10}$ is $-CH_3$, and 1,1,2,4,4,5,6-heptamethyl-1,2,3,4-tetrahydronaphthalene-7-ol formate ester, a compound of Formula I wherein $R^1$ is $-H$, $R^2$ is $-OC(O)H$, $R^3$ is $-CH_3$, $R^4$ is $-CH_3$, $R^5$ is $-CH_3$, $R^6$ is $-CH_3$, $R^7$ is $-H$, $R^8$ is $-CH_3$, $R^9$ is $-CH_3$ and $R^{10}$ is $-CH_3$.

Example 7 describes the preparation of 1,1,2,3,4,4,7-heptamethyl-1,2,3,4-tetrahydronaphthalene-6-ol formate ester, a compound of Formula I wherein $R^1$ is $-H$, $R^2$ is $-OC(O)H$, $R^3$ is $CH_3$, $R^4$ is $-H$, $R^5$ is $-CH_3$, $R^6$ is $-CH_3$, $R^7$ is $-CH_3$, $R^8$ is $-CH_3$, $R^9$ is $-CH_3$ and $R^{10}$ is $-CH_3$.

Example 8 describes the preparation of 1,1,2,4,4,6,8-heptamethyl-1,2,3,4-tetrahydronaphthalene-7-ol formate ester, a compound of Formula I wherein $R^1$ is $-CH_3$, $R^2$ is $-OC(O)H$, $R^3$ is $-CH_3$, $R^4$ is $-H$, $R^5$ is $-CH_3$, $R^6$ is $-CH_3$, $R^7$ is $-H$, $R^8$ is $-CH_3$, $R^9$ is $-CH_3$ and $R^{10}$ is $-CH_3$.

Example 9 describes the preparation of 4-ethyl-1,1,2,4,5,7-hexamethyl-1,2,3,4-tetrahydronaphthalene-6-ol formate ester, a compound of Formula I wherein $R^1$ is $-CH_3$, $R^2$ is $-OC(O)H$, $R^3$ is $-CH_3$, $R^4$ is $-H$, $R^5$ is $-CH_3$, $R^6$ is $-CH_3$, $R^7$ is $-CH_3$, $R^8$ is $-H$, $R^9$ is $-CH_2CH_3$ and $R^{10}$ is $-CH_3$.

Example 10 describes the preparation of 5-ethyl-1,1,2,4,4,7-hexamethyl-1,2,3,4 tetrahydronaphthalene-6-ol formate ester, a compound of Formula I wherein $R^1$ is $-CH_2CH_3$, $R^2$ is $-OC(O)H$, $R^3$ is $-CH_3$, $R^4$ is $-H$, $R^5$ is $-CH_3$, $R^6$ is $-CH_3$, $R^7$ is $-CH_3$, $R^8$ is $-H$, $R^9$ is $-CH_3$ and $R^{10}$ is $-CH_3$.

Example 11 describes the preparation of 7-ethyl-1,1,2,4,4,5-hexamethyl-1,2,3,4-tetrahydronaphthalene-6-ol formate ester, a compound of Formula I wherein $R^1$ is $-CH_3$, $R^2$ is $-OC(O)H$, $R^3$ is $-CH_2CH_3$, $R^4$ is $-H$, $R^5$ is $-CH_3$, $R^6$ is $-CH_3$, $R^7$ is $-CH_3$, $R^8$ is $-H$, $R^9$ is $-CH_3$ and $R^{10}$ is $-CH_3$.

Examples 12, 13 and 14 describe the preparation of 1,1,4,4,7-pentamethyl-5-methoxy-1,2,3,4-tetrahydronaphthalene-6-ol formate ester, a compound of Formula I wherein $R^1$ is $-OCH_3$, $R^2$ is $-OC(O)H$, $R^3$ is $-CH_3$, $R^4$ is $-H$, $R^5$ is $-CH_3$, $R^6$ is $-CH_3$, $R^7$ is $-H$, $R^8$ is $-H$, $R^9$ is $-CH_3$ and $R^{10}$ is $-CH_3$.

Example 15 describes the preparation of 1,1,4,4,7-pentamethyl-5-hydroxy-1,2,3,4-tetrahydronaphthalene-6-ol formate ester, a compound of Formula I wherein $R^1$ is $-OH$, $R^2$ is $-OC(O)H$, $R^3$ is $-CH_3$, $R^4$ is $-H$, $R^5$ is $-CH_3$, $R^6$ is $-CH_3$, $R^7$ is $-H$, $R^8$ is $-H$, $R^9$ is $-CH_3$ and $R^{10}$ is $-CH_3$.

Example 16 describes the preparation of 7-ethyl-1,1,4,4-tetramethyl-5-hydroxy-1,2,3,4-tetrahydronaphthalene-6-ol formate ester, a compound of Formula I wherein $R^1$ is $-OH$, $R^2$ is $-OC(O)H$, $R^3$ is $-CH_2CH_3$, $R^4$ is $-H$, $R^5$ is $-CH_3$, $R^6$ is $-CH_3$, $R^7$ is $-H$, $R^8$ is $-H$, $R^9$ is $-CH_3$ and $R^{10}$ is $-CH_3$.

Example 17 describes the preparation of 7-ethyl-1,1,4,4-tetramethyl-5-methoxy-1,2,3,4-tetrahydronaphthalene-6-ol formate ester, a compound of Formula I wherein $R^1$ is $-OCH_3$, $R^2$ is $OC(O)H$, $R^3$ is $-CH_2CH_3$, $R^4$ is $-H$, $R^5$ is $-CH_3$, $R^6$ is $-CH_3$, $R^7$ is $-H$, $R^8$ is $-H$, $R^9$ is $-CH_3$ and $R^{10}$ $-CH_3$.

Example 18 describes the preparation of 1,1,2,4,4,7-hexamethyl-5-methoxy-1,2,3,4-tetrahydronaphthalene-6-ol formate ester, a compound of Formula I wherein $R^1$ is $-OCH_3$, $R^2$ is $-OC(O)H$, $R^3$ is $-CH_3$, $R^4$ is $-H$, $R^5$ is $-CH_3$, $R^6$ is $-CH_3$, $R^7$ is $-CH_3$, $R^8$ is $-H$, $R^9$ is $-CH_3$ and $R^{10}$ is $-CH_3$.

Example 19 describes the preparation of 1,1,2,4,4,5-hexamethyl-7-methoxy-1,2,3,4-tetrahydronaphthalene-6-ol formate ester, a compound of Formula I wherein $R^1$ is $-CH_3$, $R^2$ is $-OC(O)H$, $R^3$ is $-OCH_3$, $R^4$ is $-H$, $R^5$ is $-CH_3$, $R^6$ is $-CH_3$, $R^7$ is $-CH_3$, $R^8$ is $-H$, $R^9$ is $-CH_3$ and $R^{10}$ is $-CH_3$.

Example 20 describes the preparation of 1,1,2,4,4-pentamethyl-5,7-dimethoxy-1,2,3,4-tetrahydronaphthalene-6-ol formate ester, a compound of Formula I wherein $R^1$ is $-OCH_3$, $R^2$ is $-OC(O)H$, $R^3$ is $-OCH_3$, $R^4$ is $-H$, $R^5$ is $-CH_3$, $R^6$ is $-CH_3$, $R^7$ is $-CH_3$, $R^8$ is $-H$, $R^9$ is $-CH_3$ and $R^{10}$ $-CH_3$.

Example 21 describes the preparation of 1,2,6,7,8,8a-hexahydro-3,6,6,8a-tetramethylacenaphthylene-4-ol formate ester, a compound of Formula I wherein $R^1$ is $-H$, $R^2$ is $-OC(O)H$, $R^3$ is $-CH_3$, $R^4$ and $R^5$, taken together, are $-(CH_2)_2-$, $R^6$ is $-CH_3$, $R^7$ is $-H$, $R^8$ is $-H$, $R^9$ is $-CH_3$ and $R^{10}$ is $-CH_3$.

Example 22 describes the preparation of a mixture of 2,3,3a,4,5,9b-hexahydro-5,5,8,9b-tetramethyl-1H- benz[e]indene-7-ol formate ester, a compound of Formula I wherein $R^1$ is —H, $R^2$ is —OC(O)H, $R^3$ is —CH$_3$, $R^4$ is —H, $R^5$ is —CH$_3$, $R^6$ and $R^7$, taken together, are —(CH$_2$)$_3$—, $R^8$ is —H, $R^9$ is —CH$_3$ and $R^{10}$ is —CH$_3$, and 2,3,3a,4,5,9b-hexahydro-5,5,7,9b-tetramethyl-1H-benz[e]indene-8-ol formate ester, a compound of Formula I wherein $R^1$ is —H, $R^2$ is —CH$_3$, $R^3$ is —OC(O)H, $R^4$ is —H, $R^5$ is —CH$_3$, $R^6$ and $R^7$, taken together, are —(CH$_2$)$_3$—, $R^8$ is —H, $R^9$ is —CH$_3$ and $R^{10}$ is —CH$_3$.

Example 23 describes the preparation of 1,1,2,4,4-pentamethyl-5-methoxy-1,2,3,4-tetrahydronaphthalene-7-ol formate ester, a compound of Formula I wherein $R^1$ is —OCH$_3$, $R^2$ is —H, $R^3$ is —OC(O)H, $R^4$ is —H, $R^5$ is —CH$_3$, $R^6$ is CH$_3$, $R^7$ is —CH$_3$, $R^8$ is —H, $R^9$ is —CH$_3$ and $R^{10}$ is —CH$_3$.

Example 24 describes the preparation of 1,1,2,4,4-pentamethyl-1,2,3,4-tetrahydronaphthalene-7-ol formate ester, a compound of Formula I wherein $R^1$ is —H, $R^2$ is —H, $R^3$ is —OC(O)H, $R^4$ is —H, $R^5$ is —CH$_3$, $R^6$ is —CH$_3$, $R^7$ is —CH$_3$, $R^8$ is —H, $R^9$ is —CH$_3$ and $R^{10}$ is —CH$_3$.

EXAMPLE 1

Preparation of 1,1,4,4,7-Pentamethyl-5-Methoxy-1,2,3,4-Tetrahydronaphthalene-6-ol Formate Ester The starting material 1,1,4,4,7-pentamethyl-5-methoxy-1,2,3,4-tetrahydronaphthalene was prepared as follows. First, a 500 flask was charged with 230 ml dichloromethane, 19 g TiCl$_4$, and 18.3 g 2,5-dichloro-2,5-dimethylhexane, at 22° C. Next, 3-methyl anisole (12.2 g in 20 ml dichloromethane) was added dropwise over a period of an hour. After the addition was completed, the solution was heated to 35° C. and the temperature maintained for an additional 2.5 hours. The solution was then cooled to 5° C. and quenched with water. After transfer to a separatory funnel, the solution was washed with water, then twice with brine, dried over anhydrous sodium sulfate, and rotary evaporated to give a crude product (23.78 g) containing 79.4% (by area % GC) of 1,1,4,4,7-pentamethyl-5-methoxy-1,2,3,4-tetrahydronaphthalene.

To convert 1,1,4,4,7-pentamethyl-5-methoxy-1,2,3,4-tetrahydronaphthalene to its corresponding 6-carboxaldehyde, a 250 ml flask was charged with 130 ml dichloromethane and 24.51 g TiCl$_4$. The solution was cooled to 2° C. and 15 g of 1,1,4,4,7-pentamethyl-5-methoxy-1,2,3,4-tetrahydronaphthalene (with no further purification) and 20 ml dichloromethane were added, with stirring. Next, α,α-dichloromethyl methyl ether (13.37 g) was added over a period of 1.2 hours. After completion of addition, the solution was allowed to warm to room temperature. After a further half hour, the solution was quenched with water at a temperature of ≦8° C. The solution was distilled to remove residual starting material to yield a crude product (16.94 g) containing 77.4% (area % GC) of the 6-carboxaldehyde, 6-formyl-1,1,4,4,7-pentamethyl-5-methoxy-1,2,3,4-tetrahydro-naphthalene.

To convert the 6-carboxaldehyde to its corresponding formate ester, the following procedure was carried out. Into a 50 ml three-necked round-bottomed flask equipped with an additional funnel, a condenser and a thermocouple was placed 6.3 g of meta-chloroperbenzoic acid (50–60% purity from Aldrich Chemical Company, Inc., Milwaukee, Wis.) and 25 ml of dichloromethane. The mixture was stirred for 10 minutes at room temperature. The temperature was adjusted by use of an ice bath to 13° C. A solution of 4.0 grams of 6-formyl-1,1,4,4,7-pentamethyl-5-methoxy-1,2,3,4-tetrahydronaphthalene, purified to 99% purity by vacuum distillation, in 10 ml of dichloromethane was added dropwise over a period of 45 minutes. The temperature rose to 27° C. during the addition. The reaction was stirred an additional two hours. The reaction was then transferred to a separatory funnel, washed once with aqueous sodium bicarbonate, aqueous sodium metabisulfite, and again with sodium bicarbonate, followed by washing with brine. The organic layer was then dried over anhydrous sodium sulfate, filtered, and concentrated to give 4.4 g of the crude formate ester, 1,1,4,4,7-pentamethyl-5-methoxy-1,2,3,4-tetrahydronaphthalene-6-ol formate ester (98% area GC purity). Functionalization was confirmed by GC/MS.

The formate ester was then tested for its fragrance characteristics by GC/aromagram. Specifically, the 1,1,4,4,7-pentamethyl-5-methoxy-1,2,3,4-tetrahydronaphthalene-6-ol formate ester was injected into a Varian Model 3700 GC having a megabore GC column. The GC was equipped with a splitter which allowed one portion of the separated component stream to flow to the GC detector while the other portion was allowed to flow to a sniff port where a trained analyst assessed the fragrance characteristics of the formate ester compound. The compound was found to have a musky aroma, with sweet, tobacco, hay and green nuances.

EXAMPLE 2

Preparation of 1,1,3,4,4,6-Hexamethyl-1,2,3,4-Tetrahydronaphthalene-7-ol Formate Ester The starting material 1,1,3,4,4,6-hexamethyl-1,2,3,4-tetrahydronaphthalene (HMT) was prepared by substantially following the procedures of Frank, U.S. Pat. No. 4,877,913. Specifically, a 100 ml, four-necked, round bottom flask was charged with cyclohexane (7.17 g) and anhydrous aluminum chloride (1.004 g), and cooled to about 16° C. A 60 ml addition funnel was charged with para-cymene (39.87 g), diisobutylene-2 (8.34 g), and neohexene (6.25 g) and connected to the flask. The funnel mixture was added to the flask over a period of about one hour and the flask mixture stirred 30 minutes following addition, while maintaining the temperature at about 16° C. The reaction was then quenched with deionized water (15 ml), and the organic phase separated and washed with, in order, 5% HCl, 10% Na$_2$CO$_3$, and 50% brine. The aqueous layers were then dried over K$_2$CO$_3$, filtered, and evaporated to yield a crude product (41.13 g) containing 28.16 weight % HMT.

To convert HMT to its corresponding 7-carboxaldehyde, 186 ml dichloromethane and 19.8 ml TiCl$_4$ were charged in a 500 ml 3-necked round-bottomed flask equipped with addition tunnel, thermocouple and mechanical stirrer, and purged with nitrogen. The solution was cooled to 0° C. HMT (26 g; 98% purity) dissolved in 40 ml dichloromethane was then added during ten minutes with stirring at 0° C. After 5 min of additional stirring, α,α-dichoromethyl methyl ether (14 ml) was added dropwise over a period of one hour at 0° C. The solution was stirred for two hours additionally, and then quenched with water (80 ml). The solution was transferred to a separatory funnel, the organics washed twice with water (200 ml each time), then with brine (200 ml), dried over anhydrous sodium sulfate, filtered, and rotary evaporated to yield a crude product (33 g) containing the 7-carboxaldehyde, 7-formyl-1,1,3,4,4,6-hexamethyl-1,2,3,4-tetrahydronaphthalene (85% by area % GC). This material was distilled to remove residual starting material (9%) and used in the next step.

To convert the 7-carboxaldehyde to its corresponding formate ester, a 250 ml 3-necked round bottomed flask equipped with a thermocouple, mechanical stirrer, and Claisen adapter (which was connected to an addition funnel and condenser), was charged with 16.57 g of meta-chloroperbenzoic acid (60% purity from Aldrich Chemical Company, Inc., Milwaukee, Wis,) and 70 ml of dichloromethane. The mixture was stirred for 10 minutes at 22° C., and then cooled to 11° C. To this reaction mixture was added dropwise a solution of 9.8 g of 7-formyl-1,1,3,4,4,6-hexamethyl-1,2,3,4-tetrahydronaphthalene (without further purification) in 30 ml of dichloromethane. During the addition, which took 1.5 hours, the temperature was raised to 22° C., and maintained for two hours after the addition was completed. The reaction was quenched with water, and transferred to a separatory funnel. The organics were washed with a saturated solution of sodium metabisulfite until the peroxide test was negative, then washed successively with sodium bicarbonate and brine dried over anhydrous sodium sulfate, filtered, and rotary evaporated to give a crude product (10.8 g) containing 82% (area % GC) of the 1,1,3,4,4,6-hexamethyl-1,2,3,4-tetrahydronaphthalene-7-ol formate ester.

The formate ester was then tested for its fragrance characteristics by GC/aromagram. Specifically, the 1,1,3,4,4,6-hexamethyl-1,2,3,4-tetrahydronaphthalene-7-ol formate ester was injected into a Varian Model 3700 GC having a megabore GC column. The GC was equipped with a splitter which allowed one portion of the separated component stream to flow to the GC detector while the other portion was allowed to flow to a sniff port where a trained analyst assessed the fragrance characteristics of the formate ester compound. The compound was found to have a musky aroma, with animal and sweet nuances.

EXAMPLE 3

Preparation of
1,1,2,4,4,6-Hexamethyl-1,2,3,4-Tetrahydronaphthalene-7-ol Formate Ester The starting material 1,1,2,4,4,6-hexamethyl-1,2,3,4-tetrahydronaphthalene is prepared as follows. A 100 ml four-necked round bottom flask is charged with 1,1,3,4,4,6-hexamethyl-1,2,3,4-tetrahydronaphthalene (HMT) (20 g) and dichloromethane (32.6 g) and cooled to 0° C. with a dry ice/isopropanol bath. To the flask is then added, with stirring, anhydrous AlCl$_3$ (2.507 g). The temperature of the flask is maintained between about 0° C. and 10° C. while the reaction is allowed to proceed for about 2.5 hrs. The reaction is then quenched with ice water (25 ml), and the resultant product washed with deionized water. The aqueous layer is extracted twice with ether, the organics are combined, dried over K$_2$CO$_3$ and rotoevaporated to yield a crude product (18.26 g) containing 37.22 weight percent of a mixture of 1,1,2,4,4,6-hexamethyl-1,2,3,4-tetrahydronaphthalene, HMT, 1,1,3,5-tetramethyl-3-isopropylindane and 1,3,3,5-tetramethyl-1-isopropylindane. The indanes are removed from the mixture by preparative gas chromatography. The desired compound, 1,1,2,4,4,6-hexamethyl-1,2,3,4-tetrahydronaphthalene, is then separated from HMT using a vacuum spinning band fractional distillation apparatus.

To convert 1,1,2,4,4,6-hexamethyl-1,2,3,4-tetrahydronaphthalene to its corresponding 7-carboxaldehyde, 40 ml methylene chloride and 19.0 g TiCl$_4$ are charged in a 100 ml 3-necked round-bottomed flask equipped with addition funnel, thermocouple, mechanical stirrer, purged with nitrogen. The solution is cooled to 0° C. Next, 1,1,2,4,4,6-hexamethyl-1,2,3,4-tetrahydronaphthalene (13.0 g) is dissolved in 40 ml methylene chloride and added during ten minutes with stirring at 0° C. After 5 min of additional stirring, α,α-dichoromethyl methyl ether (6 g) is added dropwise over a period of one hour at 0° C. The solution is stirred for two hours additionally, and then quenched with crushed ice (50 g). The solution is transferred to a separatory funnel, the organics washed twice with methylene chloride (10 ml each time), then twice with water (10 ml each time), dried over anhydrous sodium sulfate, filtered, and rotary evaporated to yield a crude product containing the 7-carboxaldehyde, 7-formyl-1,1,2,4,4,6-hexamethyl-1,2,3,4-tetrahydronaphthalene. This material is then distilled to remove residual starting material and used in the next step.

To convert the 7-carboxaldehyde to its corresponding formate ester, a 250 ml 3-necked round bottomed flask equipped with a thermocouple, mechanical stirrer, and Claisen adapter (which is connected to an addition funnel and condenser), is charged with 16.57 g of meta-chloroperbenzoic acid (60% purity from Aldrich Chemical Company, Inc., Milwaukee, Wis.) and 70 ml of dichloromethane. The mixture is stirred for 10 minutes at 22° C., and then cooled to 11° C. To this reaction mixture is added dropwise a solution of 9.8 g of 7-formyl-1,1,2,4,4,6-hexamethyl-1,2,3,4-tetrahydronaphthalene in 30 ml of dichloromethane. During the addition which takes about 1.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing the 1,1,2,4,4,6-hexamethyl-1,2,3,4-tetrahydronaphthalene-7-ol formate ester.

EXAMPLE 4

Preparation of
1,1,4,4,5,7-Hexamethyl-1,2,3,4-Tetrahydronaphthalene-6-ol Formate Ester The starting material 1,1,4,4,5,7-hexamethyl-1,2,3,4-tetrahydronaphthalene is prepared by substantially following the procedures of Fehr et al., U.S. Pat. No. 5,162,588. Specifically, in a 1 liter three-neck flask, equipped with a mechanical stirrer and kept under nitrogen, 150.0 g of methallyl chloride are slowly (2 hrs) added to a mixture of meta-xylene (490.9 g) and H$_2$SO$_4$ (30.0 g), while the temperature is maintained at 20° C. After 3 hrs, the H$_2$SO$_4$ is decanted and the organic phase is washed with, in succession, water, an aqueous solution saturated with NaHCO$_3$, and an aqueous solution saturated with NaCl. The excess of meta-xylene is recovered through distillation, and the residue is distilled. A mixture of two isomers, 1-(2-chloro-1,1-dimethylethyl)-2,4-dimethylbenzene and 1-(2-chloro-1,1-dimethylethyl)-3,5-dimethylbenzene, is obtained.

In a 0.5 liter flask equipped with a mechanical stirrer and kept under nitrogen, a suspension of Mg (13.67 g) in tetrahydrofuran (THF) (33 ml) is heated to reflux. Next, 4 ml of a solution of the mixture of 1-(2-chloro-1,1-dimethylethyl)-2,4,-dimethylbenzene and 1(2-chloro-1,1-dimethyl-ethyl)-3,5-dimethylbenzene (100 g) in THF (33 ml) is then added. Once the reaction has started, more THF is added (100 ml) and the remaining mixture of 1-(2-chloro-1,1-dimethylethyl)-2,4-dimethylbenzene and 1-(2-chloro-1,1-dimethyl-ethyl)-3,5-dimethylbenzene in THF is then added over 75 minutes. The reaction mixture is stirred for 30 min at a temperature of 75° C. Methallylchloride (64.3 g) is then added over 20 min while maintaining the reaction mixture at reflux. After 30 min, the mixture is cooled to 10° C., and hydrolyzed with water (133 ml). The phases are separated and the aqueous layer is extracted with ether. The combined organic layers are washed with an aqueous solution saturated NaCl, and the solvents are evaporated. Distillation provides a colorless oily mixture (97.0 g) which is used in the following cyclization reaction.

In a 200 ml three-neck flask equipped with mechanical stirring and kept under nitrogen, 97.0 g of the above-mentioned oily mixture are added to a mixture of petroleum ether 30° C.-50° C. (33 ml) and $H_2SO_4$ (2.34 g), over 1 hr and at a temperature of 5° C.-10° C. After 30 min at 10° C., the $H_2SO_4$ is separated from the organic layer and the latter is washed successively with $H_2O$, saturated $NaHCO_3$ solution, and saturated NaCl solution. Recrystallization of the raw product in ethanol yields 1,1,4,4,5,7-hexamethyl-1,2,3,4-tetrahydronaphthalene (80.6 g, 93% yield).

To convert 1,1,4,4,5,7-hexamethyl-1,2,3,4-tetrahydronaphthalene to its corresponding 6-carboxaldehyde, 12.96 g is placed in a 100 ml three-necked round bottom flask equipped with a reflux condenser, a stirrer and a dropping funnel. In accordance with the general procedures described in *Organic Syntheses*, Collective Vol. 5 pp. 49-50, by A. Rieche, H. Gross, and E. Hoft, edited by H. E. Baumgarten, John Wiley and Sons (New York, N.Y. 1973), methylene chloride (37.5 ml) is added to the flask. The solution is then cooled in an ice bath, and $TiCl_4$ (19.0 g) is added over a period of 3 minutes. While the solution is stirred and cooled, α,α-dichloromethyl methyl ether (5.75 g) is added dropwise over a 25 minute period. After the addition is complete, the mixture is stirred for 5 minutes in the ice bath, for 30 minutes without cooling, and for 15 minutes at 35° C. The reaction mixture is then poured into a separatory funnel containing 50 g of crushed ice and is shaken thoroughly. The organic layer is separated, and the aqueous solution is extracted with two 10 ml portions of methylene chloride. The combined organic solution is washed three times with 10 ml portions of water. A crystal of hydroquinone is added to the methylene chloride solution, which is then dried over anhydrous sodium sulfate. After evaporation of the solvent, the residue is distilled to give yield as a crude product, 6-formyl-1,1,4,4,5,7-hexamethyl-1,2,3,4-tetrahydronaphthalene. The 6-formyl-1,1,4,4,5,7-hexamethyl-1,2,3,4-tetrahydronaphthalene is then further purified using standard fractional distillation techniques.

To convert the 6-carboxaldehyde to its corresponding formate ester, a 250 ml 3-necked round bottomed flask equipped with a thermocouple, mechanical stirrer, and Claisen adapter (which is connected to an addition funnel and condenser), is charged with 16.57 g of meta-chloroperbenzoic acid (60% purity from Aldrich Chemical Company, Inc., Milwaukee, Wis.) and 70 ml of dichloromethane. The mixture is stirred for 10 minutes at 22° C., and then cooled to 11° C. To this reaction mixture is added dropwise a solution of 9.8 g of the 6-formyl-1,1,4,4,5,7-hexamethyl-1,2,3,4-tetrahydronaphthalene in 30 ml of dichloromethane. During the addition, which takes about 1.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing the 1,1,4,4,5,7-hexamethyl-1,2,3,4-tetrahydronaphthalene-6-ol formate ester.

EXAMPLE 5

Preparation of
1,1,4,4-Tetramethyl-6-Ethyl-1,2,3,4-Tetrahydronaphthalene-7-ol Formate Ester The starting material 1,1,4,4-tetramethyl-6-ethyl-1,2,3,4-tetrahydronaphthalene is prepared by substantially following the procedures of Carpenter, U.S. Pat. No. 2,897,237. Specifically, a mixture of 93 g of ethylbenzene and 2 g of anhydrous ferric chloride is cooled to −5° C., and to it is added a solution of 61 g of 2,5-dichloro-2,5-dimethylhexane in 83 g of ethylbenzene during 30 min., maintaining the temperature at −5° C. and agitating continuously. The solution is quenched in water, washed to neutrality and distilled to yield, in addition to the excess of ethylbenzene, 1,1,4,4-tetramethyl-6-ethyl-1,2,3,4-tetrahydronaphthalene.

To convert 1,1,4,4-tetramethyl-6-ethyl-1,2,3,4-tetrahydronaphthalene to its corresponding 7-carboxaldehyde, 40 ml methylene chloride and 19.0 g $TiCl_4$ are charged in a 100 ml 3-necked round-bottomed flask equipped with addition tunnel, thermocouple and mechanical stirrer, and purged with nitrogen. The solution is cooled to 0° C. Next, 1,1,4,4-tetramethyl-6-ethyl-1,2,3,4-tetrahydronaphthalene (13.0 g) is dissolved in 40 ml methylene chloride and added during ten minutes with stirring at 0° C. After 5 min of additional stirring, α,α-dichloromethyl methyl ether (6 g) is added dropwise over a period of one hour at 0° C. The solution is stirred for two hours additionally, and then quenched with crushed ice (50 g). The solution is transferred to a separatory funnel, the organics washed twice with methylene chloride (10 ml each time), then twice with water (10 ml), dried over anhydrous sodium sulfate, filtered, and rotary evaporated to yield a crude product containing the 7-carboxaldehyde, 7-formyl-1,1,4,4-tetramethyl-6-ethyl-1,2,3,4-tetrahydronaphthalene. This material is then distilled to remove residual starting material and used in the next step.

To convert the 7-carboxaldehyde to its corresponding formate ester, a 250 ml 3-necked round bottomed flask equipped with a thermocouple, mechanical stirrer, and Claisen adapter (which is connected to an addition funnel and condenser), is charged with 16.57 g of meta-chloroperbenzoic acid (60% purity from Aldrich Chemical Company, Inc., Milwaukee, Wis.) and 70 ml of dichloromethane. The mixture is stirred for 10 minutes at 22° C., and then cooled to 11° C. To this reaction mixture is added dropwise a solution of 9.8 g of the 7-formyl-1,1,4,4-tetramethyl-6-ethyl-1,2,3,4-tetrahydronaphthalene in 30 ml of dichloro-methane. During the addition, which takes 1.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing the 1,1,4,4-tetramethyl-6-ethyl-1,2,3,4-tetrahydronaphthalene-7-ol formate ester.

EXAMPLE 6

Preparation of
1,1,2,4,4,5,7-Heptamethyl-1,2,3,4-Tetrahydronaphthalene-6-ol Formate Ester and
1,1,2,4,4,5,6-Heptamethyl-1,2,3,4-Tetrahydronaphthalene-7-ol Formate Ester The starting materials 6-formyl-1,1,2,4,4,5,7-heptamethyl-1,2,3,4-tetrahydronaphthalene and 7-formyl-1,1,2,4,4,5,6-heptamethyl-1,2,3,4-tetrahydronaphthalene are prepared by substantially following the procedures of Fehr et al., U.S. Pat. No. 5,162,588. Specifically, in a 2 liter flask equipped with a mechanical stirrer and kept under nitrogen, a solution of tiglic acid (100.0 g) in sulfuric ether (300 ml) is added to a suspension of LiAlH$_4$ (28.5 g) in ether (300 ml) over 3 hrs while maintaining the temperature at 5° C. The reaction mixture is made to reflux for 1 hr and then left under stirring, at room temperature, for one night. After cooling with an ice bath, 100 ml of 5% HCl is added dropwise, followed by 600 ml of 15% HCl and 200 ml of ether to avoid agglomeration. The reaction mixture is extracted with sulfuric ether (3×400 ml) and the combined extracts are washed, in succession, with a saturated solution of NaCl (3×50 ml), 10% Na$_2$CO$_3$ (20 ml), and H$_2$O. The organic phases are collected together, dried over Na$_2$SO$_4$ and evaporated to concentrate (40° C./9.7×10$^4$ Pa). The residue is fractionated in a Vigreux column under normal vacuum to yield 2-methyl-2-buten-1-ol.

In a 3 liter flask equipped with a mechanical stirrer and a condenser, kept under nitrogen, a mixture of triethylorthoacetate (1117.8 g), propionic acid (2.3 g) and 2-methyl-2-buten-1-ol (59.3 g) is heated at 118° C. for 72 hr in order to distill the ethanol gradually as it is formed. The excess of triethylorthoacetate is recovered and the distillation completed under reduced pressure. The raw product thus obtained contains the desired pentenoate. Purification on a Fischer column yields more purified ethyl 3,4-dimethyl-4-pentenoate.

In a flask equipped with a mechanical stirrer, a thermometer, an introduction ampoule and maintained under nitrogen, 52.0 g of the ethyl-3,4-dimethyl-4-pentenoate compound is added dropwise, over 1 hr, to a suspension of AlCl$_3$ (115.04 g) in 1,2,3-trimethylbenzene (359.99 g), while keeping the temperature at 0° C.-5° C. Once the introduction is completed, the temperature is allowed to increase to 20° C. and, 15 min. later, the reaction mixture is poured on icy water. The mixture is extracted with ether and washed successively with 5% NaOH, water, and a saturated NaCl solution. It is then dried over Na$_2$SO$_4$ filtered and the solvents evaporated. The excess of 1,2,3-trimethylbenzene is distilled at 70° C./2.66×10$^3$ Pa. Distillation of the residue at 160° C./2.66×10$^2$ Pa provides ethyl-3,4-dimethyl-4-(3,4,5-trimethyl-1-phenyl)pentanoate.

A 1.5 liter sulfuration flask equipped with a condenser and kept under nitrogen is charged with 15.12 g of Mg covered with anhydrous ether (20 ml). The Grignard reaction is triggered by adding 5 to 10 ml of a CH$_3$I (96.56 g) solution in ether (180 ml). As soon as the reaction starts (ether reflux), an ether solution (200 ml) of ethyl-3,4-dimethyl-4-(3,4,5-trimethyl-1-phenyl)pentanoate (69.0 g) is added to the reaction mixture. The CH$_3$I solution is continuously added while controlling the ether reflux with a cold water bath (solution added over about 1 hr). The mixture is allowed to react for 1 hr while the temperature is maintained at 20° C., and then carefully hydrolyzed with icy water. The product is then extracted with ether, washed with saturated NaCl, dried over Na$_2$SO$_4$, filtered and the solvents evaporated, to yield 2,4,5,5-tetramethyl-5-(3,4,5-trimethyl-1-phenyl)-2-pentanol.

A 250 ml three-neck flask equipped with a mechanical stirring and kept under N$_2$, is then charged with 100 g of 90% H$_2$SO$_4$, to which a solution of 2,4,5,5-tetramethyl-5-(3,4,5-trimethyl-1-phenyl)-2-pentanol (65.1 g) in petroleum ether at a temperature of 80° C.-100° C. ($\approx$50 ml) is added dropwise over about 1 hr, while maintaining the temperature of the solution between 0° C. and 10° C. Once the introduction is completed, the temperature is allowed to increase to 20° C. and, 30 min later, the H$_2$SO$_4$ is decanted and ice water is added to the reaction mixture ($\approx$300 ml). The latter is extracted with ether, washed with 10% NaOH and saturated NaCl, dried over Na$_2$SO$_4$, filtered and evaporated. Recrystallization of the raw product in ethanol afforded 1,1,2,4,4,5,6,7-octamethyl-1,2,3,4-tetrahydronaphthalene.

Next a halogenation reaction is carried out using the reagents N bromosuccinimide (NBS) (28.82 g), 1,1,2,4,4,5,6,7-octamethyl-1,2,3,4-tetrahydronaphthalene (35 g) and CCl$_4$ (350 ml), to yield raw product. This raw product is then used in a hydrolysis reaction with N-methyl-pyrrolidone (300 ml) and H$_2$O (45 ml), to yield a product containing the alcohols 1,1,2,4,4,5,7-heptamethyl-1,2,3,4-tetrahydronaphthalene-6-methanol and 1,1,2,4,4,5,6-heptamethyl-1,2,3,4-tetrahydronaphthalene-7-methanol.

To convert the alcohols to their corresponding carboxaldehydes, the mixture of alcohols (44.0 g) is oxidized using pyridinium chlorochromate (44.9 g) and CH$_2$Cl$_2$ (300 ml), and the resultant solution filtered to yield 6-formyl-1,1,2,4,4,5,7-heptamethyl-1,2,3,4-tetrahydronaphthalene and 7-formyl-1,1,2,4,4,5,6-heptamethyl-1,2,3,4-tetrahydronaphthalene.

To prepare the corresponding formate esters from the carboxaldehydes, a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.4 g of the mixture of 6-formyl-1,1,2,4,4,5,7-heptamethyl-1,2,3,4-tetrahydronaphthalene and 7-formyl-1,1,2,4,4,5,6-heptamethyl-1,2,3,4-tetrahydronaphthalene in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,2,4,4,5,7-heptamethyl-1,2,3,4-tetrahydronaphthalene-6-ol formate ester and 1,1,2,4,4,5,6-heptamethyl-1,2,3,4-tetrahydronaphthalene-7-ol formate ester. These two products may then be separated using preparative chromatography.

EXAMPLE 7

Preparation of 1,1,2,3,4,4,7-Heptamethyl-1,2,3,4-Tetrahydronaphthalene-6-ol Formate Ester The starting material 6-formyl-1,1,2,3,4,4,7-heptamethyl-1,2,3,4-tetrahydronaphthalene is prepared by substantially following the procedures of Fehr et al., U.S. Pat. No. 5,162,588. Specifically, a 1 liter flask equipped with a mechanical stirrer, a thermometer, and a condenser, and maintained under nitrogen, is charged at 20° C. with, successively, recently distilled isoprene (30.0 g), PrMgBr [(Pr=propyl, 1.88N, 213 ml; prepared from PrBr) (54.2 g), Mg (12.7 g) and $(CH_3CH_2)_2O$ (200 ml)], and dicyclopentadienyltitanium chloride ($Cp_2TiCl_2$) (available from Fluka Chemical Corp., Ronkonkoma, N.Y., 1 g). After 15 hrs at 20° C., the solution is transferred via canula into a cooled 1.5 liter flask (−10° C.) containing pivaloyl chloride (53.0 g) in solution in $(CH_3CH_2)_2O$ (100 ml). After stirring for 1 hr, the mixture is poured on saturated $NH_4Cl$, extracted with ether and the organic layers are washed with 5% NaOH, $H_2O$ and saturated NaCl. They are then dried over $Na_2SO_4$, filtered and evaporated under vacuum, to obtain 49.2 g of a yellow liquid, which is then distilled on a bridge (50° C./$1.33 \times 10^3$ Pa) to obtain the 2,2,4,5-tetramethyl-5-hexen-3-one.

A solution of 2,2,4,5-tetramethyl-5-hexen-3-one in o-xylene (50 ml) is then added dropwise to a suspension of $AlCl_3$ (36.2 g) in o-xylene (380 ml) over 1 hr while maintaining the temperature at 0° C. The temperature is allowed to increase to 10° C. (around 30 min) and the reaction mixture is poured on $H_2O$, extracted with ether, and washed with $Na_2SO_3$ and then with saturated NaCl. After drying over $Na_2SO_4$ and concentration by distillation on a bridge, 5-(3,4-dimethyl-1-phenyl)-2,2,4,5-tetramethyl-3-hexanone is obtained.

In a 1 liter flask equipped with mechanical stirring, a thermometer and a condenser, and maintained under nitrogen, a solution of 5-(3,4-dimethyl-1-phenyl)-2,2,4,5-tetramethyl-3-hexanone (54.4 g) in $(CH_3CH_2)_2O$ (50 ml) is added to a suspension of $LiAlH_4$ (3.80 g) in $(CH_3CH_2)_2O$ (250 ml). After cooling to 10° C., 4 ml of water are carefully added dropwise, then 4 ml of 5% NaOH and 12 ml of water. The resulting alcohol, 5-(3,4-dimethyl-1-phenyl)-2,2,4,5-tetramethyl-3-hexanol, is then filtered, concentrated and distilled (bridge: 130° C.–140° C./$2.0 \times 10^2$ Pa).

The alcohol, 5-(3,4-dimethyl-1-phenyl)-2,2,4,5-tetramethyl-3-hexanol (41.6 g), is next added under stirring and external cooling to a mixture of methanesulfonic acid (21.25 g) and $P_2O_5$ (8.5 g). The temperature is kept at 40° C. for 4 hrs. The reaction mixture is cooled, rendered more fluid by adding $CH_2Cl_2$ (10 ml) and transferred into a 1 liter beaker containing an ice-water mixture. The hydrocarbon formed in the reaction is extracted with ether, washed with 5% NaOH, $H_2O$, then saturated NaCl, dried over $Na_2SO_4$ and concentrated. Following crystallization from ethanol and distillation, the compound 1,1,2,3,4,4,6,7-octamethyl-1,2,3,4-tetrahydronaphthalene is obtained.

To prepare the corresponding 6-carboxaldehyde, 16 portions of $Ce(NH_4)_2(NO_3)_6$ ($16 \times 16.0$ g=256.0 g) in methanol ($16 \times 100$ ml) is added to a solution of 1,1,2,3,4,4,6,7-octamethyl-1,2,3,4-tetrahydronaphthalene (16.0 g) in methanol (700 ml), over 8 hrs, while maintaining the temperature at 50° C. After about ½ of the methanol is evaporated, the resulting product is extracted with petroleum ether 30° C.–50° C./saturated NaCl. After crystallizing in ethanol, treating the mother liquors and recrystallizing, the desired 6-carboxaldehyde, 6-formyl-1,1,2,3,4,4,7-heptamethyl-1,2,3,4-tetrahydronaphthalene is obtained.

To prepare the corresponding formate ester from the 6-carboxaldehyde, a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.4 g of the aldehyde in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,2,3,4,4,7-heptamethyl-1,2,3,4-tetrahydronaphthalene-6-ol formate ester which may be further purified using standard fractional distillation techniques.

EXAMPLE 8

Preparation of 1,1,3,4,4,5,7-Heptamethyl-1,2,3,4-tetrahydronaphthalene-6-ol Formate Ester The starting material 6-formyl-1,1,3,4,4,5,7-heptamethyl-1,2,3,4-tetrahydronaphthalene is prepared by substantially following the procedures of Fehr et al., U.S. Pat. No. 5,162,588. Specifically, in a 3000 ml flask mechanically stirred and equipped with a condenser and a $N_2$ inlet, a solution of sodium ethylate (46.0 g Na, 700 ml absolute ethanol) is prepared and 286.0 g of ethyl acetoacetate added thereto, over 30 min at a temperature of 15° C. The mixture is stirred for 30 min at room temperature, and 182.0 g β-methallyl chloride is added all at once, at the same temperature. Stirring is maintained for 50 hrs and the mixture is then refluxed for 1 hr. The sodium chloride precipitate is filtered and the filtrate is concentrated by solvent evaporation. Residue (402.6 g) is fractionated on a Vigreux column, then on a column filled with glass helices topped by a total reflux head, to yield ethyl-2-acetyl-4-methyl-4-pentenoate, which is then used in the following reaction.

A 2000 ml flask, equipped with mechanical stirring, a condenser and $N_2$ atmosphere, is charged with 24.3 g of N₂ and 400 ml of ethanol to prepare sodium ethylate. After cooling to 15° C., the ethyl-2-acetyl-4-methyl-4-pentenoate (161.4 g) is added to the solution over 30 min while maintaining the temperature at 15° C.-20° C. To this is then added, all at once, 15 g of iodide. The exothermic reaction is controlled with an ice bath to keep the temperature at 30° C. for about 90 min. Stirring is continued over 2 hrs and 30 min at 20° C., and the mixture is then taken to reflux for 4 hrs. The reaction mixture is left at rest for 56 hrs, and then the NaI precipitate is filtered. Toluene (700 ml) is added and the mixture filtered again. Toluene/ethanol azeotrope (700 ml) (rotavapor. 74° C./6×10⁴ Pa) is distilled and 250 ml of the distillate is added to the residue. After cooling to 5° C., a new filtration is carried out. The filtrate is evaporated (74° C./2.7×10⁴ Pa). Raw product is purified on a Vigreux column, and then in a glass bolos column topped by a total reflux head, to yield ethyl-2-acetyl-2,4-dimethyl-4-pentenoate.

Next, the ethyl-2-acetyl-2,4-dimethyl-4-pentenoate (56.5 g) is reacted with AlCl₃ (125.2 g), and 1,2,3-trimethyl-benzene (390.9 g), to yield, after distillation, ethyl 2,4-dimethyl-(3,4,5-trimethyl-1-phenyl)-pentanoate.

A 1.5 liter sulfuration flask equipped with a condenser and kept under nitrogen is charged with 17.7 g of Mg covered with anhydrous ether (50 ml). The Grignard reaction is triggered by adding 5 to 10 ml of a CH₃I (108.9 g) solution in ether (250 ml). As soon as the reaction starts (ether reflux), an ether solution (350 ml) of ethyl-2,4-dimethyl-(3,4,5-trimethyl-1-phenyl)pentanoate (81.5 g) is added to the reaction mixture. The CH₃I solution is continuously added while controlling the ether reflux with a cold water bath (solution added over about 1 hr). The mixture is allowed to react for 1 hr while the temperature is maintained at 20° C., and then carefully hydrolyzed with icy water. The product is then extracted with ether, washed with saturated NaCl, dried over Na₂SO₄, filtered and the solvents evaporated, to yield 2,3,5,5-tetramethyl-5-(3,4,5-trimethyl-1-phenyl)-2-pentanol.

A 250 ml three-neck flask equipped with a mechanical stirring and kept under N₂, is then charged with 100 g of 90% H₂SO₄, to which a solution of 2,3,5,5-tetramethyl-5-(3,4,5-trimethyl-1-phenyl)-2-pentanol (82 g) in petroleum ether at a temperature of 80° C.-100° C. (≈50 ml) is added dropwise over about 1 hr, while maintaining the temperature of the solution between 0° C. and 10° C. Once the introduction is completed, the temperature is allowed to increase to 20° C. and, 30 min later, the H₂SO₄ is decanted and ice water is added to the reaction mixture (≈300 ml). The latter is extracted with ether, washed with 10% NaOH and saturated NaCl, dried over Na₂SO₄, filtered and evaporated. Recrystallization of the raw product in ethanol affords 1,1,2,4,4,6,7,8-octamethyl-1,2,3,4-tetrahydronaphthalene.

Next a halogenation reaction is carried out using the reagents N-bromosuccinimide (NBS) (38.29 g), 1,1,2,4,4,6,7,8-octamethyl-1,2,3,4-tetrahydronaphthalene (50 g) and CCl₄ (400 ml), to yield raw product. This raw product (54.2 g) is then used in a hydrolysis reaction with N-methyl-pyrrolidone (300 ml) and H₂O (45 ml), to yield a product containing the alcohol 1,1,2,4,4,6,8-heptamethyl-1,2,3,4-tetrahydronaphthalene-7-methanol.

To prepare the corresponding 7-carboxaldehyde from the alcohol, 1,1,2,4,4,6,8-heptamethyl-1,2,3,4-tetrahydronaphthalene-7-ol (39.1 g) is oxidized using pyridinium chlorochromate (44.9 g) and CH₂Cl₂ (300 ml), and the resultant solution filtered to yield 7-formyl-1,1,2,4,4,6,8-heptamethyl-1,2,3,4-tetrahydronaphthalene.

To prepare the corresponding formate ester from the 7-carboxaldehyde, a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.4 g of the aldehyde in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,2,4,4,6,8-heptamethyl-1,2,3,4-tetrahydronaphthalene-7-ol formate ester, which may be further purified using standard fractional distillation techniques, or preparative gas chromatography.

EXAMPLE 9

Preparation of
4-Ethyl-1,1,2,4,5,7-Hexamethyl-1,2,3,4-Tetrahydronaphthalene-6-ol Formate Ester Ethylmagnesium bromide in tetrahydrofuran (1.0M, 100 ml) (which may be obtained from Aldrich Chemical Company, Inc., Milwaukee, Wis.) is added at room temperature to a 250 ml four-necked round bottom flask equipped with an air stirrer, septum, Claisen adapter (thermocouple and dry ice condenser attached) and nitrogen inlet tube. To this is then slowly added 2,4-dimethylacetophenone (14.8 g) (which may be obtained from Aldrich Chemical Company, Inc., Milwaukee, Wis.). After about 2 hours, an aliquot of additional Grignard (20 ml) is added. The solution is then heated at 60° C. for about one hour, and quenched with aqueous NH₄Cl. The aqueous layer is then washed several times with methyl tert-butyl ether and rotoevaporated to yield a crude product mixture containing 1-[2',4'-dimethylphenyl]-1-methyl-1-propanol. The product mixture is then fractionated under reduced pressure to further purify 1-[2',4'-dimethylphenyl]-1-methyl-1-propanol.

Next, 1-[2',4'-dimethylphenyl]-1-methyl-1-propanol is converted to 4-ethyl-1,1,2,4,5,7-hexamethyl-1,2,3,4-tetrahydronaphthalene by following procedures similar to those described in European Patent Application Publication No. 0 393 742. Specifically, to a stirred solution of 10 ml TiCl₄ in 120 ml dichloromethane (cooled to −5° C. under nitrogen), is added a mixture of 17.8 g of 1-[2',4'-dimethylphenyl]-1-methyl-1-propanol and 16 8 g 2,3-dimethylbutene-1 over a two hour period. The reaction mixture is stirred for a further 30 mins at −5° C. Thereafter, it is poured into a mixture of 200 ml of water and 100 ml of concentrated hydrochloric acid and stirred for 15 mins. The organic phase is separated and the aqueous phase washed twice with 50 ml dichloromethane. The combined organic phase is washed twice with 100 ml 10% hydrochloric acid solution, once with 100 ml water, twice with 100 ml 5% sodium carbonate solution, and finally once again with water, to yield as a crude product, 4-ethyl-1,1,2,4,5,7-hexamethyl-1,2,3,4-tetrahydronaphthalene. After removal of the solvent, the crude product is further purified by fractional distillation under reduced pressure.

To convert 4-ethyl-1,1,2,4,5,7-hexamethyl-1,2,3,4-tetrahydronaphthalene to its corresponding 6-carboxaldehyde, a 250 ml flask is charged with 130 ml dichloromethane and 24.51 g TiCl$_4$. The solution is cooled to 2° C. and 14.69 g of 4-ethyl-1,1,2,4,5,7-hexamethyl-1,2,3,4-tetrahydronaphthalene and 20 ml dichloromethane are added with stirring. Then α,α-dichloromethyl methyl ether (13.37 g) is added over a period of 1.2 hours. After completion of addition, the solution is allowed to warm to room temperature. After a further half hour, the solution is quenched with water at a temperature of ≦8° C. The solution is distilled to remove residual starting material to yield a crude product containing the 6-carboxaldehyde, 6- formyl-4-ethyl-1,1,2,4,5,7-hexamethyl-1,2,3,4-tetrahydronaphthalene.

To convert the 6-carboxaldehyde to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of metachloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.48 g of 6-formyl-4-ethyl-1,1,2,4,5,7-hexamethyl-1,2,3,4-tetrahydronaphthalene in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 4-ethyl-1,1,2,4,5,7-hexamethyl-1,2,3,4-tetrahydronaphthalene-6-ol formate ester. The crude product may then be further purified using standard fractional distillation techniques.

EXAMPLE 10

Preparation of 5-Ethyl-1,1,2,4,4,7-Hexamethyl-1,2,3,4-Tetrahydronaphthalene-6-ol Formate Ester Using a Perrier modification, Perrier, *Chem. Ber.*, Vol. 33, pp. 819 et seq. (1900), Perrier, *Bull. Soc. Chim. France* pp. 859 et seq. (1904), 3-ethyltoluene (120.0 g) is reacted with acetyl chloride (72.0 g), methylene chloride (500 ml), and aluminum chloride (145.0 g) to provide a mixture of 2-ethyl-4-methylacetophenone and 2-methyl-4-ethyl-acetophenone. After standard quenching, separation, drying and solvent evaporation, the mixture is distilled on a spinning band distillation column under vacuum to separate the components.

Methylmagnesium bromide (3.0M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 2-ethyl-4-methylacetophenone (22.26 g). After about 2 hours, an aliquot of additional Grignard (20 ml) is added. The solution is then heated at 60° C. for about one hour, and quenched with aqueous NH$_4$Cl. The aqueous layer is then washed several times with methyl tert-butyl ether and rotoevaporated to yield a crude product mixture containing 1-[2′-ethyl-4′-methylphenyl] -1-methylethanol. The product mixture is then fractionated under reduced pressure to further purify 1-[2′-ethyl-4′-methylphenyl]-1-methylethanol. () Next, 1-[2′-ethyl-4′-methylphenyl]-1-methylethanol is converted to 5-ethyl-1,1,2,4,4,7-hexamethyl-1,2,3,4-tetrahydronaphthalene by following procedures similar to those described in European Patent Application Publication No. 0 393 742. Specifically, to a stirred solution of 10 ml TiCl$_4$ in 120 ml dichloromethane (cooled to −5° C. under nitrogen), is added a mixture of 17.8 g of 1-[2′-ethyl-4′-methylphenyl]-1-methylethanol and 16.8 g 2,3-dimethylbutene-1 over a two hour period. The reaction mixture is stirred for a further 30 mins at −5° C. Thereafter, it is poured into a mixture of 200 ml of water and 100 ml of concentrated hydrochloric acid and stirred for 15 mins. The organic phase is separated and the aqueous phase washed twice with 50 ml dichloromethane. The combined organic phase is washed twice with 100 ml 10% hydrochloric acid solution, once with 100 ml water, twice with 100 ml 5% sodium carbonate solution, and finally once again with water, to yield as a crude product, 5-ethyl-1,1,2,4,4,7-hexamethyl-1,2,3,4-tetrahydronaphthalene. After removal of the solvent, the crude product is further purified by fractional distillation under reduced pressure.

To convert 5-ethyl-1,1,2,4,4,7-hexamethyl-1,2,3,4-tetrahydronaphthalene to its corresponding 6-carboxaldehyde, a 250 ml flask is charged with 130 ml dichloromethane and 24.51 g TiCl$_4$. The solution is cooled to 2° C. and 14.69 g of 5-ethyl-1,1,2,4,4,7-hexamethyl-1,2,3,4-tetrahydronaphthalene and 20 ml dichloromethane are added with stirring. Then α,α-dichloromethyl methyl ether (13.37 g) is added over a period of 1.2 hours. After completion of addition, the solution is allowed to warm to room temperature. After a further half hour, the solution is quenched with water at a temperature of ≦8° C. The solution is distilled to remove residual starting material to yield a crude product containing the 6-carboxaldehyde, 6-formyl-5-ethyl-1,1,2,4,4,7-hexamethyl-1,2,3,4-tetrahydronaphthalene.

To convert the 6-carboxaldehyde to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of metachloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.48 g of 6-formyl-5-ethyl-1,1,2,4,4,7-hexamethyl 1,2,3,4-tetrahydronaphthalene in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 5-ethyl-1,1,2,4,4,7-hexamethyl-1,2,3,4-tetrahydronaphthalene-6-ol formate ester. The crude product may then be further purified using standard fractional distillation techniques.

EXAMPLE 11

Preparation of
7-Ethyl-1,1,2,4,4,5-Hexamethyl-1,2,3,4-Tetrahydronaphthalene-6-ol Formate Ester Using a Perrier modification, Perrier, *Chem. Ber.*, Vol. 33, pp. 819 et seq. (1900), Perrier, *Bull. Soc. Chim. France*, pp. 859 et seq. (1904), 3-ethyltoluene (120.0 g) is reacted with acetyl chloride (72.0 g), methylene chloride (500 ml), and aluminum chloride (145.0 g) to provide a mixture of 2-ethyl-4-methylacetophenone and 2-methyl-4-ethyl-acetophenone. After standard quenching, separation, drying and solvent evaporation, the mixture is distilled on a spinning band distillation column under vacuum to separate the components.

Methylmagnesium bromide (3.0M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 2-methyl-4-ethyl-acetophenone (22.26 g). After about 2 hours, an aliquot of additional Grignard (20 ml) is added. The solution is then heated at 60° C. for about one hour, and quenched with aqueous NH$_4$Cl. The aqueous layer is then washed several times with methyl tert-butyl ether and rotoevaporated to yield a crude product mixture containing 1-[4'-ethyl-2'-methylphenyl]-1-methylethanol. The product mixture is then fractionated under reduced pressure to further purify 1-[4'-ethyl-2'-methylphenyl]-1-methylethanol.

Next, 1-[4'-ethyl-2'-methylphenyl]-1-methylethanol is converted to 7-ethyl-1,1,2,4,4,5-hexamethyl-1,2,3,4-tetrahydronaphthalene by following procedures similar to those described in European Patent Application Publication No. 0 393 742. Specifically, to a stirred solution of 10 ml TiCl$_4$ in 120 ml dichloromethane (cooled to −5° C. under nitrogen), is added a mixture of 17.8 g of 1-[4'-ethyl-2'-methylphenyl]-1-methylethanol and 16.8 g 2,3-dimethylbutene-1 over a two hour period. The reaction mixture is stirred for a further 30 mins at −5° C. Thereafter, it is poured into a mixture of 200 ml of water and 100 ml of concentrated hydrochloric acid and stirred for 15 mins. The organic phase is separated and the aqueous phase washed twice with 50 ml dichloromethane. The combined organic phase is washed twice with 100 ml 10% hydrochloric acid solution, once with 100 ml water, twice with 100 ml 5% sodium carbonate solution, and finally once again with water, to yield as a crude product, 7-ethyl-1,1,2,4,4,5-hexamethyl-1,2,3,4-tetrahydronaphthalene. After removal of the solvent, the crude product is further purified by fractional distillation under reduced pressure.

To convert 7-ethyl-1,1,2,4,4,5-hexamethyl-1,2,3,4-tetrahydronaphthalene to its corresponding 6-carboxaldehyde, a 250 ml flask is charged with 130 ml dichloromethane and 24.51 g TiCl$_4$. The solution is cooled to 2° C. and 14.69 g of 7-ethyl-1,1,2,4,4,5-hexamethyl-1,2,3,4-tetrahydronaphthalene and 20 ml dichloromethane are added with stirring. Then α,α-dichloromethyl methyl ether (13.37 g) is added over a period of 1.2 hours. After completion of addition, the solution is allowed to warm to room temperature. After a further half hour, the solution is quenched with water at a temperature of ≦8° C. The solution is distilled to remove residual starting material to yield a crude product containing the 6-carboxaldehyde, 6-formyl-7-ethyl-1,1,2,4,4,5-hexamethyl-1,2,3,4-tetrahydronaphthalene.

To convert the 6-carboxaldehyde to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.48 g of 6-formyl-7-ethyl-1,1,2,4,4,5-hexamethyl-1,2,3,4-tetrahydronaphthalene in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 7-ethyl-1,1,2,4,4,5-hexamethyl-1,2,3,4-tetrahydronaphthalene-6-ol formate ester. The crude product may then be further purified using standard fractional distillation techniques.

EXAMPLE 12

Preparation of
1,1,4,4,7-Pentamethyl-5-Methoxy-1,2,3,4-Tetrahydronaphthalene-6-ol Formate Ester The starting material 6-formyl-1,1,4,4,7-pentamethyl-1,2,3,4-tetrahydronaphthalene is prepared by substantially following the procedures of Willis et al., U.S. Pat. No. 4,605,778. Specifically, concentrated hydrochloric acid (8.260 g, 86 mol) is added in one portion to 2,5-dimethyl-2,5-hexane diol (4.478 g, 46.65 mol). The resulting solution is heated for 6 hr, with stirring, at 22° C.-75° C., while passing hydrogen chloride gas (200 g). Next, the reaction mixture is cooled to 25° C., hexane (3.5 liter) added, and the mixture stirred vigorously. The organic layer is separated, washed with water (2×1 liter), neutralized with 5% sodium bicarbonate solution and dried (Na$_2$SO$_4$). The solvent is removed by distillation and the residue crystallized from hexane to yield 2,5-dimethyl-2,5-dichlorohexane.

Next, 2,5-dimethyl-2,5-dichlorohexane (183 g, 1 mol) is stirred with m-cresol (129.6 g, 1.2 mol) and aluminum chloride (4 g) is added. The mixture is heated at 95° C., with stirring, for 1.5 hr, after which ethylene dichloride (100 ml) is added, and then the heating continued. After 1 hr, the mixture is cooled to 20° C., and poured onto an ice water/hydrochloric acid mixture (150 ml, 10% HCl solution). The mixture is then extracted with toluene (500 ml), the organic layer separated, washed with brine (3×50 ml) and dried (Na$_2$SO$_4$). The solvent is removed by distillation and the residue crystallized from a hexane/benzene solvent mixture to give 1,1,4,4,7-pentamethyl-5-hydroxy-1,2,3,4-tetrahydronaphthalene.

To prepare 1,1,4,4,7-pentamethyl-5-methoxy-1,2,3,4-tetrahydronaphthalene, a solution of sodium hydroxide (38 g, 0.95 mol) in water (1 liter) is added to a mixture of 1,1,4,4,7-pentamethyl-5-hydroxy 1,2,3,4-tetrahydronaphthalene (109 g. 0.5 mol), dimethyl sulfate (126 g, 1 mol) and methyltrialkyl($C_8$–$C_{10}$) ammonium chloride (Adogen 464 TM; available from Sherex Corp., Dublin, Ohio) in methylene dichloride (2 liters). The reaction mixture is stirred vigorously at 25° C.–28° C. for 1 hr, after which time the organic layer is separated, combined with ammonium hydroxide solution (500 ml, 10%), and stirred vigorously at 20° C.–25° C. for 0.5 hr. The organic layer is then separated, and the washing procedure repeated, after which the organic layer is separated, washed with water (2×100 ml), then with brine (50 ml), and dried ($Na_2SO_4$). The solvent is removed by distillation and the residue is crystallized from hexane yielding 1,1,4,4,7-pentamethyl-5-methoxy-1,2,3,4-tetrahydronaphthalene.

To prepare the corresponding 6-carboxaldehyde, 6-formyl-1,1,4,4,7-pentamethyl-5-methoxy-1,2,3,4-tetrahydronaphthalene, 1,1,4,4,7-pentamethyl-5-methoxy-1,2,3,4-tetrahydronaphthalene (50 g, 0.2155 mol) is added to a stirred mixture of hexamethylenetetramine (31.4 g, 0.224 mol) and trifluoroacetic acid (250 ml) at 35° C.–40° C. under a nitrogen atmosphere. The stirred reaction mixture is heated to 85° C.–90° C., and maintained at this temperature for 1.5 hr. Trifluoroacetic acid is removed by distillation and the residue is poured onto an ice-water mixture (800 ml). The mixture is then stirred for 0.5 hr, neutralized with a 10% sodium carbonate solution, and the product extracted with benzene (2×150 ml). The combined extracts are washed with brine (50 ml) and dried ($Na_2SO_4$). The solvent is then removed by distillation and the residue crystallized from hexane to provide the 6-carboxaldehyde, 6-formyl-1,1,4,4,7-pentamethyl-5-methoxy-1,2,3,4-tetrahydronaphthalene.

To convert the 6-carboxaldehyde to its corresponding formate ester, the following procedure is carried out. A 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.48 g of 6-formyl-1,1,4,4,7-pentamethyl-5-methoxy-1,2,3,4-tetrahydronaphthalene in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,4,4,7-pentamethyl-5-methoxy-1,2,3,4-tetrahydronaphthalene-6-ol formate ester. The crude product may then be further purified using standard fractional distillation techniques.

EXAMPLE 13

Preparation of 1,1,4,4,7-Pentamethyl-5-Methoxy-1,2,3,4-Tetrahydronaphthalene-6-ol Formate Ester The starting material 6-formyl-1,1,4,4,7-pentamethyl-1,2,3,4-tetrahydronaphthalene is prepared by substantially following the procedures of Willis et al., U.S. Pat. No. 4,605,778. Specifically, concentrated hydrochloric acid (8.260 g, 86 mol) is added in one portion to 2,5-dimethyl-2,5-hexane diol (4.478 g, 46.65 mol). The resulting solution is heated for 6 hr, with stirring, at 22° C.–75° C., while passing hydrogen chloride gas (200 g). Then the reaction mixture is cooled to 25° C., hexane (3.5 liter) added, and the mixture stirred vigorously. The organic layer is separated, washed with water (2×1 liter), neutralized with 5% sodium bicarbonate solution and dried ($Na_2SO_4$). The solvent is removed by distillation and the residue crystallized from hexane to yield 2,5-dimethyl-2,5-dichlorohexane.

Next, 2,5-dimethyl-2,5-dichlorohexane (183 g, 1 mol) is stirred with m-cresol (129.6 g, 1.2 mol) and aluminum chloride (4 g) is added. The mixture is heated at 95° C., with stirring, for 1.5 hr, after which ethylene dichloride (100 ml) is added, and then the heating continued. After 1 hr, the mixture is cooled to 20° C., and poured onto an ice water/hydrochloric acid mixture (150 ml, 10% HCl solution). The mixture is then extracted with toluene (500 ml), the organic layer separated, washed with brine (3×50 ml) and dried ($Na_2SO_4$). The solvent is removed by distillation and the residue crystallized from a hexane/benzene solvent mixture to give 1,1,4,4,7-pentamethyl-5-hydroxy-1,2,3,4-tetrahydronaphthalene.

To prepare 1,1,4,4,7-pentamethyl-5-methoxy-1,2,3,4-tetrahydronaphthalene, a solution of sodium hydroxide (38 g, 0.95 mol) in water (1 liter) is added to a mixture of 1,1,4,4,7-pentamethyl-5-hydroxy-1,2,3,4-tetrahydronaphthalene (109 g. 0.5 mol), dimethyl sulfate (126 g, 1 mol) and methyltrialkyl($C_8$–$C_{10}$) ammonium chloride (Adogen 464 TM; available from Sherex Corp., Dublin, Ohio) in methylene dichloride (2 liters). The reaction mixture is stirred vigorously at 25° C.–28° C. for 1 hr, after which time the organic layer is separated, combined with ammonium hydroxide solution (500 ml, 10%), and stirred vigorously at 20° C.–25° C. for 0.5 hr. The organic layer is then separated, and the washing procedure repeated, after which the organic layer is separated, washed with water (2×100 ml), then with brine (50 ml), and dried ($Na_2SO_4$). The solvent is removed by distillation and the residue is crystallized from hexane yielding 1,1,4,4,7-pentamethyl-5-methoxy-1,2,3,4-tetrahydronaphthalene.

To prepare the corresponding 6-carboxaldehyde, 6-formyl-1,1,4,4,7-pentamethyl-5-methoxy-1,2,3,4-tetrahydronaphthalene, 1,1,4,4,7-pentamethyl-5-methoxy-1,2,3,4-tetrahydronaphthalene (23.2 g, 0.1 mol) is added to a stirred solution of acetic acid (18.2 g, 0.3 mol), 85% phosphoric acid (17.6 g, 0.15 mol), hydrochloric acid (28.7 g, 0.3 mol) and paraformaldehyde (7.3 g, 0.24 mol). The mixture is stirred and heated at 95° C. for 16 hr. The reaction mixture is then cooled to 25° C., benzene (50 ml) added, and stirred vigorously. The organic layer is separated, washed with water (2×25 ml), neutralized with 5% sodium bicarbonate solution, and dried ($Na_2SO_4$). The solvent is removed by distillation to provide 6-chloromethyl-1,1,4,4,7-pentamethyl-5-methoxy-1,2,3,4-tetrahydronaphthalene.

Next, sodium (2.87 g, 0.125 mol) is added in small pieces to methanol (40 ml) during 0.5 hr at 25° C.- 45° C., then nitropropane (13.35 g, 0.15 mol) is added. The mixture is heated with stirring at 65° C. during 0.25 hr, then a slurry of 6 chloromethyl-1,1,4,4,7-pentamethyl-5-methoxy-1,2,3,4-tetrahydronaphthalene (28 g, 0.1 mol) in methanol (50 ml) is added, in portions, during 0.25 hr at 65° C. The stirred mixture is heated at 65° C.–68° C. for 2.5 hr, after which excess methanol is removed by distillation. The residue is dissolved in benzene (100 ml) and the solution washed with water (3×25 ml), then with brine (25 ml), and dried ($Na_2SO_4$). The solvent is evaporated and the residue distilled to yield, after crystallization, the 6-carboxaldehyde, 6-formyl-1,1,4,4,7-pentamethyl-5-methoxy-1,2,3,4-tetrahydronaphthalene.

To convert the 6-carboxaldehyde to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.48 g of 6-formyl-1,1,4,4,7-pentamethyl-5-methoxy-1,2,3,4-tetrahydronaphthalene in 4 ml of dichloromethane. During the addition which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,4,4,7-pentamethyl-5-methoxy-1,2,3,4-tetrahydronaphthalene-6-ol formate ester. The crude product may then be further purified using standard fractional distillation techniques.

EXAMPLE 14

Preparation of 1,1,4,4,7-Pentamethyl-5-Methoxy-1,2,3,4-Tetrahydronaphthalene-6-ol Formate Ester The starting material 6-formyl-1,1,4,4,7-pentamethyl-5-hydroxy-1,2,3,4-tetrahydronaphthalene is prepared by substantially following the procedures of Willis et al., U.S. Pat. No. 4,605,778. Specifically, concentrated hydrochloric acid (8.260 g, 86 mol) is added in one portion to 2,5-dimethyl-2,5-hexane diol (4.478 g, 46.65 mol). The resulting solution is heated for 6 hr, with stirring, at 22° C.–75° C., while passing hydrogen chloride gas (200 g). Then the reaction mixture is cooled to 25° C., hexane (3.5 liter) added, and the mixture stirred vigorously. The organic layer is separated, washed with water (2×1 liter), neutralized with 5% sodium bicarbonate solution and dried ($Na_2SO_4$). The solvent is removed by distillation and the residue crystallized from hexane to yield 2,5-dimethyl-2,5-dichlorohexane.

Next, 2,5-dimethyl-2,5-dichlorohexane (183 g, 1 mol) is stirred with m cresol (129.6 g, 1.2 mol) and aluminum chloride (4 g) is added. The mixture is heated at 95° C., with stirring, for 1.5 hr, after which ethylene dichloride (100 ml) is added, and then the heating continued. After 1 hr, the mixture is cooled to 20° C., and poured onto an ice water/hydrochloric acid mixture (150 ml, 10% HCl solution). The mixture is then extracted with toluene (500 ml), the organic layer separated, washed with brine (3×50 ml) and dried ($Na_2SO_4$). The solvent is removed by distillation and the residue crystallized from a hexane/benzene solvent mixture to give 1,1,4,4,7-pentamethyl-5-hydroxy-1,2,3,4-tetrahydronaphthalene.

To prepare 6-formyl-1,1,4,4,7-pentamethyl-5-hydroxy-1,2,3,4-tetrahydronaphthalene, hexamethylenetetramine (21 g, 0.15 mol) and 1,1,4,4,7-pentamethyl-5-hydroxy-1,2,3,4-tetrahydronaphthalene are added in one portion, with stirring, to acetic acid (250 ml) and the mixture is heated at 95° C.-100° C. for 2 hrs. After cooling to 80° C.–85° C., water (250 ml) and concentrated hydrochloric acid (60 ml) are added and the mixture heated at 95° C.-100° C. for a further 2 hrs. The reaction product is then cooled to 20° C., diethyl ether (150 ml) is added, and the mixture stirred vigorously. The organic layer is separated, washed with brine (2×50 ml), neutralized with 5% sodium bicarbonate solution (100 ml), and dried ($Na_2SO_4$). The solvent is removed by distillation and the residue is distilled to yield 6-formyl-1,1,4,4,7-pentamethyl-5-hydroxy-1,2,3,4-tetrahydronaphthalene.

To prepare 6-formyl-1,1,4,4,7-pentamethyl-5-methoxy-1,2,3,4-tetrahydronaphthalene, a solution of sodium hydroxide (0.98 g, 0.0244 mol) in water (24 ml) is added in one portion to a solution of 6-formyl-1,1,4,4,7-pentamethyl-5-hydroxy-1,2,3,4-tetrahydronaphthalene (3 g, 0.0122 mol), dimethyl sulfate (3.07 g, 0.0244 mol) and methyltrialkyl($C_8$-$C_{10}$)ammonium chloride (Adogen 464 TM) (0.56 g) in methylene chloride (48 ml). The mixture is stirred vigorously at 38° C.–40° C. for 4 hrs. After cooling, the organic layer is separated, washed with brine (3×20 ml), and dried ($Na_2SO_4$). The solvent is removed by distillation and the residue is distilled to yield 6-formyl-1,1,4,4,7-pentamethyl-5-methoxy-1,2,3,4-tetrahydronaphthalene.

To convert the 6-carboxaldehyde, 6-formyl-1,1,4,4,7-pentamethyl-5-methoxy-1,2,3,4-tetrahydronaphthalene, to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.48 g of 6-formyl-1,1,4,4,7-pentamethyl-5-methoxy-1,2,3,4-tetrahydronaphthalene in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,4,4,7-pentamethyl-5-methoxy-1,2,3,4-tetrahydronaphthalene-6-ol formate ester. The crude product may then be further purified using standard fractional distillation techniques.

EXAMPLE 15

Preparation of
1,1,4,4,7-Pentamethyl-5-Hydroxy-1,2,3,4-Tetrahydronaphthalene-6-ol Formate Ester The starting material 6-formyl-1,1,4,4,7-pentamethyl-5-hydroxy-1,2,3,4-tetrahydronaphthalene is prepared by substantially following the procedures of Willis et al., U.S. Pat. No. 4,605,778. Specifically, concentrated hydrochloric acid (8.260 g, 86 mol) is added in one portion to 2,5-dimethyl-2,5-hexane diol (4.478 g, 46.65 mol). The resulting solution is heated for 6 hr, with stirring, at 22° C.–75° C., while passing hydrogen chloride gas (200 g). Then the reaction mixture is cooled to 25° C., hexane (3.5 liter) added, and the mixture stirred vigorously. The organic layer is separated, washed with water (2×1 liter), neutralized with 5% sodium bicarbonate solution and dried ($Na_2SO_4$). The solvent is removed by distillation and the residue crystallized from hexane to yield 2,5-dimethyl-2,5-dichlorohexane.

Next, 2,5-dimethyl-2,5-dichlorohexane (183 g, 1 mol) is stirred with m-cresol (129.6 g, 1.2 mol) and aluminum chloride (4 g) is added. The mixture is heated at 95° C., with stirring, for 1.5 hr, after which ethylene dichloride (100 ml) is added, and then the heating continued. After 1 hr, the mixture is cooled to 20° C., and poured onto an ice water/hydrochloric acid mixture (150 ml, 10% HCl solution). The mixture is then extracted with toluene (500 ml), the organic layer separated, washed with brine (3×50 ml) and dried ($Na_2SO_4$). The solvent is removed by distillation and the residue crystallized from a hexane/benzene solvent mixture to give 1,1,4,4,7-pentamethyl-5-hydroxy-1,2,3,4-tetrahydronaphthalene.

To prepare 6-formyl-1,1,4,4,7-pentamethyl-5-hydroxy-1,2,3,4-tetrahydronaphthalene, hexamethylenetetramine (21 g, 0.15 mol) and 1,1,4,4,7-pentamethyl-5-hydroxy-1,2,3,4-tetrahydronaphthalene are added in one portion, with stirring, to acetic acid (250 ml) and the mixture is heated at 95° C.–100° C. for 2 hrs. After cooling to 80° C.–85° C., water (250 ml) and concentrated hydrochloric acid (60 ml) are added and the mixture heated at 95° C.–100° C. for a further 2 hrs. The reaction product is then cooled to 20° C., diethyl ether (150 ml) is added, and the mixture stirred vigorously. The organic layer is separated, washed with brine (2×50 ml), neutralized with 5% sodium bicarbonate solution (100 ml), and dried ($Na_2SO_4$). The solvent is removed by distillation and the residue is distilled to yield 6-formyl-1,1,4,4,7-pentamethyl-5-hydroxy-1,2,3,4-tetrahydronaphthalene.

To convert the 6-carboxaldehyde, 6-formyl-1,1,4,4,7-pentamethyl-5-hydroxy-1,2,3,4-tetrahydronaphthalene, to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 3.8 g of 6-formyl-1,1,4,4,7-pentamethyl-5-hydroxy-1,2,3,4-tetrahydronaphthalene in 4 ml of dichloromethane. During the addition which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,4,4,7-pentamethyl-5-hydroxy-1,2,3,4-tetrahydronaphthalene-6-ol formate ester. The crude product may then be further purified using standard fractional distillation techniques.

EXAMPLE 16

Preparation of
7-Ethyl-1,1,4,4-Tetramethyl-5-Hydroxy-1,2,3,4-Tetrahydronaphthalene-6-ol Formate Ester The starting material 7-ethyl-1,1,4,4-tetramethyl-5-hydroxy-1,2,3,4-tetrahydronaphthalene is prepared by substantially following the procedures of Willis et al., U.S. Pat. No. 4,605,778. Specifically, concentrated hydrochloric acid (8.260 g, 86 mol) is added in one portion to 2,5-dimethyl-2,5-hexane diol (4.478 g, 46.65 mol). The resulting solution is heated for 6 hr, with stirring, at 22° C.–75° C., while passing hydrogen chloride gas (200 g). Then the reaction mixture is cooled to 25° C., hexane (3.5 liter) added, and the mixture stirred vigorously. The organic layer is separated, washed with water (2×1 liter), neutralized with 5% sodium bicarbonate solution and dried ($Na_2SO_4$). The solvent is removed by distillation and the residue crystallized from hexane to yield 2,5-dimethyl-2,5-dichlorohexane.

Next, 2,5-dimethyl-2,5-dichlorohexane (183 g, 1 mol) is stirred with 3-ethylphenol (146.4 g, 1.2 mol) and aluminum chloride (4 g) is added. The mixture is heated at 95° C., with stirring, for 1.5 hr, after which ethylene dichloride (100 ml) is added, and then the heating continued. After 1 hr, the mixture is cooled to 20° C., and poured onto an ice water/hydrochloric acid mixture (150 ml, 10% HCl solution). The mixture is then extracted with toluene (500 ml), the organic layer separated, washed with brine (3×50 ml) and dried ($Na_2SO_4$). The solvent is removed by distillation and the residue crystallized from a hexane/benzene solvent mixture to give 7-ethyl-1,1,4,4-tetramethyl-5-hydroxy-1,2,3,4-tetrahydro-naphthalene.

To prepare 6-formyl-7-ethyl-1,1,4,4-tetramethyl-5-hydroxy-1,2,3,4-tetrahydronaphthalene, hexamethylenetetramine (21 g, 0.15 mol) and 7-ethyl-1,1,4,4-tetramethyl-5-hydroxy-1,2,3,4-tetrahydro-naphthalene are added in one portion, with stirring, to acetic acid (250 ml) and the mixture is heated at 95° C.–100° C. for 2 hrs. After cooling to 80° C.–85° C., water (250 ml) and concentrated hydrochloric acid (60 ml) are added and the mixture heated at 95° C.–100° C. for a further 2 hrs. The reaction product is then cooled to 20° C., diethyl ether (150 ml) is added, and the mixture stirred vigorously. The organic layer is separated, washed with brine (2×50 ml), neutralized with 5% sodium bicarbonate solution (100 ml), and dried ($Na_2SO_4$). The solvent is removed by distillation and the residue is distilled to yield 6-formyl-7-ethyl-1,1,4,4-tetramethyl-5-hydroxy-1,2,3,4-tetrahydronaphthalene.

To convert the 6-carboxaldehyde, 6-formyl-7-ethyl-1,1,4,4-tetramethyl-5-hydroxy-1,2,3,4-tetrahydronaphthalene to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 4.0 g of 6-formyl-7-ethyl-1,1,4,4-tetramethyl-5-hydroxy-1,2,3,4-tetrahydronaphthalene in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 7-ethyl-1,1,4,4-tetramethyl-5-hydroxy-1,2,3,4-tetrahydronaphthalene-6-ol formate ester. The crude product may then be further purified using standard fractional distillation techniques.

EXAMPLE 17

Preparation of
7-Ethyl-1,1,4,4-Tetramethyl-5-Methoxy-1,2,3,4-Tetrahydronaphthalene-6-ol Formate Ester The starting material 7-ethyl-1,1,4,4-tetramethyl-5-hydroxy-1,2,3,4-tetrahydronaphthalene is prepared by substantially following the procedures of Willis et al., U.S. Pat. No. 4,605,778. Specifically, concentrated hydrochloric acid (8.260 g, 86 mol) is added in one portion to 2,5-dimethyl-2,5-hexane diol (4.478 g, 46.65 mol). The resulting solution is heated for 6 hr, with stirring, at 22° C.-75° C., while passing hydrogen chloride gas (200 g). Then the reaction mixture is cooled to 25° C., hexane (3.5 liter) added, and the mixture stirred vigorously. The organic layer is separated, washed with water (2×1 liter), neutralized with 5% sodium bicarbonate solution and dried ($Na_2SO_4$). The solvent is removed by distillation and the residue crystallized from hexane to yield 2,5-dimethyl-2,5-dichlorohexane.

Next, 2,5-dimethyl-2,5-dichlorohexane (183 g, 1 mol) is stirred with 3-ethylphenol (146.4 g, 1.2 mol) and aluminum chloride (4 g) is added. The mixture is heated at 95° C., with stirring, for 1.5 hr, after which ethylene dichloride (100 ml) is added, and then the heating continued. After 1 hr, the mixture is cooled to 20° C., and poured onto an ice water/hydrochloric acid mixture (150 ml, 10% HCl solution). The mixture is then extracted with toluene (500 ml), the organic layer separated, washed with brine (3×50 ml) and dried ($Na_2SO_4$). The solvent is removed by distillation and the residue crystallized from a hexane/benzene solvent mixture to give 7-ethyl-1,1,4,4-tetramethyl-5-hydroxy-1,2,3,4-tetrahydronaphthalene.

To prepare 6-formyl-7-ethyl-1,1,4,4-tetramethyl-5-hydroxy-1,2,3,4-tetrahydronaphthalene, hexamethylenetetramine (21 g, 0.15 mol) and 7-ethyl-1,1,4,4-tetramethyl-5-hydroxy-1,2,3,4-tetrahydronaphthalene are added in one portion, with stirring, to acetic acid (250 ml) and the mixture is heated at 95° C.-100° C. for 2 hrs. After cooling to 80° C.-85° C., water (250 ml) and concentrated hydrochloric acid (60 ml) are added and the mixture heated at 95° C.-100° C. for a further 2 hrs. The reaction product is then cooled to 20° C., diethyl ether (150 ml) is added, and the mixture stirred vigorously. The organic layer is separated, washed with brine (2×50 ml), neutralized with 5% sodium bicarbonate solution (100 ml), and dried ($Na_2SO_4$). The solvent is removed by distillation and the residue is distilled to yield 6-formyl-7-ethyl-1,1,4,4-tetramethyl-5-hydroxy-1,2,3,4-tetrahydronaphthalene.

To prepare 6-formyl-7-ethyl-1,1,4,4-tetramethyl-5-methoxy-1,2,3,4-tetrahydronaphthalene, a solution of sodium hydroxide (0.98 g, 0.0244 mol) in water (24 ml) is added in one portion to a solution of 6-formyl-7-ethyl-1,1,4,4-tetramethyl-5-hydroxy-1,2,3,4-tetrahydronaphthalene (3 g, 0.0122 mol), dimethyl sulfate (3.07 g, 0.0244 mol) and methyltrialkyl($C_8$-$C_{10}$)ammonium chloride (Adogen 464 TM ) (0.56 g) in methylene chloride (48 ml). The mixture is stirred vigorously at 38° C.-40° C. for 4 hrs. After cooling, the organic layer is separated, washed with brine (3×20 ml), and dried ($Na_2SO_4$). The solvent is removed by distillation and the residue is distilled to yield 6-formyl-7-ethyl-1,1,4,4-tetramethyl-5-methoxy-1,2,3,4-tetrahydro-naphthalene.

To convert the 6-carboxaldehyde, 6-formyl-7-ethyl-1,1,4,4-tetramethyl-5-methoxy-1,2,3,4-tetrahydronaphthalene to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 4.0 g of 6-formyl-7-ethyl-1,1,4,4-tetramethyl-5-methoxy-1,2,3,4-tetrahydronaphthalene in 4 ml of dichloromethane. During the addition which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 7-ethyl-1,1,4,4-tetramethyl-5-methoxy-1,2,3,4-tetrahydronaphthalene-6-ol formate ester. The crude product may then be further purified using standard fractional distillation techniques.

EXAMPLE 18

Preparation of
1,1,2,4,4,7-Hexamethyl-5-Methoxy-1,2,3,4-Tetrahydronaphthalene-6-ol Formate Ester Using a Perrier modification, Perrier, *Chem. Ber.*, Vol. 33, pp. 819 et seq. (1900), and Perrier, *Bull. Soc. Chim. France*, pp. 859 et seq. (1904), m-cresol methyl ether (122.0 g) is reacted with acetyl chloride (72.0 g), methylene chloride (500 ml), and aluminum chloride (145.0 g) to provide a mixture of 2-methoxy-4-methyl-acetophenone and 4-methoxy-2-methyl-acetophenone. After standard quenching, separation, drying and solvent evaporation, the mixture is distilled on a spinning band distillation column under vacuum to separate the components.

Methylmagnesium bromide (3.0M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 2- methoxy-4-methyl-acetophenone (22.53 g). After about 2 hours, an aliquot of additional Grignard (20 ml) is added. The solution is then heated at 60° C. for about one hour, and quenched with aqueous NH$_4$Cl. The aqueous layer is then washed several times with methyl tert-butyl ether and rotoevaporated to yield a crude product mixture containing 1-[2'-methoxy-4'-methylphenyl]-1-methylethanol. The product mixture is then fractionated under reduced pressure to further purify the 1-[2'-methoxy-4'-methylphenyl]-1-methylethanol.

Next, 1-[2'-methoxy-4'-methylphenyl]-1-methylethanol is converted to 1,1,2,4,4,7-hexamethyl-5-methoxy-1,2,3,4-tetrahydronaphthalene by following procedures similar to those described in European Patent Application Publication No. 0 393 742. Specifically, to a stirred solution of 10 ml TiCl$_4$ in 120 ml dichloromethane (cooled to −5° C. under nitrogen), is added a mixture of 18.0 g of 1-[2'-methoxy-4'-methylphenyl]-1-methylethanol and 16.8 g 2,3-dimethylbutene-1 over a two hour period. The reaction mixture is stirred for a further 30 mins at −5° C. Thereafter, it is poured into a mixture of 200 ml of water and 100 ml of concentrated hydrochloric acid and stirred for 15 mins. The organic phase is separated and the aqueous phase washed twice with 50 ml dichloromethane. The combined organic phase is washed twice with 100 ml 10% hydrochloric acid solution, once with 100 ml water, twice with 100 ml 5% sodium carbonate solution, and finally once again with water, to yield as a crude product, 1,1,2,4,4,7-hexamethyl-5-methoxy-1,2,3,4-tetrahydro-naphthalene. After removal of the solvent, the crude product may be further purified by fractional distillation under reduced pressure.

To convert 1,1,2,4,4,7-hexamethyl-5-methoxy-1,2,3,4-tetrahydronaphthalene to its corresponding 6-carboxaldehyde, a 250 ml flask is charged with 130 ml dichloromethane and 24.51 g TiCl$_4$. The solution is cooled to 2° C. and 14.9 g of 1,1,2,4,4,7-hexamethyl-5-methoxy-1,2,3,4-tetrahydronaphthalene and 20 ml dichloromethane are added with stirring. Then α,α-dichloromethyl methyl ether (13.37 g) is added over a period of 1.2 hours. After completion of addition, the solution is allowed to warm to room temperature. After a further half hour, the solution is quenched with water at a temperature of ≦8° C. The solution is distilled to remove residual starting material to yield a crude product containing the 6-carboxaldehyde, 6-formyl-1,1,2,4,4,7-hexamethyl-5-methoxy-1,2,3,4-tetrahydronaphthalene.

To convert the 6-carboxaldehyde to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.55 g of 6-formyl-1,1,2,4,4,7-hexamethyl-5-methoxy-1,2,3,4-tetrahydronapthalene in 4 ml of dichloromethane. During the addition which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,2,4,4,7-hexamethyl-5-methoxy-1,2,3,4-tetrahydronaphthalene-6-ol formate ester. The crude product may then be further purified using standard fractional distillation techniques.

EXAMPLE 19

Preparation of 1,1,2,4,4,5-Hexamethyl-7-Methoxy-1,2,3,4-Tetrahydronaphthalene-6-ol Formate Ester Using a Perrier modification, Perrier, *Chem. Ber.*, Vol. 33, pp. 819 et seq. (1900), and Perrier, *Bull. Soc. Chim. France*, pp. 859 et seq. (1904), m-cresol methyl ether (122.0 g) is reacted with acetyl chloride (72.0 g), methylene chloride (500 ml), and aluminum chloride (145.0 g) to provide a mixture of 2-methoxy-4-methyl-acetophenone and 4-methoxy-2-methyl-acetophenone. After standard quenching, separation, drying, and solvent evaporation, the mixture is distilled on a spinning band distillation column under vacuum to separate the components.

Methylmagnesium bromide (3.0M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 2-methyl-4-methoxy-acetophenone (22.53 g). After about 2 hours, an aliquot of additional Grignard (20 ml) is added. The solution is then heated at 60° C. for about one hour, and quenched with aqueous NH$_4$Cl. The aqueous layer is then washed several times with methyl tert-butyl ether and rotoevaporated to yield a crude product mixture containing 1-[4'-methoxy-2'-methylphenyl]-1-methylethanol. The product mixture is then fractionated under reduced pressure to further purify the 1-[4'-methoxy-2'-methylethanol.

Next, 1-[4'-methoxy-2'-methylphenyl]-1-methylethanol is converted to 1,1,2,4,4,5-hexamethyl-7-methoxy-1,2,3,4-tetrahydronaphthalene by following procedures similar to those described in European Patent Application Publication No. 0 393 742. Specifically, to a stirred solution of 10 ml TiCl$_4$ in 120 ml dichloromethane (cooled to −5° C. under nitrogen), is added a mixture of 18.0 g of 1-[4'-methoxy 2'-methylphenyl]-1-methylethanol and 16.8 g 2,3-dimethylbutene-1 over a two hour period. The reaction mixture is stirred for a further 30 mins at −5° C. Thereafter, it is poured into a mixture of 200 ml of water and 100 ml of concentrated hydrochloric acid and stirred for 15 mins. The organic phase is separated and the aqueous phase washed twice with 50 ml dichloromethane. The combined organic phase is washed twice with 100 ml 10% hydrochloric acid solution, once with 100 ml water, twice with 100 ml 5% sodium carbonate solution, and finally once again with water, to yield as a crude product, 1,1,2,4,4,5-hexamethyl-7-methoxy-1,2,3,4-tetrahydro-naphthalene. After removal of the solvent, the crude product is further purified by fractional distillation under reduced pressure.

To convert 1,1,2,4,4,5-hexamethyl-7-methoxy-1,2,3,4-tetrahydronaphthalene to its corresponding 6-carboxaldehyde, a 250 ml flask is charged with 130 ml dichloromethane and 24.51 g TiCl$_4$. The solution is cooled to 2° C. and 14.9 g of 1,1,2,4,4,5-hexamethyl-7-methoxy-1,2,3,4-tetrahydronaphthalene and 20 ml dichloromethane are added with stirring. Then α,α-dichloromethyl methyl ether (13.37 g) is added over a period of 1.2 hours. After completion of addition, the solution is allowed to warm to room temperature. After a further half hour, the solution is quenched with water at a temperature of ≦8° C. The solution is distilled to remove residual starting material to yield a crude product containing the 6-carboxaldehyde, 6- formyl-1,1,2,4,4,7-hexamethyl-5-methoxy-1,2,3,4-tetrahydronaphthalene.

To convert the 6-carboxaldehyde to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.55 g of 6-formyl-1,1,2,4,4,5-hexamethyl-7-methoxy-1,2,3,4-tetrahydronaphthalene in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,2,4,4,5-hexamethyl-7-methoxy-1,2,3,4-tetrahydronaphthalene-6-ol formate ester. The crude product may then be further purified using standard fractional distillation techniques.

EXAMPLE 20

Preparation of
1,1,2,4,4-Pentamethyl-5,7-Dimethoxy-1,2,3,4-Tetrahydronaphthalene-6-ol Formate Ester Using a Perrier modification, Perrier, Chem. Ber., Vol. 33, pp. 819 et seq. (1900), and Perrier, Bull. Soc. Chim. France, pp. 859 et seq. (1904), 1,3-dimethoxybenzene (138.0 g) (which may be obtained from Aldrich Chemical Company, Inc., Milwaukee, Wis.) is reacted with acetyl chloride (72.0 g), methylene chloride (500 ml), and aluminum chloride (145.0 g) to provide 2',4'-dimethoxy-acetophenone, which may then be purified using standard vacuum fractional distillation.

Methylmagnesium bromide (3.0M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 2',4'-dimethoxy-acetophenone (24.73 g). After about 2 hours, an aliquot of additional Grignard (20 ml) is added. The solution is then heated at 60° C. for about one hour, and quenched with aqueous NH4Cl. The aqueous layer is then washed several times with methyl tert-butyl ether and rotoevaporated to yield a crude product mixture containing 1-[2', 4'-dimethoxyphenyl]-1-methylethanol. The product mixture is then fractionated under reduced pressure to further purify the 1-[2',4'-dimethoxyphenyl]-1-methylethanol.

Next, 1-[2',4'-dimethoxyphenyl]-1-methylethanol is converted to 1,1,2,4,4-pentamethyl-5,7-dimethoxy-1,2,3,4-tetrahydronaphthalene by following procedures similar to those described in European Patent Application Publication No. 0 393 742. Specifically, to a stirred solution of 10 ml TiCl4 in 120 ml dichloromethane (cooled to −5° C. under nitrogen), is added a mixture of 19.61 g of 1-[2', 4'-dimethoxyphenyl]-1-methylethanol and 16.8 g 2,3-dimethylbutene-1 over a two hour period. The reaction mixture is stirred for a further 30 mins at −5° C. Thereafter, it is poured into a mixture of 200 ml of water and 100 ml of concentrated hydrochloric acid and stirred for 15 mins. The organic phase is separated and the aqueous phase washed twice with 50 ml dichloromethane. The combined organic phase is washed twice with 100 ml 10% hydrochloric acid solution, once with 100 ml water, twice with 100 ml 5% sodium carbonate solution, and finally once again with water, to yield as a crude product, 1,1,2,4,4-pentamethyl-5,7-dimethoxy-1,2,3,4-tetrahydronaphthalene. After removal of the solvent, the crude product Is further purified by fractional distillation under reduced pressure.

To convert 1,1,2,4,4-pentamethyl-5,7-dimethoxy-1,2,3,4-tetrahydronaphthalene to its corresponding 6-carboxaldehyde, a 250 ml flask is charged with 130 ml dichloromethane and 24.51 g TiCl4. The solution is cooled to 2° C. and 15.87 g of 1,1,2,4,4-pentamethyl-5,7-dimethoxy-1,2,3,4-tetrahydronaphthalene and 20 ml dichloromethane are added with stirring. Then α,α-dichloro methyl methyl ether (13.37 g) is added over a period of 1.2 hours. After completion of addition, the solution is allowed to warm to room temperature. After a further half hour, the solution is quenched with water at a temperature of ≦8° C. The solution is distilled to remove residual starting material to yield a crude product containing the 6-carboxaldehyde, 6-formyl-1,1,2,4,4-pentamethyl-5,7-dimethoxy-1,2,3,4-tetrahydronaphthalene.

To convert the 6-carboxaldehyde to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.64 g of 6-formyl-1,1,2,4,4-pentamethyl-5,7-dimethoxy-1,2,3,4-tetrahydronaphthalene in 4 ml of dichloromethane. During the addition which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,2,4,4-pentamethyl-5,7-dimethoxy-1,2,3,4-tetrahydronaphthalene-6-ol formate ester. The crude product may then be further purified using standard fractional distillation techniques.

EXAMPLE 21

Preparation of
1,2,6,7,8,8a-Hexahydro-3,6,6,8a-Tetramethylacenaphthylene-4-ol Formate Ester The starting material 1,2,6,7,8,8a-hexahydro-3,6,6,8a-tetramethyl-4-acenaphthylenecarbaldehyde is prepared by substantially following the procedures of Fehr et al., U.S. Pat. No. 5,162,588. Specifically, in a 2.5 liter flask equipped with a mechanical stirrer, a condenser, a thermometer and a nitrogen inlet, α-chloro-o-xylene (available from Fluka Chemical Corp., Ronkonkoma, N.Y., 140.6 g) is mixed with ethyl acetoacetate (130 g), a fine powder of potassium carbonate (414 g) and 800 ml of toluene. The mixture is heated to 100° C. for 20 h. After cooling, $H_2O$ is added (500 ml). The organic phase is washed with water and saturated NaCl, then dried over $Na_2SO_4$ and evaporated, resulting in a brown oil. The oil is distilled (120° C.–125° C./5.65 Pa) to yield ethyl-2-acetyl-3-(2-methyl-1-phenyl)propanoate.

An autoclave of 1 liter is charged with 161.5 g of ethyl-2-acetyl-3-(2 methyl-1-phenyl)propanoate, 16.4 g of NaCl, 150 ml of DMSO and 25 ml of $H_2O$. The mixture is heated to 160° C. for 7 hrs. The cooled reaction mixture is extracted with petroleum ether 30° C.–50° C., washed 5 times with a saturated solution of NaCl, dried over $Na_2SO_4$, filtered and evaporated. Distillation of the obtained raw product (13.3 Pa) provides 4-(2 methyl-1-phenyl)-2-butanone.

In a 1 liter flask, 2-methyl-3-butyn-2-ol (47 g) is added to a solution of EtMgBr (1.12 mol of Mg and 1.12 mol of ethyl bromide in 200 ml of anhydrous ether at reflux) over 30 min. while keeping the temperature at 0° C.–5° C. The heterogeneous mixture is heated to 20° C. for 30 min. under stirring, and then to reflux for 1 hr, 69.7 g of 4-(2-methyl-1-phenyl)-2-butanone is added and the reaction mixture is heated to reflux for 1 h. The mixture, by then homogeneous, is hydrolyzed with an aqueous solution saturated with $NH_4Cl$ and ice, extracted with ether, washed with saturated NaCl, dried and evaporated, to yield a yellow oil, containing 7-(2-methyl-1-phenyl)-2,5-dimethylhept-3-yne-2,5-diol.

Next, 60 g of 7-(2-methyl-1-phenyl)-2,5-dimethylhept-3-yne-2,5-diol is hydrogenated in an autoclave at 70° C. and 50 $H_2$ atmospheres, in the presence of about 3.0 g of Raney-Ni in methanol (80 g). After 4 days under the same conditions, the suspension is filtered and the filtrate evaporated to yield 7-(2-methyl-1-phenyl)-2,5-dimethylheptane-2,5-diol.

A stirred and cooled (4° C.) solution of 7-(2-methyl-1-phenyl)-2,5-dimethylheptane-2,5-diol (12.5 g) in 1,2-dichloro-ethane (150 ml) is then treated dropwise with $TiCl_4$ (16.5 ml). After stirring for 30 min, an aqueous solution saturated with NaCl (50 ml) is added dropwise, the temperature rising to 30° C. The mixture is washed with an aqueous solution saturated with $NaHCO_3$, then with an aqueous solution saturated with NaCl, dried over $Na_2SO_4$, evaporated and distilled (130° C./2.66 Pa), to yield 1,2,2a,3,4,5-hexahydro-2a,5,5,8-tetramethylacenaphthene.

Next, a mixture of 1,2,2a,3,4,5-hexahydro-2a,5,5,8-tetramethylacenaphthene (3.71 g) and $TiCl_4$ (7.32 g) in methylene chloride (40 ml) is treated with $Cl_2CHOCH_3$ (2.66 g) in methylene chloride (5 ml), at 0° C. and over 20 min. The temperature of the reaction mixture is allowed to reach 20° C. (20 min) and the mixture is then poured on ice water and extracted with ether. The organic phase is successively washed with 10% aqueous solution of NaOH, water and an aqueous solution saturated with NaCl, then dried over $Na_2SO_4$, evaporated and recrystallized from methanol, to yield 1,2,6,7,8,8a-hexahydro-3,6,6,8a-tetramethyl-4-acenaphthylenecarboxaldehyde.

To convert the 1,2,6,7,8,8a-hexahydro-3,6,6,8a-tetramethyl-4-acenaphthylenecarboxaldehyde to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 3.71 g of 1,2,6,7,8,8a-hexahydro-3,6,6,8a-tetramethyl-4-acenaphthylenecarboxaldehyde in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,2,6,7,8,8a-hexahydro-3,6,6,8a-tetramethyl-acenaphthylene-4-ol formate ester. The crude product may then be further purified using standard fractional distillation, or chromatography techniques.

EXAMPLE 22

Preparation of
2,3,3a,4,5,9b-Hexahydro-5,5,8,9b-Tetramethyl-1H-Benz[e]indene-7-ol Formate Ester and
2,3,3a,4,5,9b-Hexahydro-5,5,7,9b-Tetramethyl-1H-Benz[e]indene-8-ol Formate Ester The starting materials 2,3,3a,4,5,9b-hexahydro-5,5,8,9b-tetramethyl-1H-benz[e]indene-7-carboxaldehyde and 2,3,3a,4,5,9b-hexahydro-5,5,7,9b-tetramethyl-1H-benz[e]indene-8-ol formate ester are prepared by substantially following the procedures of Fehr et al., U.S. Pat. No. 5,162,588. Specifically, a mixture of methyl-1-cyclopentanone-2-carboxylate (available from Fluka Chemical Corp., Ronkonkoma, N.Y., 106.5 g), methallyl chloride (88 ml), $K_2CO_3$ (207 g) and acetone (500 ml) is heated to reflux for 2 hrs. More methallyl chloride (44 ml) is added and the mixture is refluxed for 20 hrs. The white reaction mass is dissolved in water and the product extracted with ether. Washing (3% aqueous NaOH) provides an oil which, upon fractional distillation (105° C.–107° C./5.32×$10^2$ Pa), yields methyl-1-(2-methyl-2-propenyl)-2-oxo-1-cyclopentanecarboxylate.

A mixture of methyl-1-(2-methyl-2-propenyl)-2-oxo-1-cyclopentanecarboxylate (78.4 g), HMPA (hexamethylphosphoramide, 250 ml) and LiCl (34 g) is heated to 73° C. for 36 hrs. Extraction (3 times, ether/water) of the reaction product provides a brown oil which, upon fractional distillation (63° C.–75° C./5.32×$10^2$ Pa), yields 2-(2-methyl-2-propenyl)-1-cyclopentanone.

Next, 2-(2-methyl-2-propenyl)-1-cyclopentanone (10.35 g) is added dropwise to a suspension of $AlCl_3$ (15 g) in toluene (138 g) at −20° C. The temperature is allowed to raise to 10° C. and the reaction mixture is stirred for 30 min, hydrolyzed with water and extracted with ether. The yellow oil thus obtained is distilled in a bulb-to bulb apparatus (130° C./1.33 Pa) to yield a mixture of 2-[2-methyl-2-(4-methyl-1-phenyl)propyl]-1-cyclopentanone and 2-(2-methyl-2-(3-methyl-1-phenyl)-propyl]-1-cyclopentanone.

A solution of CH$_3$MgI (prepared with 3.4 ml of CH$_3$I and 1.2 g of Mg) in ether (100 ml) is treated at 20° C. with a solution of the mixture of 2-[2-methyl-2-(4-methyl-1-phenyl)propyl]-1-cyclopentanone and 2-(2-methyl-2-(3-methyl-1-phenyl)propyl]-1-cyclopentanone (10.44 g) in ether (10 ml), to yield 1-methyl-2-[2-methyl-2-(4-methyl-1-propyl]-1-cyclopentanol and 1-methyl-2-[2-methyl-2-(3-methyl-1-phenyl) propyl]-1-cyclopentanol. The reaction takes about 10 min to complete. The mixture of 1-methyl-2-[2-methyl-2-(4-methyl-1-phenyl)-propyl]-1-cyclopentanol and 1-methyl-2-[2-methyl-2-(3-methyl-1-phenyl)propyl]-1-cyclopentanol is then hydrolyzed and extracted with ether.

A solution of the 1-methyl-2-[2-methyl-2-(4-methyl-1-phenyl)propyl]-1-cyclopentanol and 1-methyl-2-[ 2-methyl-2-(3-methyl-1-phenyl)propyl]-1-cyclopentanol mixture (9.84 g), petroleum ether 30° C.-50° C. (150 ml) and 98% H$_2$SO$_4$ (0.75 ml) is prepared and stirred for 1 hr while maintaining the temperature at 20° C. The reaction mixture is then extracted and bulb-to-bulb distilled (130° C./5.65 Pa) to yield a mixture of 1-[1,1-dimethyl-2-(2-methyl-1-cyclopenten-1-yl)ethyl]-4-methylbenzene and 1-[1,1-dimethyl-2-(2-methyl-1-cyclopenten-1-yl)ethyl]-3-methylbenzene.

A solution of the mixture of 1-[1,1-dimethyl-2-(2-methyl-1-cyclopenten-1-yl)ethyl]-4-methylbenzene and 1-[1,1-dimethyl-2-(2-methyl-1-cyclopenten-1-yl)ethyl]-3-methylbenzene (5.5 g), petroleum ether 30° C.-50° C. (120 ml) and 98% H$_2$SO$_4$ (0.5 ml) is heated to reflux (50° C.) for 5 hrs. Extraction and bulb-to-bulb distillation (140° C./13.3 Pa) provides a mixture of 1,2,3,3a,4,5-hexahydro-1a,5,5,8-tetramethylacenaphthylene and 1,2,3,3a,4,5-hexahydro-1a,5,5,7-tetramethylacenaphthylene.

A mixture of 1,2,3,3a,4,5-hexahydro-1a,5,5,8-tetramethylacenaphthylene and 1,2,3,3a,4,5-hexahydro-1a,5,5,7-tetramethylacenaphthylene (5 g) and TiCl$_4$ (1.86 ml) in methylene chloride (30 ml) is treated with Cl$_2$CHOCH$_3$ (0.8 ml) in methylene chloride (5 ml) at 0° C. and over 20 min. The temperature of the reaction is allowed to reach 20° C. (20 min) and the mixture is poured over ice water and extracted with ether. The organic phase is successively washed with a 10% aqueous solution of NaOH, water and an aqueous solution saturated with NaCl, then dried over Na$_2$SO$_4$, evaporated and recrystallized from methanol to yield a mixture of the isomers 2,3,3a,4,5,9b-hexahydro-5,5,8,9b-tetramethyl-1H-benz[e]indene-7-carboxaldehyde and 2,3,3a,4,5,9b-hexahydro-5,5,7,9b-tetramethyl-1H-benz[e]indene-8-carboxaldehyde.

To convert the compounds 2,3,3a,4,5,9b-hexahydro-5,5,8,9b-tetramethyl-1H-benz[e]indene-7-carboxaldehyde and 2,3,3a,4,5,9b-hexahydro-5,5,7,9b-tetramethyl-1H-benz[e]indene-8-carboxaldehyde to their corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 3.92 g of a mixture of 2,3,3a,4,5,9b-hexahydro-5,5,8,9b-tetramethyl-1H-benz[e]indene-7-carboxaldehyde and 2,3,3a,4,5,9b-hexahydro-5,5,7,9b-tetramethyl-1H-benz[e]indene-8-carboxaldehyde in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing a mixture of 2,3,3a,4,5,9b-hexahydro-5,5,8,9b-tetramethyl-1H-benz[e]indene-7-ol formate ester and 2,3,3a,4,5,9b hexahydro 5,5,7,9b-tetramethyl-1H-benz[e]indene-8-ol formate ester. The crude product may then be further purified using standard fractional distillation, or chromatography techniques.

EXAMPLE 23

Preparation of 1,1,2,4,4-Pentamethyl-5-Methoxy-1,2,3,4-Tetrahydronaphthalene-7-ol Formate Ester Using a Perrier modification, Perrier, *Chem. Ber.*, Vol. 33, pp. 819 et seq. (1900), and Perrier, *Bull. Soc. Chim. France*, pp. 859 et seq. (1904), m-cresol methyl ether (122.0 g) is reacted with acetyl chloride (72.0 g), methylene chloride (500 ml), and aluminum chloride (145.0 g) to provide a mixture of 2-methoxy-4-methyl-acetophenone and 4-methoxy-2-methyl-acetophenone. After standard quenching, separation, drying and solvent evaporation, the mixture is distilled on a spinning band distillation column under vacuum to separate the components.

Methylmagnesium bromide (3.0M, 100 ml) (which may be obtained from Aldrich Chemical Company, Inc., Milwaukee, Wis.) in ether is added at room temperature to a 250 ml four-necked round bottom flask equipped with an air stirrer, septum, Claisen adapter (thermocouple and dry ice condenser attached) and nitrogen inlet tube. To this is then slowly added 2-methoxy-4-methyl-acetophenone (22.53 g). After about 2 hours, an aliquot of additional Grignard (20 ml) is added. The solution is then heated at 60° C. for about one hour, and quenched with aqueous NH$_4$Cl. The aqueous layer is then washed several times with methyl tert-butyl ether and rotoevaporated to yield a crude product mixture containing 1-[2'-methoxy-4'-methylphenyl]-1-methylethanol. The product mixture is then fractionated under reduced pressure to further purify the 1-[2'-methoxy-4'-methylphenyl]-1-methylethanol.

Next, 1-[2'-methoxy-4'-methylphenyl]-1-methylethanol is converted to 1,1,2,4,4,7-hexamethyl-5-methoxy-1,2,3,4-tetrahydronaphthalene by following procedures similar to those described in European Patent Application Publication No. 0 393 742. Specifically, to a stirred solution of 10 ml TiCl$_4$ in 120 ml dichloromethane (cooled to −5° C. under nitrogen), is added a mixture of 18.0 g of 1-[2'-methoxy-4'-methylphenyl]-1-methylethanol and 16.8 g 2,3-dimethylbut-1-ene over a two hour period. The reaction mixture is stirred for a further 30 mins at −5° C. Thereafter, it is poured into a mixture of 200 ml of water and 100 ml of concentrated hydrochloric acid and stirred for 15 mins. The organic phase is separated and the aqueous phase washed twice with 50 ml dichloromethane. The combined organic phase is washed twice with 100 ml 10% hydrochloric acid solution, once with 100 ml water, twice with 100 ml 5% sodium carbonate solution, and finally once again with water, to yield as a crude product, 1,1,2,4,4,7-hexamethyl-5-methoxy-1,2,3,4-tetrahydro-naphthalene. After removal of the solvent, the crude product is further purified by fractional distillation under reduced pressure.

To convert 1,1,2,4,4,7-hexamethyl-5-methoxy-1,2,3,4-tetrahydronaphthalene to 7-formyl-1,1,2,4,4-pentamethyl-5-methoxy-1,2,3,4-tetrahydronaphthalene, the oxidation procedures of Syper, Tetrahedron Letters, No. 37, pp. 4493-4498 (1966) are substantially followed. Specifically, to a solution of 14.8 g of 1,1,2,4,4,7-hexamethyl-5-methoxy-1,2,3,4-tetrahydronaphthalene in 300 ml of 50% aqueous acetic acid is prepared. While stirring, to this is added dropwise a solution of 131.5 g ceric ammonium nitrate in the same acid (600 ml), at 100° C. The solution is then cooled to room temperature, diluted with water, extracted three times with ether, and dried with MgSO4, to yield the 7-carboxaldehyde, 7-formyl- 1,1,2,4,4-pentamethyl-5-methoxy-1,2,3,4-tetrahydronaphthalene.

To convert the 7-carboxaldehyde to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.55 g of 7-formyl-1,1,2,4,4-pentamethyl-5-methoxy-1,2,3,4-tetrahydronaphthalene in 4 ml of dichloromethane. During the addition, which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,2,4,4-pentamethyl-5-methoxy-1,2,3,4-tetrahydronaphthalene-7-ol formate ester. The crude product may then be further purified using standard fractional distillation techniques.

EXAMPLE 24

Preparation of 1,1,2,4,4-Pentamethyl-1,2,3,4-Tetrahydronaphthalene-7-ol Formate Ester The starting material 1,1,3,4,4,6-hexamethyl-1,2,3,4-tetrahydronaphthalene (HMT) is prepared by substantially following the procedures of Frank, U.S. Pat. No. 4,877,913. Specifically, a 100 ml, four-necked, round bottom flask is charged with cyclohexane (7.17 g) and anhydrous aluminum chloride (1.004 g), and cooled to about 16° C. A 60 ml addition funnel is charged with para-cymene (39.87 g), diisobutylene-2 (8.34 g), and neohexene (6.25 g) and connected to the flask. The funnel mixture is added to the flask over a period of about one hour and the flask mixture stirred 30 minutes following addition, while maintaining the temperature at about 16° C. The reaction is then quenched with deionized water (15 ml), and the organic phase separated and washed with, in order, 5% HCl, 10% Na2CO3, and 50% brine. The aqueous layers are then dried over K2CO3, filtered, and evaporated to yield a crude product containing HMT.

To convert HMT to 7-formyl-1,1,2,4,4-pentamethyl-1,2,3,4-tetrahydronaphthalene, the oxidation procedures of Syper, Tetrahedron Letters, No. 37, pp. 4493-4498 (1966) are substantially followed. Specifically, to a solution of 13.8 g of HMT in 300 ml of 50% aqueous acetic acid is prepared. While stirring, to this is added dropwise a solution of 131.5 g ceric ammonium nitrate in the same acid (600 ml), at 100° C. The solution is then cooled to room temperature, diluted with water, extracted three times with ether, and dried with MgSO4, to yield the 7-carboxaldehyde, 7-formyl-1,1,2,4,4-pentamethyl-1,2,3,4-tetrahydronaphthalene.

To convert the 7-carboxaldehyde to its corresponding formate ester, the following procedure is carried out. To a 25 ml 3-necked round bottomed flask equipped with a thermocouple, mechanical stirrer, and Claisen adapter (which is connected to an addition funnel and condenser), is charged with 2.1 g of meta-chloroperbenzoic acid (60% purity from Aldrich Chemical Company, Inc., Milwaukee, Wis.) and 10 ml of dichloromethane. The mixture is stirred for 10 minutes at 22° C., and then cooled to 11° C. To this reaction mixture is added dropwise a solution of 1.55 g of 7-formyl-1,1,2,4,4-pentamethyl-1,2,3,4-tetrahydronaphthalene in 4 ml of dichloromethane. During the addition which takes about 0.5 hours, the temperature is raised to 22° C., and is maintained for two hours after the addition is completed. The reaction is quenched with water, and transferred to a separatory funnel. The organics are washed with a saturated solution of sodium metabisulfite until the peroxide test is negative, then washed successively with sodium bicarbonate and brine dried over anhydrous sodium sulfate, filtered, and rotary evaporated to give a crude product containing 1,1,2,4,4-pentamethyl-1,2,3,4-tetrahydronaphthalene- 7-ol formate ester. The crude product may then be further purified using standard fractional distillation techniques.

The disclosures of each patent and publication cited or described herein are hereby incorporated herein by reference, in their entirety.

Various modifications of the invention, in addition to those shown and described herein, will be readily apparent to those skilled in the art from the foregoing description. Such modifications are also intended to fall within the scope of the appended claims.

What is claimed is:

1. A compound of the formula:

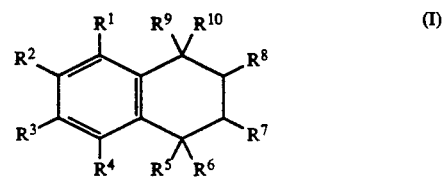

wherein $R^1$ is —H, —CH3, —CH2CH3, —OCH3 or —OH, $R^2$ and $R^3$ are, independently, —H, —CH$_3$, —CH$_2$CH$_3$, OCH$_3$, —OH or —OC(O)H, $R^4$ is —H, $R^5$ is —H, —CH$_3$ or —CH$_2$CH$_3$, or $R^4$ and $R^5$, taken together, are —(CH$_2$)$_2$, $R^6$ is —CH$_3$ or —CH$_2$CH$_3$, $R^7$ is —H, —CH$_3$ or CH$_2$CH$_3$, or $^6$ and $R^7$, taken together, are —(CH$_2$)$_3$—, $R^8$ and $R^9$ are, independently, —H, —CH$_3$ or —CH$_2$CH$_3$, and $R^{10}$ is —CH$_3$, provided that (i) one of $R^2$ and $R^3$ is —OC(O)H, and one of $R^2$ and $R^3$ is other than —OC(O)H, (ii) when $R^1$ is —H, then $R^2$ and $R^3$ are other than —OCH$_3$ or —OH, (iii) no more than one of $R^5$ and $R^9$ is —H, (iv) no more than one of $R^5$, $R^6$, $R^7$, $R^8$ and $R^9$ is —CH$_2$CH$_3$, (v) when $R^1$ is —OCH$_3$, then $R^2$ and $R^3$ are other than —H or —OH, (vi) when $R^1$ is —OH, then $R^2$ and $R^3$ are other than —OH or —OCH$_3$, (vii) when $R^1$ is —CH$_3$ or —CH$_2$CH$_3$, then at least one of $R^7$ and $R^8$ are H, (viii) when $R^4$ and $R^5$, taken together, are —(CH$_2$)$_2$—, then $R^1$ is —H, —OCH$_3$ or —OH, $R^7$ is —H, and $R^8$ is —H, and (ix) when $R^6$ and $R^7$, taken together, are —(CH$_2$)$_3$—, then $R^1$ is —H, —OCH$_3$ or —OH, and $R^8$ is —H.

2. A compound of claim 1 wherein $R^1$ is —H, —CH$_3$, —OH or —OCH$_3$.

3. A compound of claim 1 wherein $R^2$ is —OC(O)H.

4. A compound of claim 1 wherein $R^3$ is —CH$_3$ or —CH$_2$CH$_3$.

5. A compound of claim 1 wherein $R^1$ is —OH or —OCH$_3$, $R^2$ is —OC(O)H, $R^3$ is —CH$_3$ or —CH$_2$CH$_3$, $R^4$ is —H, $R^5$ is —CH$_3$, $R^6$ is —CH$_3$, $R^7$ is —H or —CH$_3$, $R^8$ is —H or —CH$_3$, $R^9$ is —CH$_3$, and $R^{10}$ is —CH$_3$.

6. A compound of claim 1 wherein $R^1$ is —H or —CH$_3$, $R^2$ is —OC(O)H, $R^3$ is —CH$_3$ or —CH$_2$CH$_3$, $R^4$ is H, $R^5$ is —CH$_3$, $R^6$ is —CH$_3$, $R^7$ is —H or CH$_3$, $R^8$ is —H or —CH$_3$, $R^9$ is —CH$_3$, and $R^{10}$ is —CH$_3$.

7. A compound of claim 1 wherein $R^1$ is —H, —OH or —OCH$_3$, $R^2$ is —OC(O)H, $R^3$ is —CH$_3$, $R^4$ and $R^5$, taken together, are —(CH$_2$)$_2$—, $R^6$ is —CH$_3$, $R^7$ is —H, $R^8$ is —H, $R^9$ is —CH$_3$, and $R^{10}$ is —CH$_3$.

8. A compound of claim 1 wherein $R^1$ is —H, —OH or —OCH$_3$, $R^2$ is —OC(O)H, $R^3$ is —CH$_3$, $R^4$ is —H, $R^5$ is —CH$_3$, $R^6$ and $R^7$, taken together, are —(CH$_2$)$_3$—, $R^8$ is —H, $R^9$ is —CH$_3$, and $R^{10}$ is —CH$_3$.

9. A compound of claim 5 wherein $R^1$ is —OCH$_3$, $R^3$ is —CH$_3$, $R^7$ is —H, and $R^8$ is —H.

10. A compound of claim 5 wherein $R^1$ is —OCH$_3$, $R^3$ is —CH$_2$CH$_3$, $R^7$ is —H, and $R^8$ is —H.

11. A compound of claim 5 wherein $R^1$ is —OH, $R^3$ is —CH$_3$, $R^7$ is —H, and $R^8$ is —H.

12. A compound of claim 5 wherein $R^1$ is —OH, $R^3$ is —CH$_3$CH$_2$, $R^7$ is —H, and $R^8$ is —H.

13. A compound of claim 5 wherein $R^1$ is —OCH$_3$, $R^3$ is —CH$_3$, $R^7$ is —CH$_3$, and $R^8$ is —H.

14. A compound of claim 5 wherein $R^1$ is —OCH$_3$, $R^3$ is —CH$_2$CH$_3$, $R^7$ is —CH$_3$, and $R^8$ is —H.

15. A compound of claim 5 wherein $R^1$ is —OH, $R^3$ is —CH$_3$, $R^7$ is —CH$_3$, and $R^8$ is —H.

16. A compound of claim 5 wherein $R^1$ is —OH, $R^3$ is —CH$_2$CH$_3$, $R^7$ is —CH$_3$, and $R^8$ is —H.

17. A compound of claim 6 wherein $R^1$ is —H, $R^3$ is —CH$_3$, $R^7$ is —CH$_3$, and $R^8$ is —H.

18. A compound of claim 6 wherein $R^1$ is —H, $R^3$ is —CH$_3$, $R^7$ is —H, and $R^8$ is —H.

19. A compound of claim 6 wherein $R^1$ is —H, $R^3$ is —CH$_3$, $R^7$ is —H, and $R^8$ is —CH$_3$.

20. A compound of claim 6 wherein $R^1$ is —CH$_3$, $R^3$ is —CH$_3$, $R^7$ is —CH$_3$, and $R^8$ is —H.

21. A compound of claim 6 wherein $R^1$ is —CH$_3$, $R^3$ is —CH$_3$, $R^7$ is —H, and $R^8$ is —H.

22. A compound of claim 6 wherein $R^1$ is —CH$_3$, $R^3$ is —CH$_3$, $R^7$ is —H, and $R^8$ is —CH$_3$.

23. A compound of claim 6 wherein $R^1$ is —H, $R^3$ is —CH$_3$, $R^7$ is —CH$_3$, and $R^8$ is —CH$_3$.

24. A compound of claim 6 wherein $R^1$ is —H, $R^3$ is —CH$_2$CH$_3$, $R^7$ is —H, and $R^8$ is —H.

25. A compound of claim 7 wherein $R^1$ is —H.

26. A compound of claim 8 wherein $R^1$ is —H.

27. A fragrance composition comprising a compound of claim 1 in combination with at least one of a carrier and additional perfumery material.

28. A fragrance composition comprising a compound of claim 6 in combination with at least one of a carrier and additional perfumery material.

29. A fragrance composition comprising a compound of claim 9 in combination with at least one of a carrier and additional perfumery material.

30. A fragrance composition comprising a compound of claim 11 in combination with at least one of a carrier and additional perfumery material.

31. A fragrance composition comprising a compound of claim, 13 in combination with at least one of a carrier and additional perfumery material.

32. A fragrance composition comprising a compound of claim 17 in combination with at least one of a carrier and additional perfumery material.

33. A fragrance composition comprising a compound of claim 23 in combination with at least one of a carrier and additional perfumery material.

34. A fragrance composition comprising a compound of claim 24 in combination with at least one of a carrier and additional perfumery material.

35. A method of modifying the olfactory properties of a composition comprising adding thereto an olfactorily effective amount of a compound of claim 1.

36. A method of modifying the olfactory properties of a composition comprising adding thereto an olfactorily effective amount of a compound of claim 6.

37. A method of modifying the olfactory properties of a composition comprising adding thereto an olfactorily effective amount of a compound of claim 9.

38. A method of modifying the olfactory properties of a composition comprising adding thereto an olfactorily effective amount of a compound of claim 11.

39. A method of modifying the olfactory properties of a composition comprising adding thereto an olfactorily effective amount of a compound of claim 13.

40. A method of modifying the olfactory properties of a composition comprising adding thereto an olfactorily effective amount of a compound of claim 17.

41. A method of modifying the olfactory properties of a composition comprising adding thereto an olfactorily effective amount of a compound of claim 23.

42. A method of modifying the olfactory properties of a composition comprising adding thereto an olfactorily effective amount of a compound of claim 24.

* * * * *

UNITED STATES PATENT AND TRADEMARK OFFICE
CERTIFICATE OF CORRECTION

PATENT NO. : 5,292,719
DATED : March 8, 1994
INVENTOR(S) : Walter C. Frank

It is certified that error appears in the above-identified patent and that said Letters Patent is hereby corrected as shown below:

Column 71, claim 1, line 5, change "or $R^4$ and $R^5$, taken together, are $-(CH_2)_2$" to -- or $R^4$ and $R^5$, taken together, are $-(CH_2)_2-$, --

Column 71, line 7, change "$R^7$ is $-H$, $-CH_3$ or $CH_2CH_3$," to -- $R^7$ is $-H$, $-CH_3$ or $-CH_2CH_3$, --

Signed and Sealed this

Twentieth Day of September, 1994

Attest:

BRUCE LEHMAN

Attesting Officer

Commissioner of Patents and Trademarks